# (12) United States Patent
Jung et al.

(10) Patent No.: US 10,104,893 B2
(45) Date of Patent: Oct. 23, 2018

(54) PESTICIDALLY ACTIVE POLYCYCLIC DERIVATIVES WITH SULFUR SUBSTITUTED FIVE MEMBERED RING HETEROCYLES

(71) Applicant: Syngenta Participations AG, Basel (CH)

(72) Inventors: Pierre Joseph Marcel Jung, Stein (CH); Andrew Edmunds, Stein (CH); Michel Muehlebach, Stein (CH); Peter Renold, Stein (CH); Roger Graham Hall, Stein (CH); Jerome Yves Cassayre, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/568,829

(22) PCT Filed: Apr. 18, 2016

(86) PCT No.: PCT/EP2016/058526
§ 371 (c)(1),
(2) Date: Oct. 24, 2017

(87) PCT Pub. No.: WO2016/169882
PCT Pub. Date: Oct. 27, 2016

(65) Prior Publication Data
US 2018/0110226 A1    Apr. 26, 2018

(30) Foreign Application Priority Data

Apr. 24, 2015 (EP) .................................... 15164953
Sep. 7, 2015 (EP) .................................... 15184067

(51) Int. Cl.
| | | |
|---|---|---|
| C07D 401/02 | (2006.01) | |
| C07D 401/10 | (2006.01) | |
| C07D 401/14 | (2006.01) | |
| A61K 31/437 | (2006.01) | |
| A61K 31/4353 | (2006.01) | |
| A01N 43/90 | (2006.01) | |
| A01N 43/40 | (2006.01) | |
| C07D 409/12 | (2006.01) | |
| C07D 471/04 | (2006.01) | |

(52) U.S. Cl.
CPC ............. A01N 43/90 (2013.01); A01N 43/40 (2013.01); C07D 409/12 (2013.01); C07D 471/04 (2013.01)

(58) Field of Classification Search
USPC .......................... 546/119, 121; 514/300, 303
See application file for complete search history.

(56) References Cited

U.S. PATENT DOCUMENTS

2014/0364444 A1    12/2014 Takyo et al.

FOREIGN PATENT DOCUMENTS

| EP | 2857396 A1 | 4/2015 |
| WO | 2013180193 | * 12/2013 |
| WO | 2015/000715 A1 | 1/2015 |

OTHER PUBLICATIONS

Extended European Search Report for EP15164953.0, dated Sep. 24, 2015.
International Search Report and Written Opinion for PCT/EP2016/058526, dated Jun. 1, 2016.

* cited by examiner

*Primary Examiner* — Niloofar Rahmani

(57) ABSTRACT

Compounds of formula (I) wherein Q is ($Q_1$) or ($Q_2$); and wherein the other substituents are as defined in claim 1, and the agrochemically acceptable salts, stereoisomers, enantiomers, tautomers and N-oxides of those compounds, can be used as insecticides and can be prepared in a manner known per se.

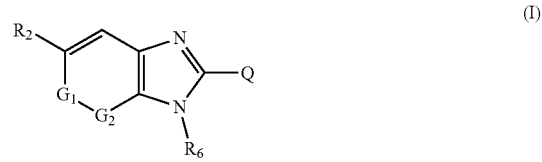

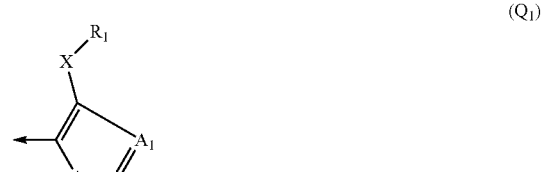

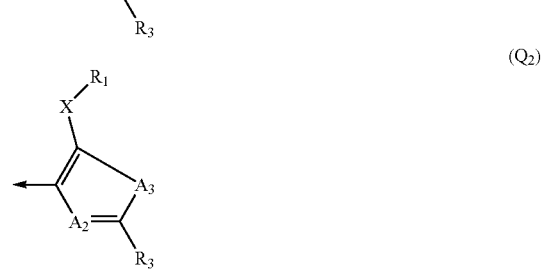

12 Claims, No Drawings

PESTICIDALLY ACTIVE POLYCYCLIC DERIVATIVES WITH SULFUR SUBSTITUTED FIVE MEMBERED RING HETEROCYLES

RELATED APPLICATION INFORMATION

This application is a 371 of International Application No. PCT/EP2016/058526, filed 18 Apr. 2016, which claims priority to EP Patent Application No. 15164953.0 filed 24 Apr. 2015, and EP Patent Application No. 15184067.5 filed 7 Sep. 2015, the contents of which are incorporated herein by reference herein.

The present invention relates to pesticidally active, in particular insecticidally active tetracyclic derivatives containing sulfur substituents, to compositions comprising those compounds, and to their use for controlling animal pests (including arthropods and in particular insects or representatives of the order Acarina).

Heterocyclic compounds with pesticidal action are known and described, for example, in WO 2012/086848, WO 2013/018928, WO 2013/180193, WO 2014/142292 and WO 2015/000715.

There have now been found novel pesticidally active polycyclic derivatives with a sulfur containing cyclic moiety.

The present invention accordingly relates to compounds of formula I,

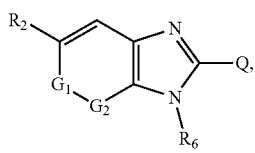

(I)

wherein

Q is $Q_1$ or $Q_2$;

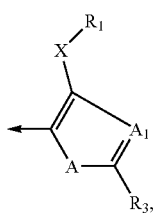

($Q_1$)

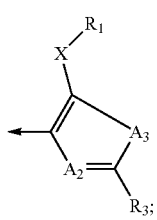

($Q_2$)

A and $A_3$, independently from each other, represents S or O;

$A_1$ and $A_2$, independently from each other, represents N or $CR_7$;

X is S, SO or $SO_2$;

$R_1$ is $C_1$-$C_6$alkyl, $C_2$-$C_6$alkenyl, $C_2$-$C_6$ haloalkenyl, $C_2$-$C_6$alkynyl, $C_1$-$C_6$ haloalkyl, $C_3$-$C_6$cycloalkyl or $C_3$-$C_6$cycloalkyl-$C_1$-$C_4$alkyl; or is $C_3$-$C_6$cycloalkyl mono- or polysubstituted by substituents selected from the group consisting of halogen, cyano and $C_1$-$C_4$alkyl; or is $C_3$-$C_6$cycloalkyl-$C_1$-$C_4$alkyl mono- or polysubstituted by substituents selected from the group consisting of halogen, cyano and $C_1$-$C_4$alkyl;

$R_2$ is hydrogen, halogen, $C_1$-$C_4$ haloalkylsulfanyl, $C_1$-$C_4$ haloalkylsulfinyl, $C_1$-$C_4$ haloalkylsulfonyl, $O(C_1$-$C_4$ haloalkyl), —$SF_5$, —$C(O)C_1$-$C_4$ haloalkyl, cyano, $C_1$-$C_6$ haloalkyl or is $C_1$-$C_6$ haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$alkyl and $C_1$-$C_4$ haloalkyl;

$G_1$ is $NR_4$ and $G_2$ is $C(Y)$; or
$G_1$ is $C(Y)$ and $G_2$ is $NR_5$;
Y is O or S;

$R_3$ is hydrogen, halogen, cyano, nitro, amino, $C_1$-$C_6$alkyl, $C_1$-$C_6$ haloalkyl, $C_3$-$C_6$cycloalkyl-$C_1$-$C_4$alkyl or $C_3$-$C_6$cycloalkyl which can be mono- or polysubstituted by substituents selected from the group consisting of halogen, $C_1$-$C_2$ haloalkyl and cyano; or $R_3$ is $C_2$-$C_6$alkenyl, $C_2$-$C_6$ haloalkenyl, $C_2$-$C_6$alkynyl or $C_2$-$C_6$ haloalkynyl; or $R_3$ is $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, —$C(O)C_1$-$C_4$ haloalkyl, $C_1$-$C_4$alkylsulfanyl, $C_1$-$C_4$alkylsulfinyl or $C_1$-$C_4$alkylsulfonyl; or $R_3$ is $C_1$-$C_4$alkyl mono- or polysubstituted by substituents selected from the group consisting of cyano, phenyl, pyridine and pyrimidine; or $R_3$ is $C_2$-$C_4$alkenyl mono- or polysubstituted by substituents selected from the group consisting of cyano, $C_3$-$C_6$cycloalkyl, phenyl, pyridine and pyrimidine; or $R_3$ is $C_2$-$C_4$alkynyl mono- or polysubstituted by substituents selected from the group consisting of cyano, $C_1$-$C_4$ alkoxy, $C_3$-$C_6$cycloalkyl, phenyl, pyridine and pyrimidine; or $R_3$ is a five- to ten-membered monocyclic or fused bicyclic ring system linked via a carbon atom to the 5-membered heterocycle, said ring system can be aromatic, partially saturated or fully saturated and can contain 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, nitro, amino, hydroxyl, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$ haloalkylsulfanyl, $C_1$-$C_4$ haloalkylsulfinyl, $C_1$-$C_4$ haloalkylsulfonyl and —$C(O)C_1$-$C_4$ haloalkyl; or $R_3$ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, nitro, amino, hydroxyl, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$ haloalkylsulfanyl, $C_1$-$C_4$ haloalkylsulfinyl, $C_1$-$C_4$ haloalkylsulfonyl and —$C(O)C_1$-$C_4$ haloalkyl; and said ring system contains 1, 2 or 3 heteroatoms selected from the group consisting of nitrogen, oxygen and sulphur, where said ring system may not contain more than one oxygen atom and not more than one sulfur atom;

$R_4$ and $R_5$ are, independently from each other, $C_1$-$C_6$alkyl, $C_1$-$C_6$ haloalkyl, or are $C_3$-$C_6$cycloalkyl which can be mono- or poly substituted by $R_7$; or are $C_3$-$C_6$cycloalkyl-$C_1$-$C_4$alkyl which can be mono- or polysubstituted by $R_8$; or $R_4$ and $R_5$ are, independently from each other, $C_2$-$C_6$alkenyl, $C_2$-$C_6$ haloalkenyl, $C_2$-$C_6$alkynyl, $C_2$-$C_6$ haloalkynyl, $C_1$-$C_6$ haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$ haloalkylsulfanyl, $C_1$-$C_6$ haloalkylsulfonyl, $C_1$-$C_6$ haloalkylsulfinyl, amino or hydroxyl; or $R_4$ and $R_5$ are, independently from each other, $C_1$-$C_4$ alkyl substituted by $R_9$; or $R_4$ and $R_5$ are, independently from each other, $C_2$-$C_6$alkenyl substituted by $R_9$; or $R_4$ and $R_5$ are, independently from each other, $C_2$-$C_6$alkynyl substituted by $R_9$; or $R_6$ is hydrogen or $C_1$-$C_6$alkyl which can be mono- or polysubstituted by substituents selected from the group consisting of halogen and $C_1$-$C_2$alkylsulfinyl; or $R_6$ is $C_2$-$C_6$alkenyl, $C_2$-$C_6$alkynyl, $C_1$-$C_4$alkoxy-$C_1$-$C_4$alkyl or $C_3$-$C_6$cycloalkyl;

$R_7$ is hydrogen, cyano, halogen, $C_1$-$C_4$alkyl or $C_1$-$C_4$ haloalkyl;

$R_8$ is cyano, halogen, $C_1$-$C_4$alkyl or $C_1$-$C_2$ haloalkyl;

$R_9$ is cyano, $C_1$-$C_6$alkylsulfanyl, $C_1$-$C_4$alkylsulfonyl, $C_1$-$C_4$alkylsulfinyl, $C_1$-$C_4$ haloalkylsulfanyl, $C_1$-$C_4$ haloalkylsulfonyl, $C_1$-$C_6$ haloalkylsulfinyl, $C_1$-$C_4$alkoxy, $C_1$-$C_4$alkoxy$C_1$-$C_4$alkoxy, $C_3$-$C_6$ cycloalkyl or by phenyl, which itself can be mono- or polysubstituted by substituents selected from the group consisting of halogen, $C_1$-$C_4$alkyl, cyano, $C_1$-$C_4$ haloalkyl and $C_1$-$C_4$alkoxy; or agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

Haloalkylsulfanyl is for example trifluoromethylsulfanyl, 2,2,2-trifluoroethylsulfanyl, and pentafluoroethylsulfanyl.

Haloalkylsulfinyl is for example trifluoromethylsulfinyl, 2,2,2-trifluoroethylsulfinyl, or pentafluoroethylsulfinyl.

Haloalkylsulfonyl is for example trifluoromethylsulfonyl, 2,2,2-trifluoroethylsulfonyl, and pentafluoroethylsulfonyl.

According to the present invention, a five- to ten-membered monocyclic or fused bicyclic ring system which can be aromatic, partially saturated or fully saturated and can contain 1 to 4 hetero atoms selected from the group consisting of nitrogen, oxygen and sulfur, with the proviso that each ring system cannot contain more than 2 oxygen atoms and more than 2 sulfur atoms or a five- to six-membered, aromatic, partially saturated or fully saturated ring system linked via a nitrogen atom to the 5-membered heterocycle, preferably selected from the group consisting of the following heterocyclic groups: pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl; pyranyl; quinazolinyl; isoquinolinyl; indolizinyl; isobenzofuranylnaphthyridinyl; quinoxalinyl; cinnolinyl; phthalazinyl; benzothiazolyl; benzoxazolyl; benzotriazolyl; indazolyl; indolyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3- yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-(1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)-; (furazan-3-yl)-; (2-quinolinyl)-; (3-quinolinyl)-; (4-quinolinyl)-; (5-quinolinyl)-; (6-quinolinyl)-; (3-isoquinolnyl)-; (4-isoquinolnyl)-; (2-quinozolinyl)-; (2-quinoxalinyl)-; (5-quinoxalinyl)-; (pyrido[2,3-b]pyrazin-7-yl)-; (benzoxazol-5-yl)-; (benzothiazol-5-yl)-; (benzo[b]thien-2-yl)- and (benzo[1,2,5]oxadiazol-5-yl)-; indolinyl and tetrahydroquinolynyl.

In preferred compounds of formula I, $R_3$ is selected from the group consisting of I-0 to I-50:

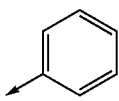
I-0

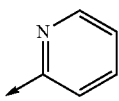
I-1

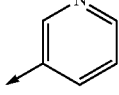
I-2

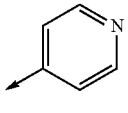
I-3

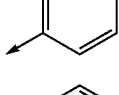
I-4

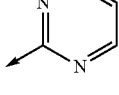
I-5

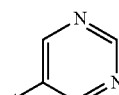
I-6

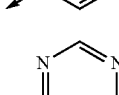
I-7

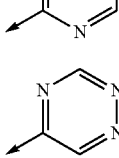
I-8

-continued

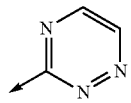
I-9

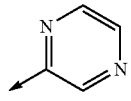
I-10

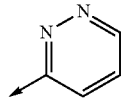
I-11

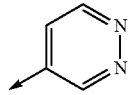
I-12

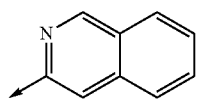
I-13

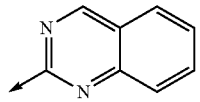
I-14

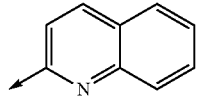
I-15

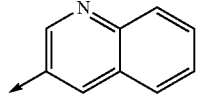
I-16

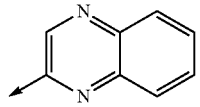
I-17

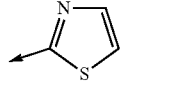
I-18

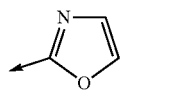
I-19

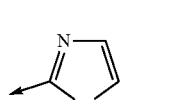
I-20

I-21

I-22

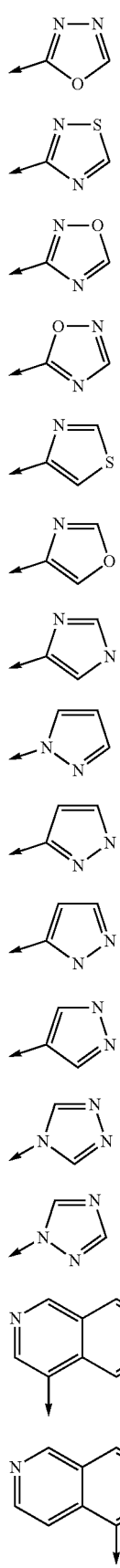
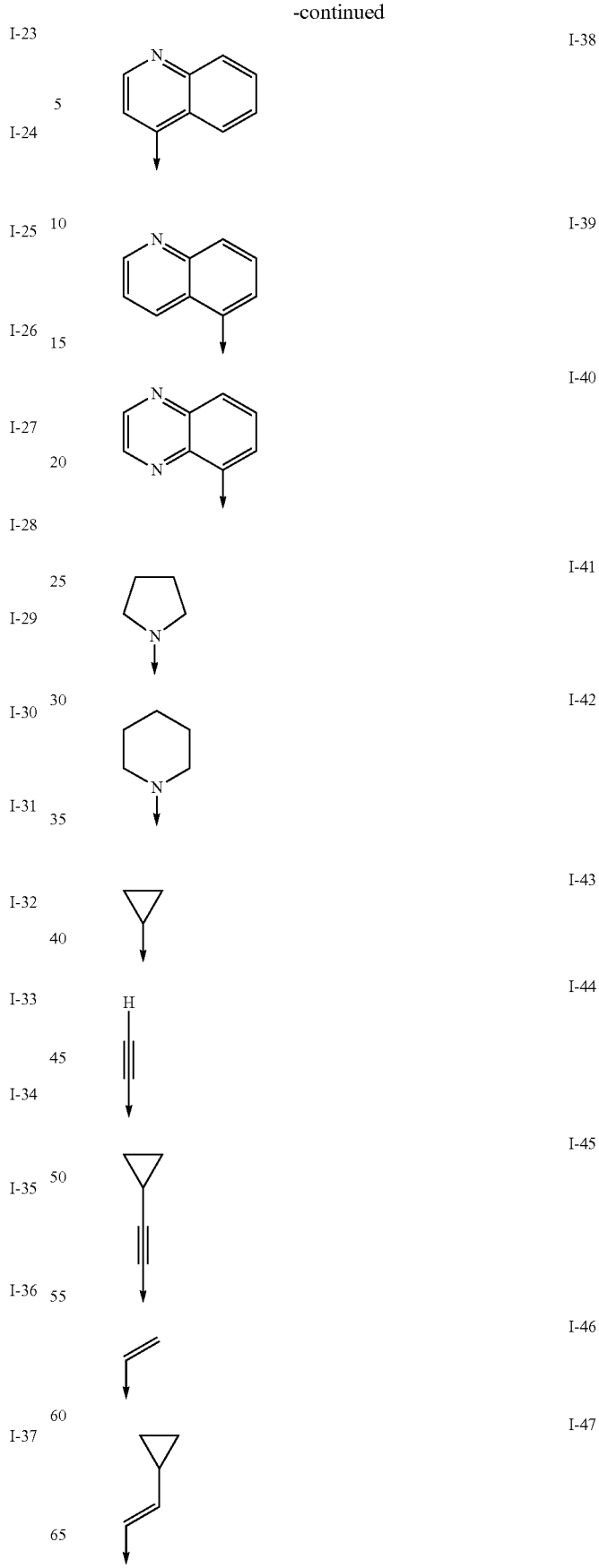

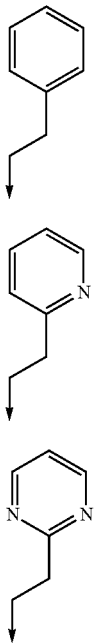

wherein each group I-0 to I-50 is mono- di- or trisubstituted with Rx, wherein each Rx is, independently selected from the group consisting of hydrogen, halogen, cyano, nitro, amino, hydroxyl, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

The compounds of formula I according to the invention also include hydrates which may be formed during the salt formation.

A preferred group of compounds of formula I is represented by the compounds of formula I-1

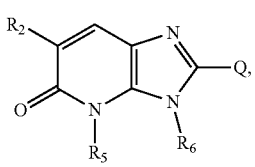

(I-1)

wherein
Q is $Q_1$ or $Q_2$;

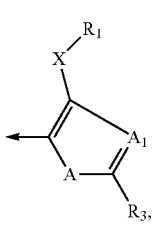

($Q_1$)

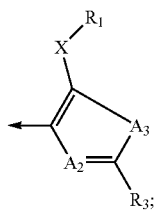

($Q_2$)

wherein the substituents X, A, $A_1$, $A_2$, $A_3$, $R_1$, $R_2$, $R_3$, $R_5$ and $R_6$ are as defined under formula I above.

Embodiment (A1)

Preferred are compounds of formula I-1 above, wherein
$R_1$ is $C_1$-$C_4$alkyl, $C_3$-$C_6$cycloalkyl-$C_1$-$C_4$alkyl or $C_3$-$C_6$cycloalkyl; and
$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or is $C_3$-$C_6$cycloalkyl which can be mono- or polysubstituted by substituents selected from the group consisting of halogen, cyano and $C_1$-$C_4$alkyl.

Embodiment (A2)

Further preferred are compounds of formula I represented by the compounds of formula I-1a

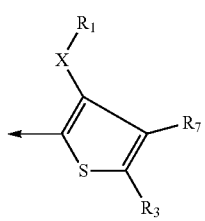

(I-1a)

wherein J is selected from the group consisting of J1, J2 and J3

J1

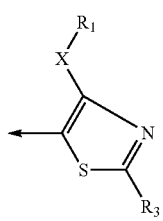

J2

-continued

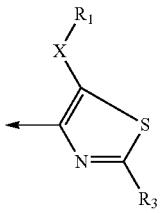

(J3)

R₁ is $C_1$-$C_4$alkyl, $C_3$-$C_6$cycloalkyl-$C_1$-$C_4$alkyl or $C_3$-$C_6$cycloalkyl;

R₂ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or is $C_3$-$C_6$cycloalkyl which can be mono- or polysubstituted by substituents selected from the group consisting of halogen, cyano and $C_1$-$C_4$alkyl and X, R₃, R₅, R₆ and R₇ are as defined under formula I above.

Embodiment (A3)

Further preferred are compounds of formula I-1a

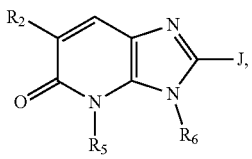

(I-1a)

wherein J is as defined under Embodiment (A2);
R₅ and R₆ are as defined under formula I; R₁ is $C_1$-$C_4$alkyl, $C_3$-$C_6$cycloalkyl-$C_1$-$C_4$alkyl or $C_3$-$C_6$cycloalkyl;
R₂ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or $C_3$-$C_6$cycloalkyl; and
R₃ is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or
R₃ is $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, —C(O)$C_1$-$C_4$ haloalkyl, $C_1$-$C_4$alkylsulfanyl, $C_1$-$C_4$alkylsulfinyl, or $C_1$-$C_4$alkylsulfonyl; or
R₃ is pyrimidine or pyridine which both can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or
R₃ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl and —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

Embodiment (A4)

Further preferred are compounds of formula I-1a

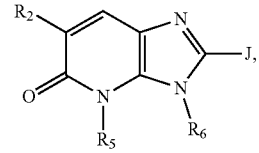

(I-1a)

wherein J is as defined under Embodiment (A2);
R₅ and R₆ are as defined under formula I above;
R₁ is $C_1$-$C_4$alkyl;
R₂ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkyl, cyano or $C_3$-$C_6$cycloalkyl; and
R₃ is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or
R₃ is pyrimidine or pyridine which both can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or
R₃ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl and —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

Embodiment (A5)

Further preferred are compounds of formula I-1a

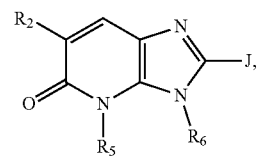

(I-1a)

wherein J is as defined under Embodiment (A2);
R₅ and R₆ are as defined under formula I above; R₁ is $C_1$-$C_4$alkyl;
R₂ is —SCF₃, —S(O)CF₃, —S(O)₂CF₃, CF₃ or CF₂CF₃; and
R₃ is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or
R₃ is pyrimidine or pyridine which both can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or R₃ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, C₁-C₄ haloalkyl, C₁-C₄ haloalkylsulfanyl, C₁-C₄ haloalkylsulfinyl, C₁-C₄ haloalkylsulfonyl and —C(O)C₁-C₄ haloalkyl.

Embodiment (A6)

Further preferred are compounds of formula I-1a

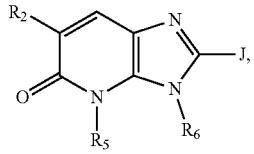

(I-1a)

wherein J is as defined under Embodiment (A2);
R₅ and R₆ are as defined under formula I above;
R₁ is ethyl;
R₂ is —SCF₃, —S(O)CF₃, —S(O)₂CF₃, CF₃ or CF₂CF₃; and
R₃ is phenyl which can be mono- or polysubstituted by substituents selected from the group consisting of halogen, cyano, C₁-C₄alkyl, C₁-C₄ haloalkyl, C₁-C₄ haloalkylsulfanyl, C₁-C₄ haloalkylsulfinyl, and C₁-C₄ haloalkylsulfonyl; or
R₃ is pyrimidine or pyridine which both can be mono- or polysubstituted by substituents selected from the group consisting of halogen, cyano, C₁-C₄alkyl, C₁-C₄ haloalkyl, C₁-C₄ haloalkylsulfanyl, C₁-C₄ haloalkylsulfinyl and C₁-C₄ haloalkylsulfonyl; or
R₃ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, C₁-C₄ haloalkyl, C₁-C₄ haloalkylsulfanyl, C₁-C₄ haloalkylsulfinyl and C₁-C₄ haloalkylsulfonyl;

Embodiment (A7)

Further preferred are compounds of formula I-1a

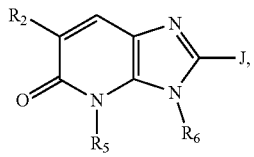

(I-1a)

wherein J is as defined under Embodiment (A2);
R₅ and R₆ are as defined under formula I above;
R₁ is ethyl;
R₂ is —SCF₃, —S(O)CF₃, —S(O)₂CF₃, CF₃ or CF₂CF₃; and
R₃ is phenyl which can be mono- or polysubstituted by substituents selected from the group consisting of fluoro, chloro, bromo, cyano, methyl, trifluoromethyl, CF₃S—, CF₃S(O)—, and CF₃S(O)₂—; or
R₃ is pyrimidine or pyridine which both can be mono- or polysubstituted by substituents selected from the group consisting of fluoro, chloro, bromo, cyano, methyl, trifluoromethyl, CF₃S—, CF₃S(O)—, and CF₃S(O)₂—; or
R₃ is a five membered, aromatic, partially saturated or fully saturated ring system linked via a nitrogen atom to the 5-membered heterocycle, said ring system can be mono- or polysubstituted by substituents selected from the group consisting of fluoro, chloro, bromo, cyano, methyl, trifluoromethyl, CF₃S—, CF₃S(O)—, and CF₃S(O)₂—;

Embodiment (A8)

Further preferred are compounds of formula I-1a

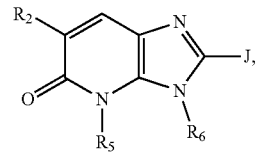

(I-1a)

wherein J is as defined under Embodiment (A2);
R₅ and R₆ are as defined under formula I above;
R₁ is ethyl;
R₂ is —SCF₃, —S(O)CF₃, —S(O)₂CF₃ or CF₃; and
R₃ is phenyl which can be mono- or polysubstituted by substituents selected from the group consisting of fluoro, chloro, bromo, cyano and trifluoromethyl; or
R₃ is pyrimidine or pyridine which both can be mono- or polysubstituted by substituents selected from the group consisting of fluoro, chloro, bromo, cyano and trifluoromethyl; or
R₃ is a pyrazol linked via a nitrogen atom to the 5-membered heterocycle, said ring system can be mono- or polysubstituted by substituents selected from the group consisting of fluoro, chloro, bromo, cyano and trifluoromethyl.

In all of the preferred embodiments A1 to A8 above, the compounds of formula I above and the preferred group of compounds of formula I represented by the compounds of formula I-1 above, X is preferably S or SO₂;

In all of the preferred embodiments A1 to A8, the compounds of formula I above and the preferred group of compounds of formula I represented by the compounds of formula I-1 above, R₆ is preferably methyl. In all of the preferred embodiments A1 to A8 above, the compounds of formula I above and the preferred group of compounds of formula I represented by the compounds of formula I-1 above, R₅ is preferably methyl or ethyl.

A further preferred group of compounds of formula I is represented by the compounds of formula I-2

(I-2)

wherein
Q is Q₁ or Q₂;

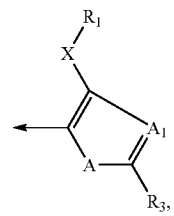

(Q₁)

-continued

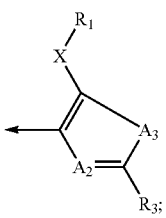

(Q2)

wherein the substituents X, A, $A_1$, $A_2$, $A_3$, $R_1$, $R_2$, $R_4$, $R_3$ and $R_6$ are as defined under formula I above.

Embodiment (B1)

Preferred are compounds of formula I-2 above, wherein
$R_1$ is $C_1$-$C_4$alkyl, $C_3$-$C_6$cycloalkyl-$C_1$-$C_4$alkyl or $C_3$-$C_6$cycloalkyl; and
$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or is $C_3$-$C_6$cycloalkyl which can be mono- or polysubstituted by substituents selected from the group consisting of halogen, cyano and $C_1$-$C_4$alkyl.

Embodiment (B2)

Further preferred are compounds of formula I-2a

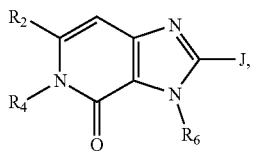

(I-2a)

wherein J is selected from the group consisting of

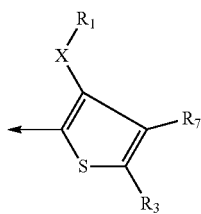

J1

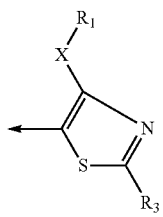

J2

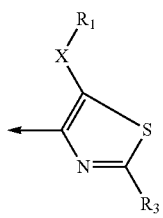

J3

$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or is $C_3$-$C_6$cycloalkyl which can be mono- or polysubstituted by substituents selected from the group consisting of halogen, cyano and $C_1$-$C_4$alkyl;
and X, $R_3$, $R_4$ $R_6$ and $R_7$ are as defined under formula I above.

Embodiment (B3)

Further preferred are compounds of formula I-2a

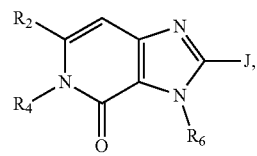

(I-2a)

wherein J is as defined under Embodiment (B2);
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or $C_3$-$C_6$cycloalkyl;
$R_4$ and $R_6$ are as defined under formula I above; and
$R_3$ is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or
$R_3$ is $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, —C(O)$C_1$-$C_4$ haloalkyl, $C_1$-$C_4$alkylsulfanyl, $C_1$-$C_4$alkylsulfinyl, or $C_1$-$C_4$alkylsulfonyl; or
$R_3$ is pyrimidine or pyridine which both can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or
$R_3$ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl and —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

Embodiment (B4)

Further preferred are compounds of formula I-2a

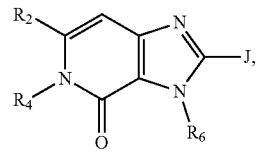

(I-2a)

wherein J is as defined under Embodiment (B2);
$R_1$ is $C_1$-$C_4$alkyl;
$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkyl, cyano or $C_3$-$C_6$cycloalkyl;
$R_4$ and $R_6$ are as defined under formula I above; and $R_3$ is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or $R_3$ is pyrimidine or pyridine which both can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or $R_3$ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl and —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

Embodiment (B5)

Further preferred are compounds of formula I-2a (I-2a)

wherein J is as defined under Embodiment (B2);
$R_1$ is $C_1$-$C_4$alkyl;
$R_2$ is —SCF$_3$, —S(O)CF$_3$, —S(O)$_2$CF$_3$, CF$_3$ or CF$_2$CF$_3$;
$R_4$ and $R_6$ are as defined under formula I above; and $R_3$ is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl; $C_1$-$C_4$ haloalkylsulfonyl and —C(O)$C_1$-$C_4$ haloalkyl; or $R_3$ is pyrimidine or pyridine which both can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl; $C_1$-$C_4$ haloalkylsulfinyl, $C_1$-$C_4$ haloalkylsulfonyl and —C(O)$C_1$-$C_4$ haloalkyl; or $R_3$ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, $C_1$-$C_4$ haloalkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

Embodiment (B6)

Further preferred are compounds of formula I-2a (I-2a)

wherein J is as defined under Embodiment (B2);

$R_1$ is ethyl;
$R_2$ is —SCF$_3$, —S(O)CF$_3$, —S(O)$_2$CF$_3$, CF$_3$ or CF$_2$CF$_3$;
$R_4$ and $R_6$ are as defined under formula I above and $R_3$ is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkylsulfanyl, $C_1$-$C_4$ haloalkylsulfinyl, and $C_1$-$C_4$ haloalkylsulfonyl; or $R_3$ is pyrimidine or pyridine which both can be mono- or polysubstituted by substituents selected from the group consisting of halogen, cyano, $C_1$-$C_4$alkyl, $C_1$-$C_4$ haloalkyl, $C_1$-$C_4$ haloalkylsulfanyl, $C_1$-$C_4$ haloalkylsulfinyl and $C_1$-$C_4$ haloalkylsulfonyl; or $R_3$ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, $C_1$-$C_4$ haloalkyl, $C_1$-$C_4$ haloalkylsulfanyl, $C_1$-$C_4$ haloalkylsulfinyl and $C_1$-$C_4$ haloalkylsulfonyl.

Embodiment (B7)

Further preferred are compounds of formula I-2a (I-2a)

wherein J is as defined under Embodiment (B2);
$R_1$ is ethyl;
$R_2$ is —SCF$_3$, —S(O)CF$_3$, —S(O)$_2$CF$_3$, CF$_3$ or CF$_2$CF$_3$;
$R_4$ and $R_6$ is as defined under formula I above and $R_3$ is phenyl which can be mono- or polysubstituted by substituents selected from the group consisting of fluoro, chloro, bromo, cyano, methyl, trifluoromethyl, CF$_3$S—, CF$_3$S(O)—, and CF$_3$S(O)$_2$—; or $R_3$ is pyrimidine or pyridine which both can be mono- or polysubstituted by substituents selected from the group consisting of fluoro, chloro, bromo, cyano, methyl, trifluoromethyl, CF$_3$S—, CF$_3$S(O)—, and CF$_3$S(O)$_2$—; or $R_3$ is a five membered, aromatic, partially saturated or fully saturated ring system linked via a nitrogen atom to the 5-membered heterocycle, said ring system can be mono- or polysubstituted by substituents selected from the group consisting of fluoro, chloro, bromo, cyano, methyl, trifluoromethyl, CF$_3$S—, CF$_3$S(O)— and CF$_3$S(O)$_2$—.

Embodiment (B8)

Further preferred are compounds of formula I-2a (I-2a)

wherein J is as defined under Embodiment (B2);
$R_1$ is ethyl;
$R_2$ is —SCF$_3$, —S(O)CF$_3$, —S(O)$_2$CF$_3$ or CF$_3$;
$R_4$ and $R_6$ are as defined under formula I above and $R_3$ is phenyl which can be mono- or polysubstituted by substituents selected from the group consisting of fluoro, chloro, bromo, cyano, trifluoromethyl; or $R_3$ is pyrimidine or pyridine which both can be mono- or polysubstituted by substituents selected from the group consisting of fluoro, chloro, bromo, cyano and trifluoromethyl; or $R_3$ is a pyrazol linked via a nitrogen atom to the 5-membered heterocycle, said ring system can be mono- or polysubstituted by substituents selected from the group consisting of fluoro, chloro, bromo, cyano and trifluoromethyl.

In all of the preferred embodiments B1 to B8 above, the compounds of formula I above and the preferred group of compounds of formula I represented by the compounds of formula I-1 above, X is preferably S or $SO_2$;

In all of the preferred embodiments B1 to B8, the compounds of formula I above and the preferred group of compounds of formula I represented by the compounds of formula I-1 above, $R_6$ is preferably methyl.

In all of the preferred embodiments B1 to B8 above, the compounds of formula I above and the preferred group of compounds of formula I represented by the compounds of formula I-1 above, $R_4$ is preferably methyl or ethyl.

In all of the preferred embodiments A2-A8 and B2-B8, J is preferably $J_1$, $J_2$ and $J_3$, in particular J is $J_1$.

Further preferred are compounds of formula I-2a

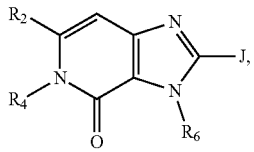

(I-2a)

wherein J is $J_1$ or $J_3$

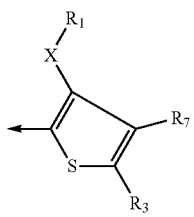

J1

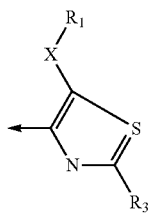

J3

$R_1$ is ethyl;
X is S, S(O) or $SO_2$;
$R_2$ is $CF_3$;
$R_4$ is methyl or ethyl;
$R_6$ is methyl;
$R_3$ is halogen; or
$R_3$ is $C_2$-$C_4$alkenyl or $C_2$-$C_4$alkenyl substituted by phenyl; or
$R_3$ is $C_2$-$C_4$alkynyl or $C_2$-$C_4$alkynyl mono- or polysubstituted by $C_1$-$C_4$alkoxy; or $R_3$ is a ring system selected from phenyl, pyrimidinyl, pyridyl, thienyl, imidazolyl, pyrazolyl and thiazolyl; said ring system can be mono- or polysubstituted by substituents selected from the group consisting of halogen, $C_1$-$C_2$ haloalkyl, cyano, $C_1$-$C_2$ haloalkoxy, $C_1$-$C_2$alkoxy, $C_1$-$C_2$alkylsulfinyl and $C_1$-$C_2$alkyl.

The process according to the invention for preparing compounds of formula (I) is carried out by methods known to those skilled in the art, or described for example in WO 2009/131237, WO 2011/043404, WO 2011/040629, WO 2010/125985, WO 2012/086848, WO 2013/018928, WO 2013/191113, WO 2013/180193, WO 2013/180194 and WO 2015/000715, and involves reaction of a compound of formula II,

(II)

wherein Q is $Q_{1a}$ or $Q_{2a}$

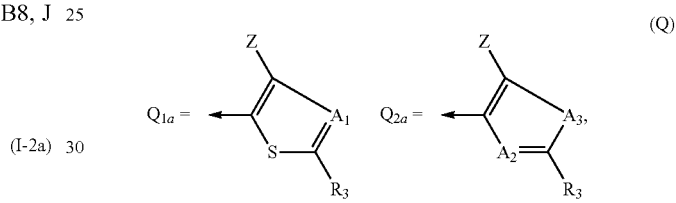

(Q)

wherein Z is X—$R_1$ or a leaving group, for example a halogen, and wherein X, $R_1$, $R_3$, A, $A_1$, $A_2$ and $A_3$ are as described under formula I above, and wherein the arrow in the radical Q shows the point of attachment to the carbon atom of the carboxyl group in the compound of formula II, with a compound of formula III,

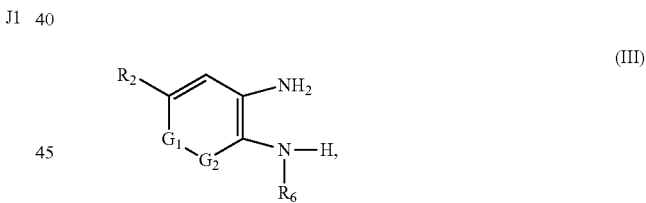

(III)

wherein $R_6$, $R_2$, $G_1$ and $G_2$ are as described under formula I above, in the presence of a dehydrating agent, such as for example polyphosphoric acid at temperature between 150° C. to 250° C., to yield compounds of formula Ia, wherein the substituents are as described above and under formula I. Such processes are well known and have been described for example in WO 2008/128968 or WO 2006/003440. The process is summarized in scheme 1 for compounds of formula Ia:

Scheme 1

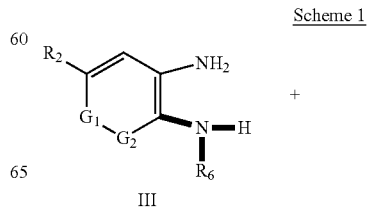

III

-continued

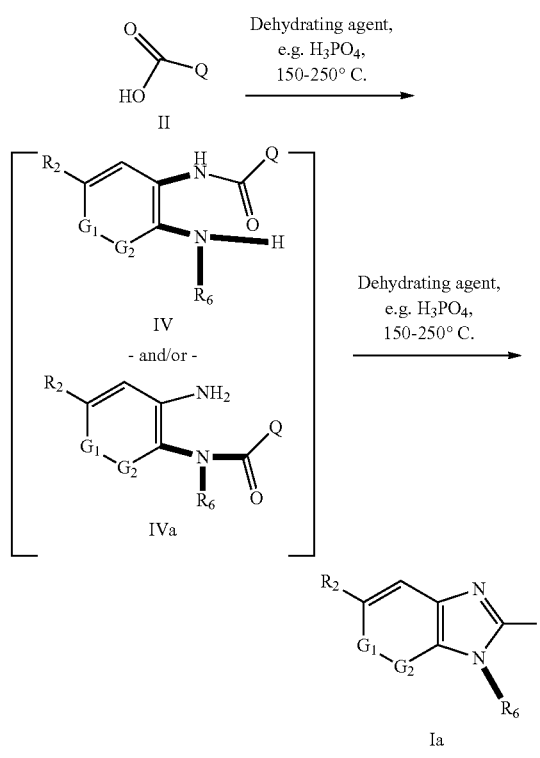

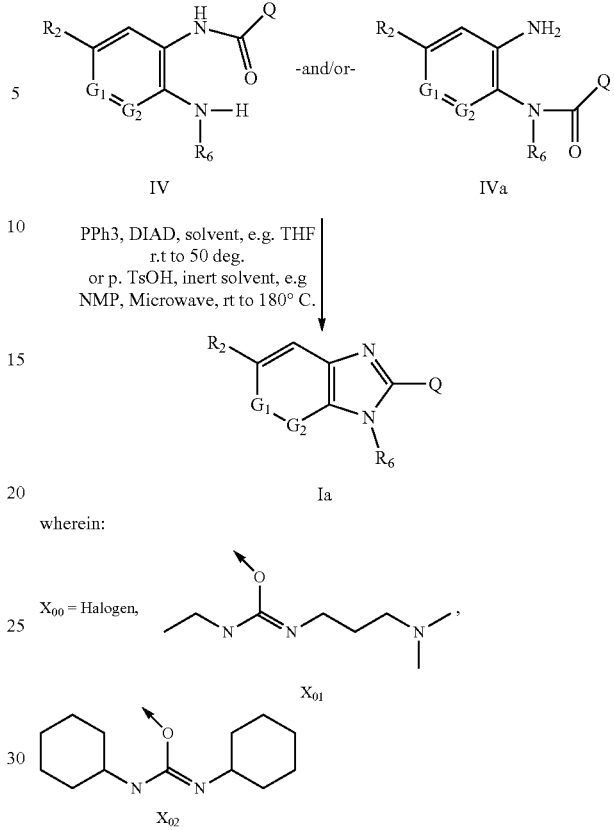

wherein:

$X_{00}$ = Halogen,

As can be seen in scheme 1, the formation of compounds of formula Ia occurs through the intermediacy of a compound of formula IV (and/or its position isomer IVa). Intermediate IV or intermediate IVa may form as a pure entity, or intermediates IV and IVa may arise as a mixture of regioisomeric acylation products. It is in many cases advantageous to thus prepare compounds of formula (I) through such intermediates IV/IVa, which may be isolated and optionally purified. This is illustrated for compounds of formula Ia in scheme 2:

Scheme 2

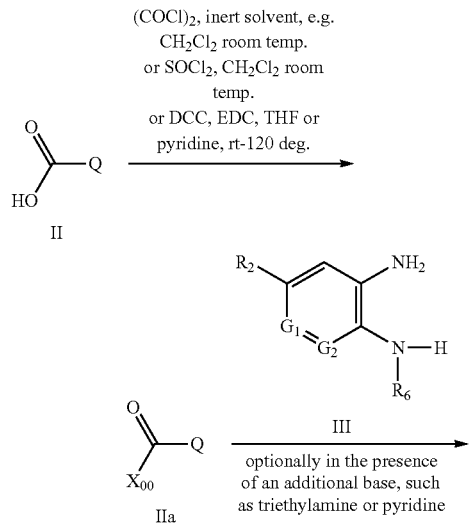

Compounds of the formula IV and/or IVa (or a mixture thereof), or a salt thereof, wherein Q is as defined above, and wherein $R_6$, $R_2$, $G_1$ and $G_2$ are as described under formula I above, may be prepared by i) activation of compound of formula II, wherein Q is as defined above, by methods known to those skilled in the art and described in, for example, Tetrahedron, 2005, 61 (46), 10827-10852, to form an activated species IIa, wherein Q is as defined above and wherein $X_{00}$ is halogen, preferably chlorine. For example, compounds IIa where $X_{00}$ is halogen, preferably chlorine, are formed by treatment of II with, for example, oxallyl chloride (COCl)$_2$ or thionyl chloride SOCl$_2$ in the presence of catalytic quantities of N,N-dimethylformamide DMF in inert solvents such as methylene chloride CH$_2$Cl$_2$ or tetrahydrofuran THF at temperatures between 20 to 100° C., preferably 25° C. Alternatively, treatment of compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_6$, $R_2$, $G_1$ and $G_2$ are as described under formula I above, optionally in the presence of a base, such as triethylamine or pyridine, in an inert solvents such as dichloromethane, tetrahydrofuran, dioxane or toluene, at temperatures between 0 and 80° C., to form the compounds of formula IV and/or IVa (or a mixture thereof).

Compounds of formula IV and/or IVa (or a mixture thereof) may further be converted into compounds of formula Ia, wherein Q is as defined above, and wherein $R_6$, $R_2$, $G_1$ and $G_2$ are as described under formula I above, by dehydration, e.g. by heating the compounds IV and/or IVa (or a mixture thereof) in the presence of an acid catalyst, such as for example methane sulfonic acid, or para-toluene sulfonic acid TsOH, in an inert solvent such as N-methyl pyrrolidine (NMP) at temperatures between 25-180° C., preferably 100-170° C., optionally under microwave conditions. Such processes have been described previously, for example, in WO 2010/125985.

Compounds of formula Ia, wherein Q is as defined above, and wherein Z is a leaving group, for example halogen, preferably fluorine or chlorine, and wherein $R_6$, $R_2$, $G_1$ and $G_2$ are as described under formula I above, can be reacted with compounds of formula V

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, wherein $R_1$ is as described under formula I above, and in which A, $A_1$, $A_2$, $A_3$, $R_2$, $R_3$, $R_6$, $G_1$ and $G_2$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO2013/018928. Examples of salts of the compound of formula V include compounds of the formula Va

wherein $R_1$ is as defined above and wherein M is, for example, sodium or potassium. This is illustrated for compounds of formula Ib with $Q_{1a}$ in scheme 3 and with $Q_{2a}$ in scheme 3a:

Scheme 3

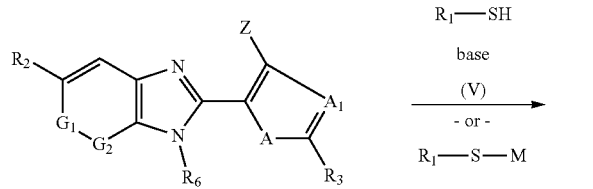

Ia, wherein Z is a leaving group (for example a halogen)

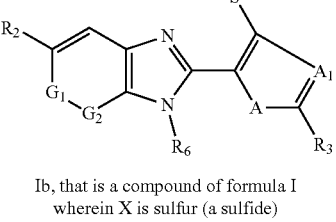

Ib, that is a compound of formula I wherein X is sulfur (a sulfide)

Scheme 3a

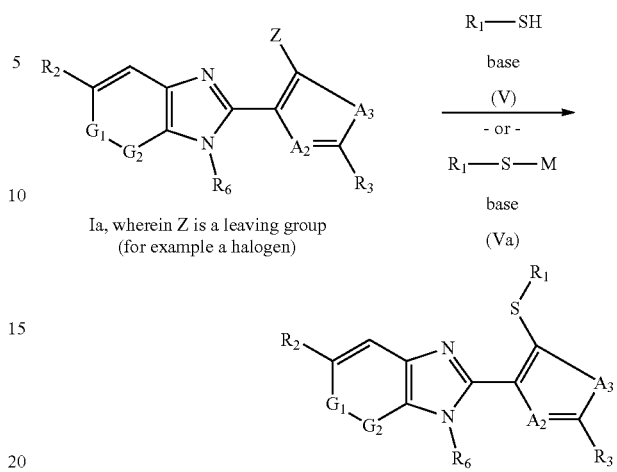

Ia, wherein Z is a leaving group (for example a halogen)

Ic, that is a compound of formula I wherein X is sulfur (a sulfide)

Alternatively, this reaction can be carried out in the presence of a palladium catalyst, such as tris(dibenzylideneacetone)dipalladium(0), in the presence of a phosphor ligand, such as xantphos, in an inert solvent, for example, xylene at temperatures between 100-160° C., preferably 140° C., as described by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of of the sulfide compounds Ib to produce the sulfone compounds I (wherein X=$SO_2$). Such oxidation reactions are disclosed, for example, in WO 2013/018928. This reaction could be done on other intermediates of the synthesis such as compounds of formula II, IIda and IIdb wherein X is S.

Compounds of formula III, may be made by methods known to a person skilled in the art. For example, Compounds of formula III, may be made by the following synthesis sequence.

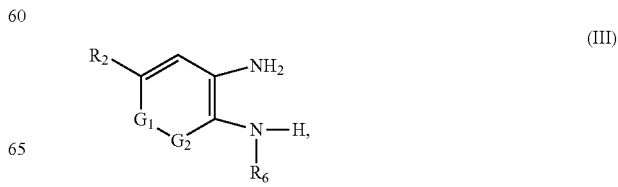

The sequence to prepare compounds of formula IIIa wherein $R_2$, $R_6$ and $R_4$ are as described under formula I above, from compounds of formula VIII, may involve i. alkylation of compound VIII with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula VII, wherein $R_2$, $R_6$ and $R_4$ are as described under formula I above; Other alternatives well known by a person skilled in the art such as aminoreduction via imine formation could be use too (e.g. see Comprehensive Organic Transformations. A Guide to Functional Group Preparations (1989) Larock, R. C. (Publisher: VCH Weinheim, Fed. Rep. Ger.) p 421) ii. a reaction of nitration of compound VII in classical conditions, for example, see for example, Advanced Organic Chemistry: Reactions, Mechanisms, and Structure, Fourth Edition by Jerry March, 1992 (Publisher Wiley New York, N.Y.) p 523-525; and finally iii. a reaction of reduction of compound VI in classical conditions, for example, see for example, Advanced Organic Chemistry: Reactions, Mechanisms, and Structure, Fourth Edition by Jerry March, 1992 (Publisher Wiley New York, N.Y.) p 1216-1217. See scheme 4.

Scheme 4

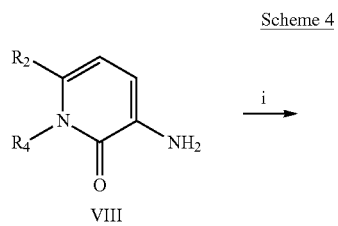

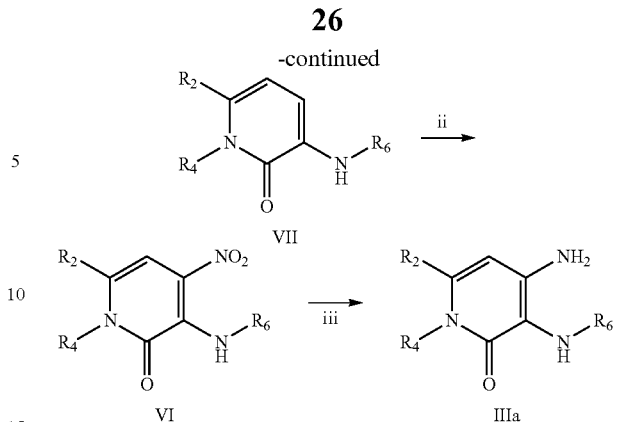

Compounds of formula VIII may be made by methods known to a person skilled in the art, for example Synthesis 2005, No. 8, pp 1269-1278 and Synthesis 2011, No. 7, pp 1149-1156.

Compounds of formula I-2a (illustrated by I-2a1 and I-2a2), wherein Z is X—$R_1$ or a leaving group, for example halogen, and wherein X, $R_1$, $R_4$, $R_6$, A, $A_1$, $A_2$, $A_3$ and $R_3$ are as described under formula I above, may be prepared by reaction between compounds of formula II respectively IIa, wherein Z is X—$R_1$ or a leaving group, for example halogen, and wherein X, $R_1$, A, $A_1$, $A_2$ and $A_3$ are as described under formula I above, and in which $X_{00}$ is as described above, and compounds of formula IIIa, wherein $R_6$ and $R_2$ are as described under formula I above, under similar conditions as for the preparation of compounds of formula Ia from compounds of formula II/IIa and III described above (see scheme 1 and 2). This is illustrated for compounds of formula IIIa in scheme 5:

Scheme 5

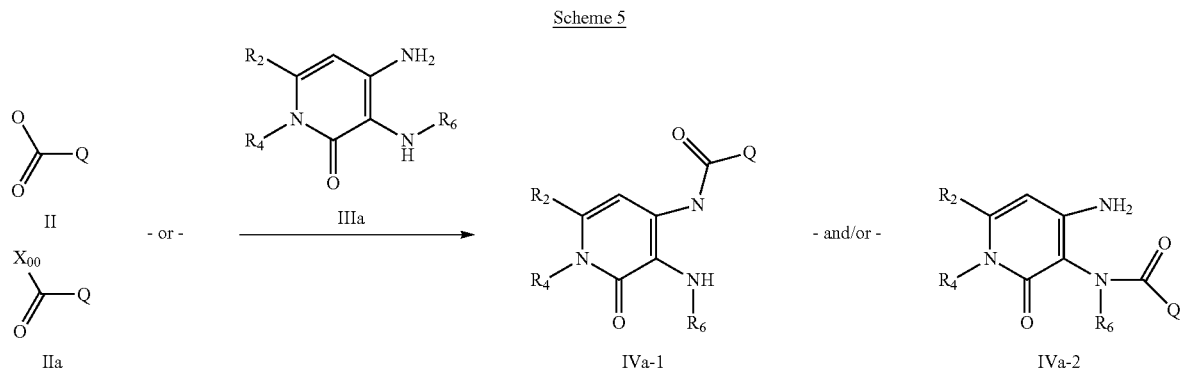

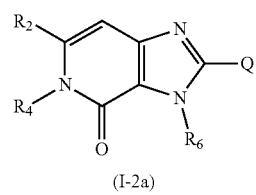

(I-2a)

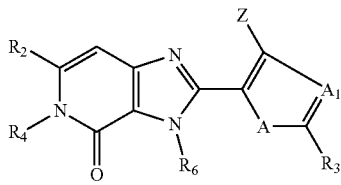

(I-2a1)

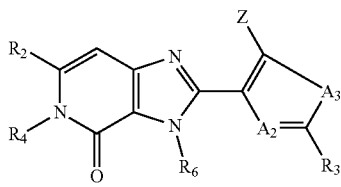

(I-2a2)

Alternatively, the sequence to prepare compounds of formula IIIb wherein $R_2$, $R_5$ and $R_6$ are as described under formula I above, from compounds of formula XII, may involve i. alkylation of compound XII with $R_5$—$X_{LG}$, wherein $R_5$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula XI, wherein $R_6$, $R_5$ and $R_2$ are as described under formula I above; ii. a reaction of Vicarious nucleophilic substitution (VNS) reaction of compound XI in classical conditions, for example, J. Org. Chem., Vol. 61, No. 2, 1996 p 442; iii. alkylation of compound X with $R_6$—XLG, wherein $R_6$ is as described under formula I above and wherein XLG is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IX, wherein $R_6$, $R_5$ and $R_2$ are as described under formula I above; Other alternatives well known by a person skilled in the art such as aminoreduction via imine formation could be use too (e.g. see Comprehensive Organic Transformations. A Guide to Functional Group Preparations (1989) Larock, R. C. (Publisher: VCH Weinheim, Fed. Rep. Ger.) p 421). And finally iv. a reaction of reduction of compound IX in classical conditions, for example, see for example, Advanced Organic Chemistry: Reactions, Mechanisms, and Structure, Fourth Edition by Jerry March, 1992 (Publisher Wiley New York, N.Y.) p 1216-1217. See scheme 6.

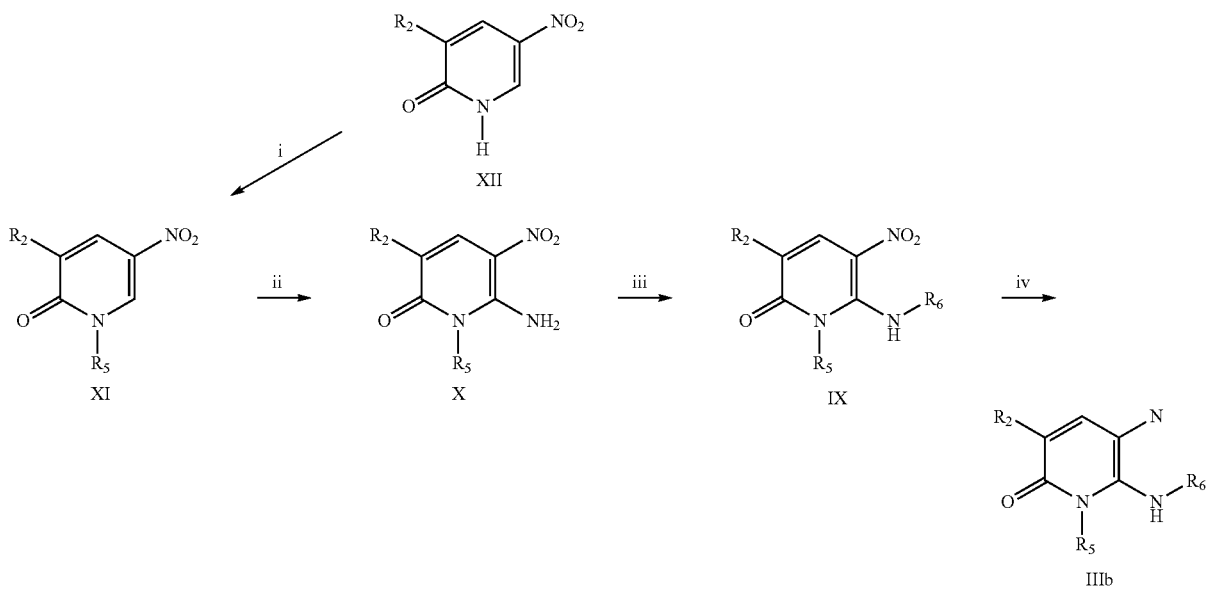

Compounds of formula XII are commercially available or may be made by methods known to a person skilled in the art.

Compounds of formula I-1a (Illustrated by I-1a1 and I-1ab), wherein Z is X—$R_1$ or a leaving group, for example halogen, and wherein Q, X, $R_1$, $R_2$, $R_5$, $R_6$, A, $A_1$, $A_2$ and $A_3$ are as described under formula I above, may be prepared by reaction between compounds of formula II respectively IIa, wherein Z is X—$R_1$ or a leaving group, for example halogen, and wherein X, $R_1$, A, $A_1$, $A_2$ and $A_3$ are as described under formula I above, and in which $X_{00}$ is as described above, and compounds of formula IIIb, wherein $R_5$, $R_6$ and $R_2$ are as described under formula I above, under similar conditions as for the preparation of compounds of formula Ia from compounds of formula II/IIa and III described above (see scheme 1 and 2). This is illustrated in scheme 7:

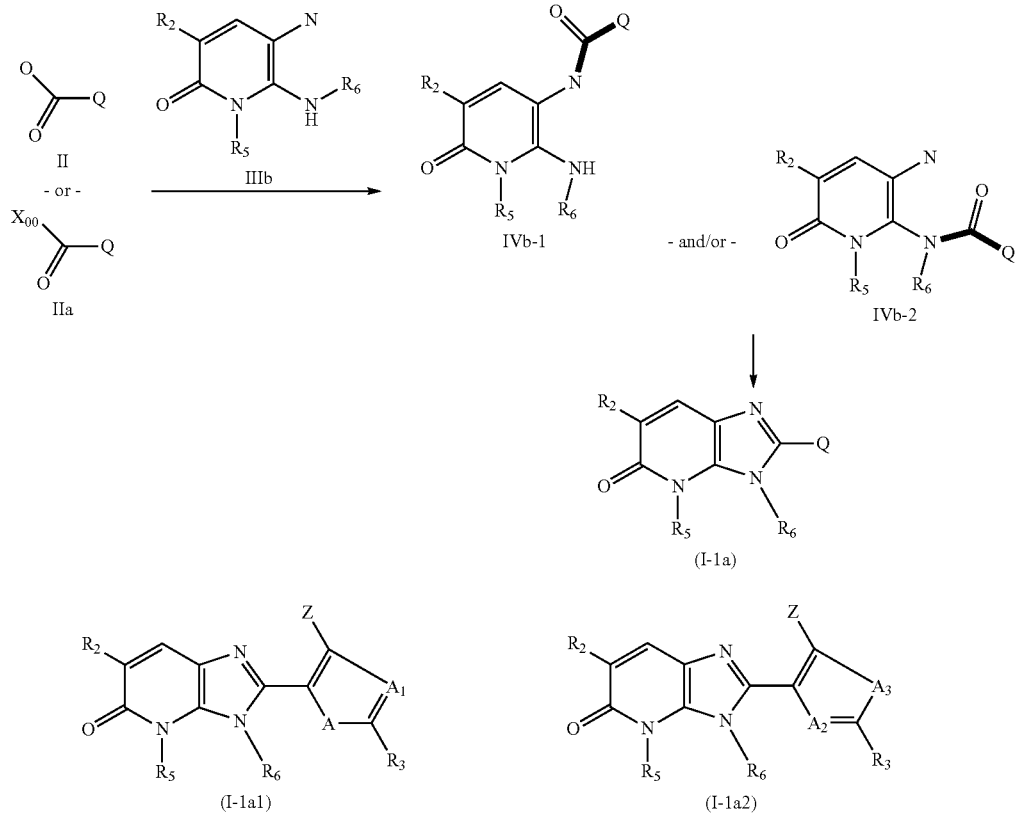

Compounds of formula II,

II wherein Q is $Q_{1a}$ or $Q_{2a}$

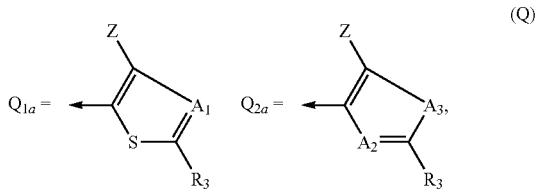

(Q)

wherein Z is X—$R_1$ or a leaving group such as, for example halogen or nitro, and wherein X, $R_1$, $R_3$, A, $A_1$, $A_2$ and $A_3$ are as described under formula I above, may be either known, commercially available or may be made by methods known to a person skilled in the art.

Compounds of formula IIca or IIcb, wherein $R_3$, A, $A_1$, $A_2$ and $A_3$ are as described under formula I above, and wherein Z is a leaving group, for example halogen, preferably fluorine, chlorine, and wherein R is alkyl or hydrogen can be reacted with compounds of formula V $$R_1\text{—SH} \qquad (V),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula IIda or IIdb, wherein R is alkyl or hydrogen and $R_1$, A, $A_1$, $A_2$, $A_3$ and $R_3$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula V include compounds of the formula Va $$R_1\text{—S-M} \qquad (Va),$$

wherein $R_1$ is as defined in compound formula I above and wherein M is, for example, sodium or potassium. This is illustrated for compounds of formula IIda and IIdb wherein X is S, in scheme 8a for Q is $Q_{1a}$ and scheme 8b for Q is $Q_{2a}$.

Scheme 8a

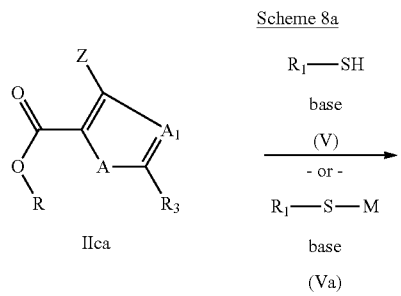

Scheme 8b

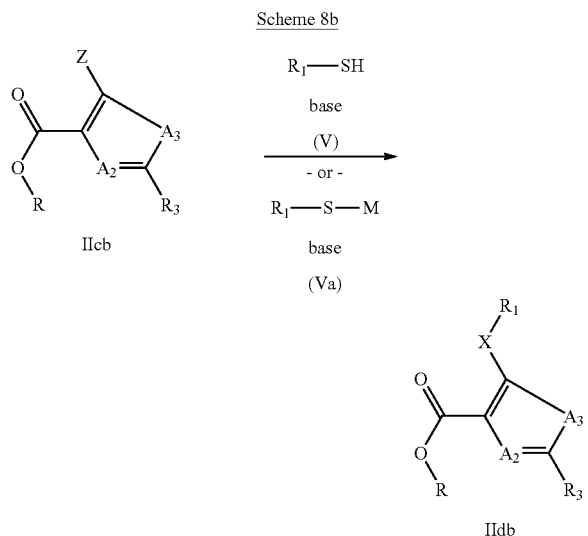

Compound of formula (II), wherein Q is is as described under formula I above, may be prepared by reaction of a compound of formula (IIda or IIdb), wherein X, $R_1$, $R_3$, A, $A_1$, $A_2$ and $A_3$ are as described under formula I above and wherein R is alkyl via hydrolysis. For instance, in the case where R is methyl or ethyl, the hydrolysis can be done with water and a base, such as potassium hydroxide or lithium hydroxide, in the absence or in the presence of a solvent, such as, for instance, tetrahydrofuran or methanol. In the case where R is, for example, tert-butyl, the hydrolysis is done in the presence of acid, such as trifluoroacetic acid or hydrochloric acid. The reaction is carried out at a temperature of from −120° C. to +130° C., preferably from −100° C. to 100° C. This is illustrated in scheme 9.

Scheme 9

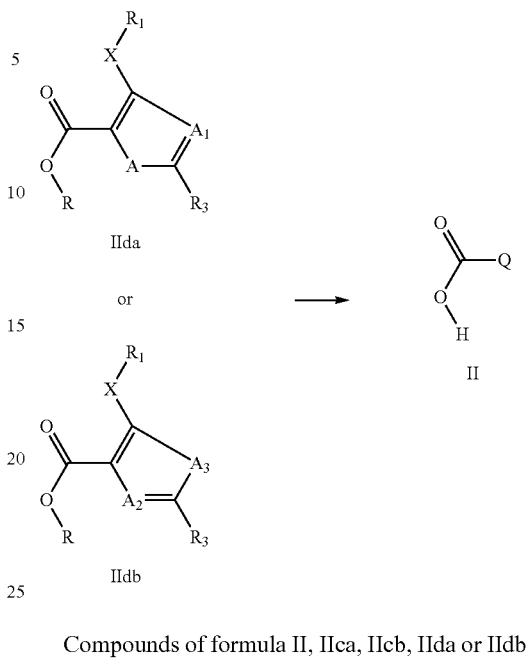

Compounds of formula II, IIca, IIcb, IIda or IIdb, wherein $R_3$ is, for example alkenyl, alkynyl, aromatic or heteroaromatic, can be prepared (scheme 10a for $Q_1$ and $Q_{1a}$, scheme 10b for $Q_2$ and $Q_{2a}$) by reacting compounds of formula II, IIca, IIcb, IIda or IIdb, wherein R'$_3$ is a leaving group like, for example, chlorine, bromine or iodine, or an aryl- or alkylsulfonate such as trifluoromethanesulfonate, or any other similar leaving group with compounds of formula XIII, wherein Y can be a boron-derived functional group, as for example $B(OH)_2$ or $B(ORa)_2$ wherein Ra can be a $C_1$-$C_4$alkyl group or the two groups ORa can form together with the boron atom a five membered ring, as for example a pinacol boronic ester. The reaction can be catalyzed by a palladium based catalyst, for example tetrakis(triphenylphosphine)-palladium, in presence of a base, like sodium carbonate, in a solvent or a solvent mixture, like, for example a mixture of 1,2-dimethoxyethane and water, preferably under inert atmosphere. The reaction temperature can preferentially range from room temperature to the boiling point of the reaction mixture. This type of reactions are well known to a person skilled in the art and call Suzuki or Suzuki-Miyaura reactions (see for example, Kurti, Laszlo; Czako, Barbara; (Editors) Strategic Applications of Named Reactions in Organic Synthesis (2005) p 448. Alternatively, Y can be a tin-derived functional group, as for example $Bu_3Sn$ and the reaction can be catalyzed by metal catalyst such, for example a palladium based catalyst, for example tetrakis(triphenylphosphine)-palladium, in a solvent or a solvent mixture, like, for example toluene, preferably under inert atmosphere. This type of reactions are well to a person skilled in the art and call Stille cross coupling reactions (see for example, Kurti, Laszlo; Czako, Barbara; (Editors) Strategic Applications of Named Reactions in Organic Synthesis (2005) p 438.

Compounds of formula XIII are Y—$R_3$ wherein $R_3$ is, for example alkenyl, alkynyl, aromatic or heteroaromatic and are commercially available or may be made by methods known to a person skilled in the art.
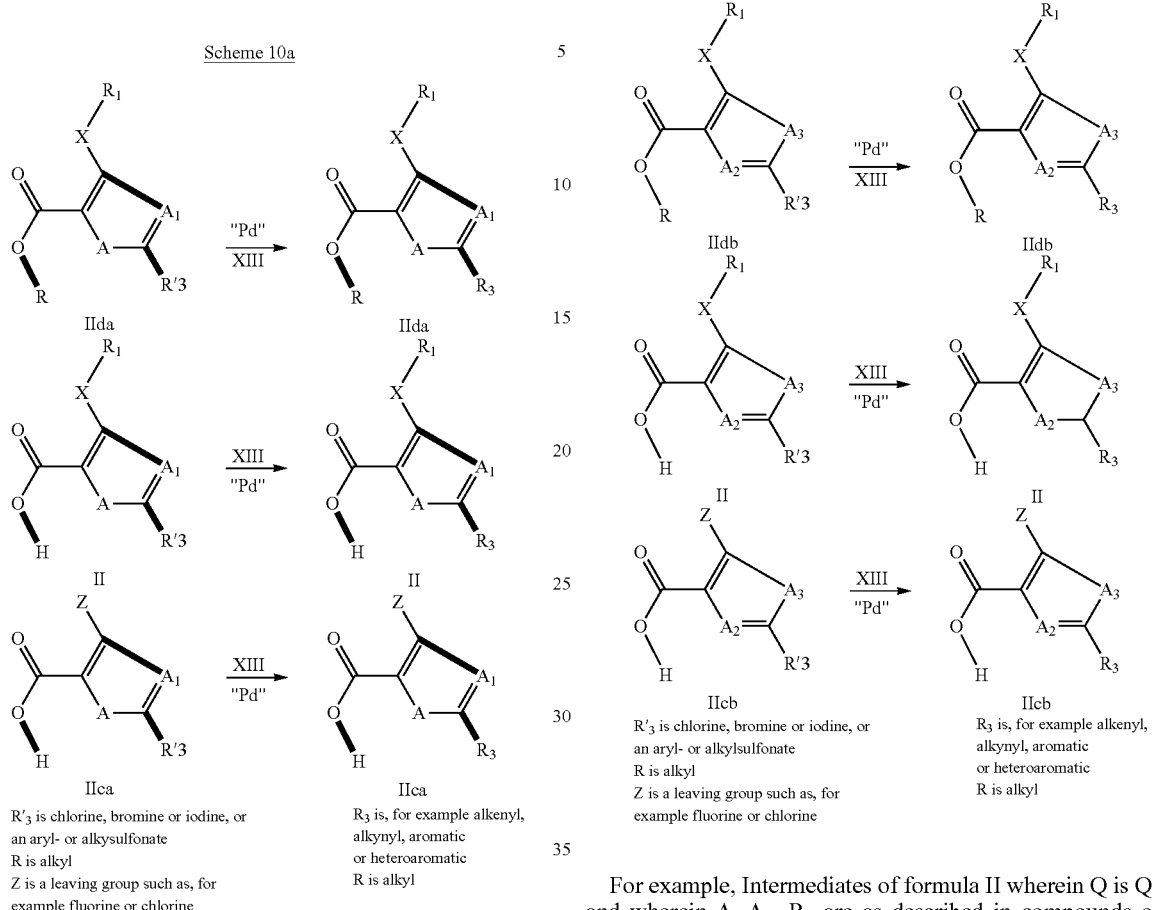
For example, Intermediates of formula II wherein Q is $Q_1$ and wherein A, $A_1$, $R_1$ are as described in compounds of formula I may be prepared as shown in scheme 11.
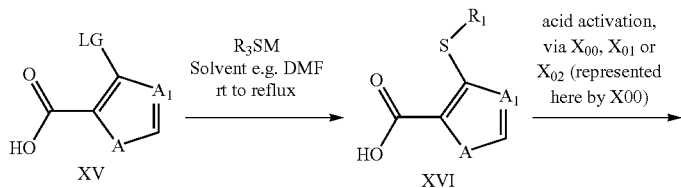
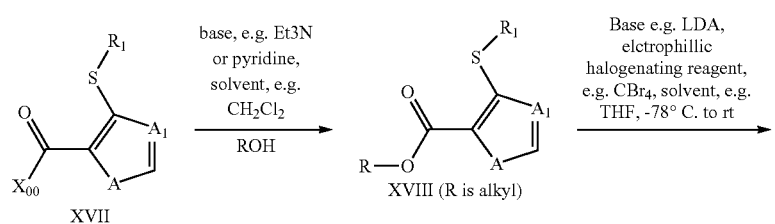

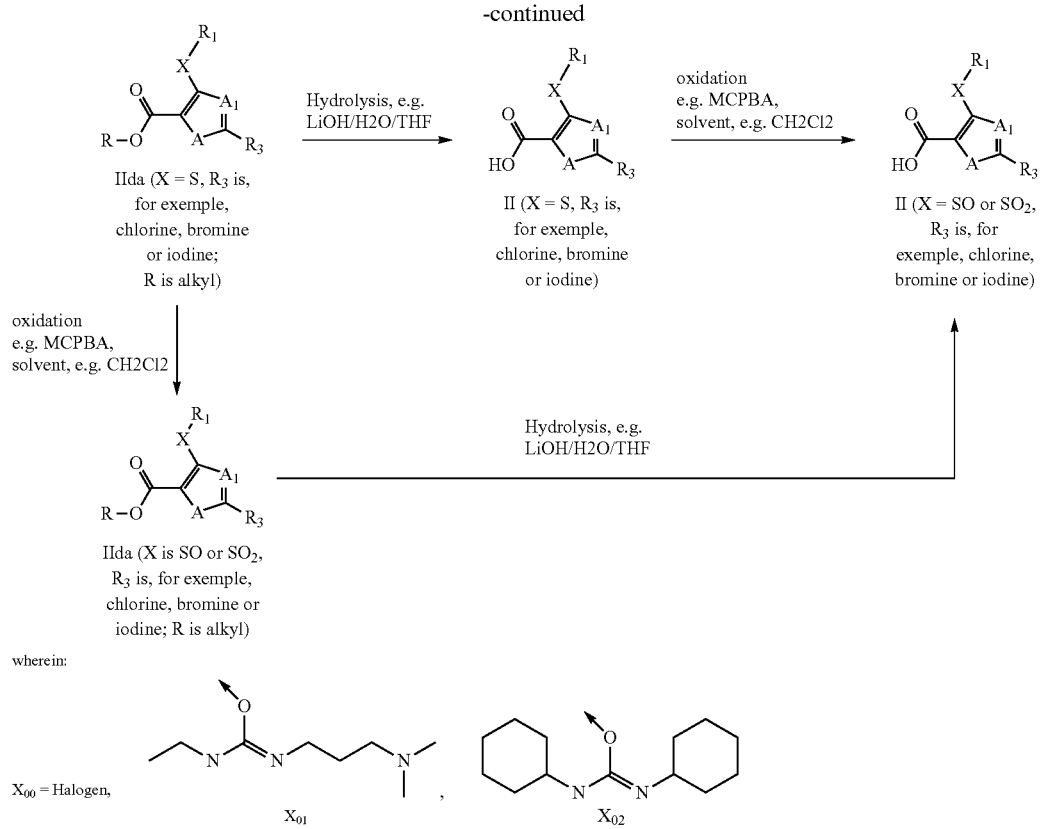

wherein:

$X_{00}$ = Halogen, $X_{01}$, $X_{02}$

As shown in scheme 11, compounds of formula XV, wherein A and $A_1$ are as described in formula I, and LG is halogen, are converted to compounds of formula XVI by treatment with compounds of the formula $MSR_1$, wherein M, and $R_1$ are as previously described, under the conditions described in scheme 8a, to give compounds of formula XVI. Compounds of formula XVI can be converted to the esters of formula XVIII, by treatment of the activated species XVII with an alcohol ROH, wherein R is $C_1$-$C_4$alkyl, in the presence of a base, for example triethylamine of pyridine, optionally in the presence of a solvent, such as methylene chloride or tetrahydrofurane. Activation of acids is known to those skilled in the art and has been previously described here for example in scheme 2. Compounds of formula XVIII can be deprotonated with a strong base, such as lithiumdi-isopropylamide, in an inert solvent such as ether or tetrahydrofurane, at temperatures between −78° C. to rt, and the anion formed quenched with an electrophilic halogen source such as bromine, carbon tetrabromide and the like, to give compounds of formula IIda, wherein X, $R_1$, A and $A_1$ are as described under formula I and $R_3$ is a leaving group such as bromide. Compounds of formula IIda can be hydrolyzed by methods known to those skilled in the art, for example with an alkaline earth metal base such as lithium hydroxide, in a mixture of water and a water miscible solvent such as THF or acetone to give compounds of formula II wherein X, $R_1$, A and $A_1$ are as described under formula I and $R_3$ is a leaving group such as bromide. Compounds of formula II can be oxidized to compounds of formula II wherein X is SO (sulfoxides), or X is $SO_2$ (sulfones) by methods known to those skilled in the art. Alternatively, compounds of formula IIda can be first oxidized to compounds of formula IIda where in X is SO (sulfoxides), or X is $SO_2$ (sulfones), and these then in turn hydrolyzed to compounds of formula II X is SO (sulfoxides), or X is $SO_2$ (sulfones).

For example, Intermediates of formula II wherein Q is $Q_2$ and wherein $A_2$, $A_3$, $R_1$ are as described in compounds of formula I may be prepared as shown in scheme 11b.

Scheme 11b:

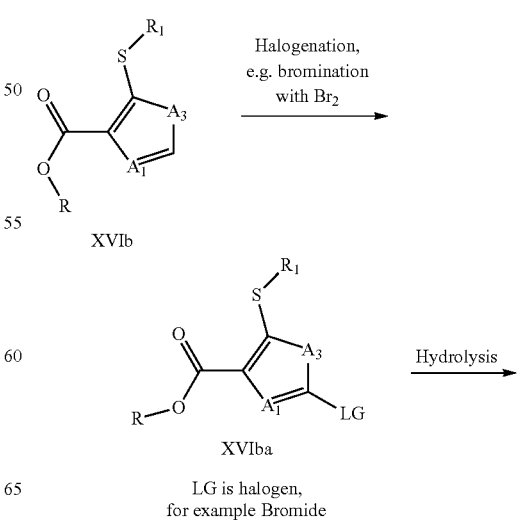

LG is halogen,
for example Bromide

-continued

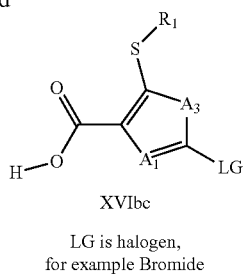

XVIbc

LG is halogen,
for example Bromide

As shown in scheme 11 b, compounds of formula XVIbc, wherein $A_1$ and $A_3$ are as described in formula I wherein R is $C_1$-$C_4$alkyl, Q is $Q_2$, and LG is halogen, can be prepared by hydrolyzing compounds of formula XVIba using the same conditions that the one described in scheme 9. Compounds of formula XVIb wherein $A_1$ and $A_3$ are as described in formula I wherein R is $C_1$-$C_4$alkyl, Q is $Q_2$, and LG is halogen, can be prepared by halogenation in a solvent such as $CCl_4$. These types of reaction are well known by the people skilled in the art and are, for example described in Bioorganic & Medicinal Chemistry Letters, 16(21), 5668-5672; 2006.

For example, Intermediates II wherein Q is $Q_1$ can be prepared as shown in scheme 12:

As shown in scheme 12, a compound of formula XXI, wherein Z and $LG_1$ are leaving group, can be reacted with a boronic acid, or boronate ester of formula XIII (Y is $B(OH)_2$ or $B(ORa)_2$ under Suzuki conditions, or with a compound of formula XIII (Y is tin derivative) under Stille conditions, as previously described in for example scheme 10a, to give compounds of formula XXII, wherein A, $A_1$ and $R_3$ are as described in formula I, and Z. is a leaving group such as fluorine, chlorine, bromine or iodine. Compounds of formula XXII can be deprotonated with a strong base, such as lithiumdiisopropylamide, in an inert solvent such as ether or tetrahydrofurane, at temperatures between −78° C. to rt, and the anion formed quenched with carbon dioxide to give carboxylic acids of formula IIcb, wherein A, $A_1$ and $R_3$ are as described under formula I and Z is a leaving group. Alternatively, the anion can be quenched with an electrophile of formula XIX, wherein $LG_2$ is a leaving group, such as halogen or methoxy, R is $C_1$-$C_4$alkyl in an inert solvent such as ether or tetrahydrofurane, at temperatures between −78° C.—ambient temperature, to give compounds of formula IIca, where the substituents are as previously described. Compounds of formula IIca can be used directly as intermediates in the synthesis of compounds of formula I, or converted to compounds of formula II (X is S) by treatment with $MSR_1$ and subsequent oxidation as previ- Scheme 12:

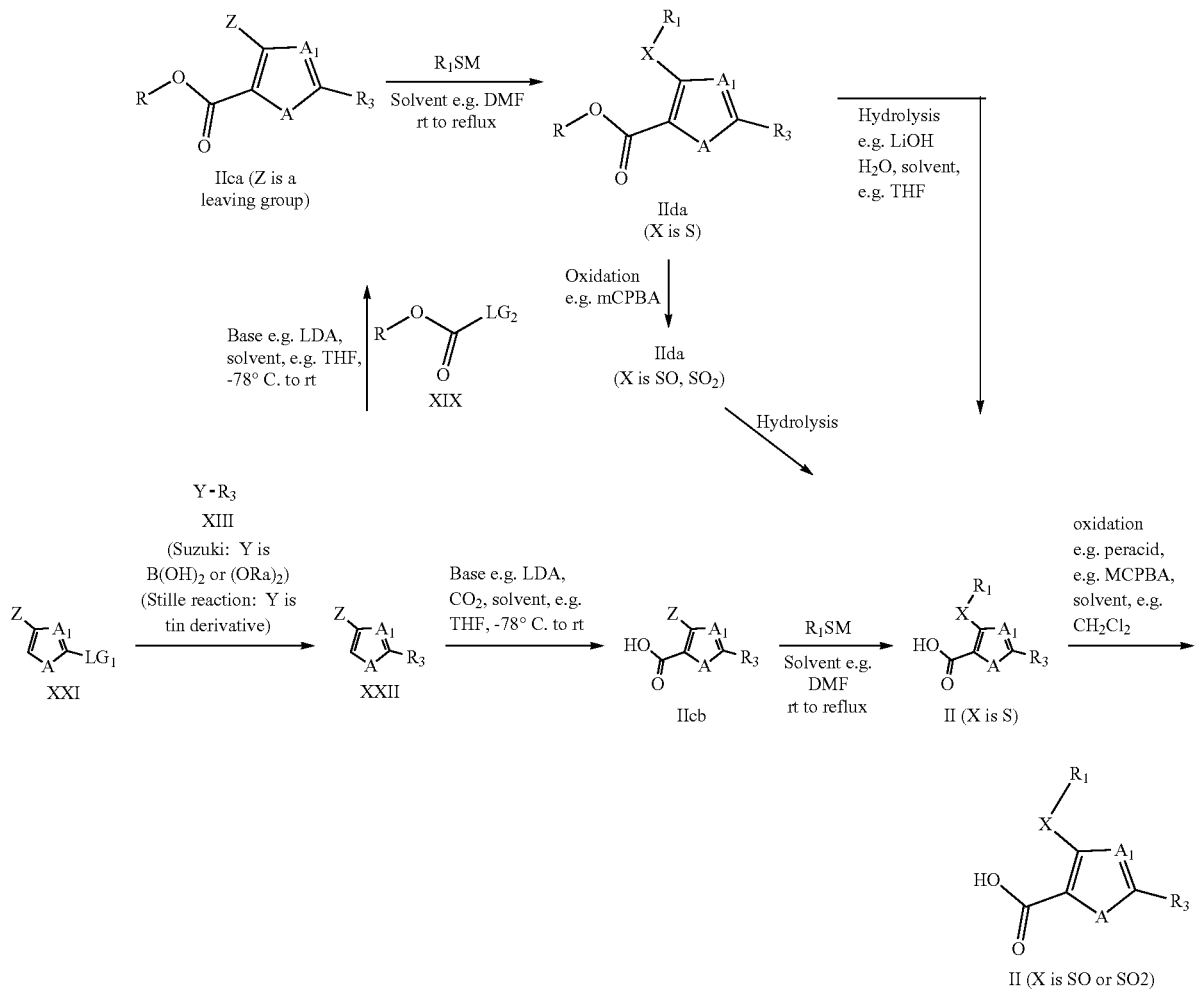

ously described to give compounds of formula II. Compounds of formula IIcb could by treatment with $MSR_1$ and subsequent oxidation as previously described to give compounds of formula II.

Compounds of formula XXIV, wherein A, $A_1$, X, $G_1$, $G_2$, $R_1$, and $R_2$ are as described in formula I, can be prepared from compounds of formula Ib (scheme 13), wherein A, $A_1$, X, $G_1$, $G_2$, $R_1$, and $R_2$ are as described in formula I. Thus, compounds of formula Id, wherein LG is chlorine, bromine or iodine, can be treated with an organometallic species like, for example, butyl lithium or an organomagnesium compound, to generate an intermediate compound of the formula XXIII, wherein M is as defined in the scheme, via metal-halogen exchange. This reaction is preferentially performed in an anhydrous aprotic solvent, such as THF, at low temperature (between −120° C. and 0° C.), preferentially between −110° C. and −60° C.). The intermediate organo-metal compound of formula XXIII is preferably directly converted into compound of formula XXIV by reaction with a boronate compound $B(OR_{b2})_3$, wherein $R_{b2}$ is a $C_1$-$C_4$alkyl group. Depending on nature of the boronate, the reaction treatment conditions and the workup conditions, the boronic acid XXIV, wherein Y is —$B(OH)_2$, or a dialkyl-boronate Y is —$B(OR_{b2})_2$, can be formed. Introduction of a pinacolborate functional group via a palladium catalyzed reaction with bispinacol diborane on compound of the formula Id, wherein LG is chlorine, bromine, iodine or triflate, is another common strategy (scheme 13). In the compounds of formula Id within scheme 13, A, $A_1$, X, $G_1$, $G_2$, $R_1$, and $R_2$ are as defined for the formula I. Those skilled in the art will appreciate that compounds of formula XXIVb or XXVb can be prepared from compounds of formula Ie in similar manner.

Scheme 13:

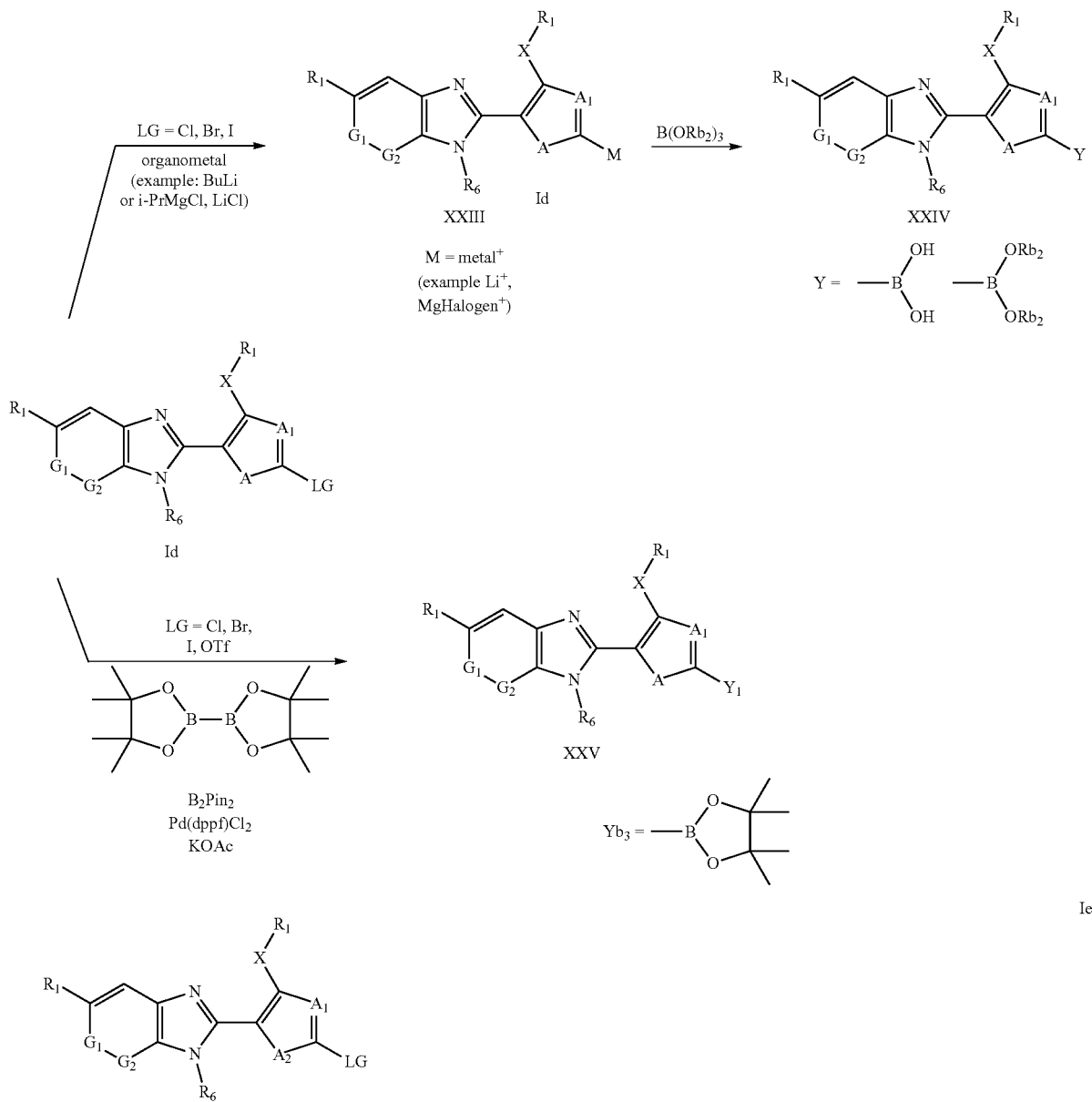

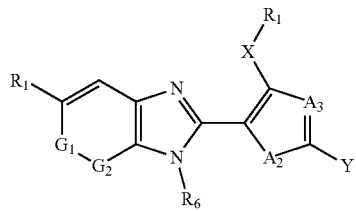

XXIVb

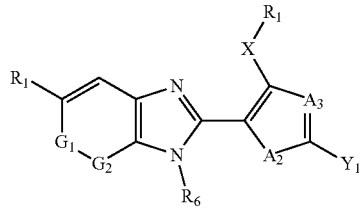

XXVb

The very similar preparation methods described in schemes 13 may be applied for the synthesis of intermediates of the formula XXIII, but in this case instead of using boronic compounds e.g. of formula B(OR$_{b2}$)$_3$, those skilled in the art would know to use a tin compound of formula (n-butyl)$_3$SnCl (as described as for example in *Eu. J. Chem.*, 4098-4104, 20, 2014) or instead of bispinacol diborane, hexabutylditin (as described in for example Eur. Pat. Appl., 2749561, 2014). This is illustrated for compound VIa in scheme 14.

Those skilled in the art will appreciate that compounds of formula XXVIb can be prepared from compounds of formula Ie in exactly the same manner.

Scheme 14.

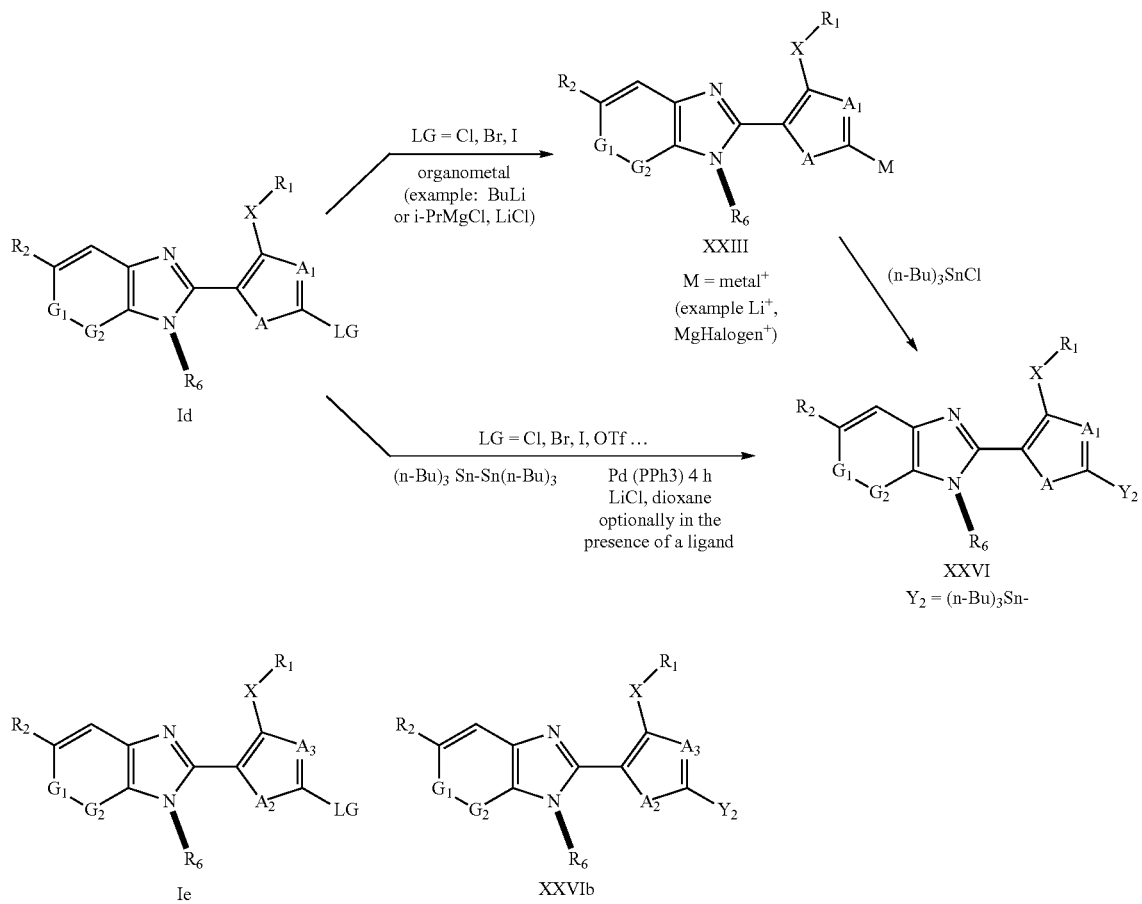

Compounds of formula I, wherein $R_3$ is, for example, alkenyl, alkynyl, aromatic or heteroaromatic, can be prepared (scheme 15a and scheme 15b) by reacting compounds of formula Iba or Ibb, wherein $R'_3$ is a leaving group like, for example, chlorine, bromine or iodine, or an aryl- or alkylsulfonate such as trifluoromethanesulfonate, or any other similar leaving group with compounds of formula XIII, wherein Y is defined as described in scheme 10a or 10b and in similar conditions as described in scheme 10a or 10b via a Suzuki or Stille cross-coupling.

Scheme 15a

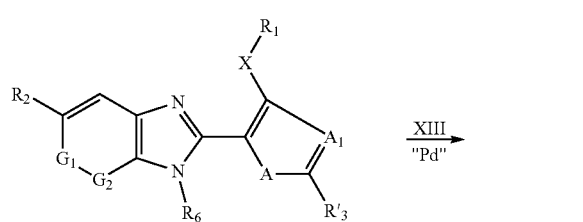

Iba, that is a compound of formula I
wherein X is S, S(O) or $SO_2$ $R'_3$ is chlorine, bromine or
iodine, or an aryl- or
alkylsulfonate

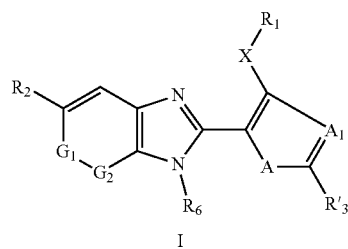

$R_3$ is for example alkenyl,
alkynl, aromatic or
heteroaromatic

Scheme 15b

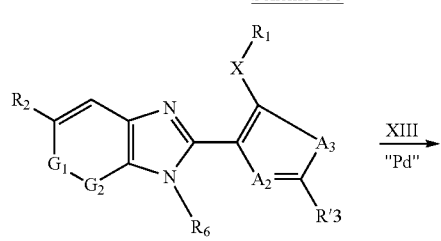

Ibb, that is a compound of formula I
wherein X is S, S(O) or $SO_2$ $R'3$ is chlorine, bromine or
iodine, or an aryl- or alkylsulfonate

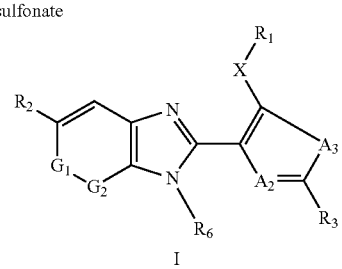

$R_3$ is for example alkenyl,
alkynyl, aromatic or
heteroaromatic

Alternatively, Compounds of formula I, wherein $R_3$ is, for example, alkenyl, alkynyl, aromatic or heteroaromatic, can be prepared by reacting compounds of formula XXIV, XXIVb, XXV, XXVb, XXVI or XXVIb, wherein Y and $Y_1$ are in similar conditions as described in scheme 10a or 10b via a Suzuki or Stille cross-coupling and continue the synthesis as described before.

In the particular case where compounds of formula I have the group T attached through a nitrogen atom (i.e. those situations where $R_3$ is a nitrogen containing heteroaromatic system), these compounds can be advantageously accessed by reacting a compound of the formula I, wherein $R'_3$ is a leaving group like, for example, chlorine, bromine or iodine with a compound of the formula XIV (H-T), wherein T is $R_3$ as described in compounds of formula I, with the condition that the attachment point is a nitrogen atom. This reaction is well known in the literature (call Ullmann reaction or variation around this type of reaction), see for example Coord. Chem. Rev. 2004, 248, 2337-2364, Tetrahedron, 67(29), 5282-5288; 2011, Angew. Chem., Int. Ed. 2003, 42, 5400-5449; Synlett 2003, 2428-2439; (d) Manifar, T.; Ind. Eng. Chem. Res. 2005, 44, 789-798. The reaction is commonly performed with one to two equivalents of a base, like potassium phosphate, in presence of a copper catalyst, like for example copper (I) iodine and under an oxygen-containing atmosphere. The reaction can be run in an inert solvent, like dioxane or toluene, usually at temperature between 50 to 150° C. and in presence or not of a additional ligand such as for example diamine ligands (e.g. trans-cyclohexyldiamine) or, for example, dibenzylideneacetone (dba) and 1,10-phenanthroline. Alternatively compounds of formula I can be prepared from compounds of formula Iba or Ibb, wherein A, $A_1$, $A_2$, $A_3$, X, $R_1$, $R_2$, $R_6$ are as previously defined and wherein $R'_3$ is a leaving group like, for example, fluorine or chlorine, by reaction of the heterocycle H-T (which contains a an appropriate NH functionality), in the presence of a base, for example an alkaline metal hydride such as sodium hydride, or an alkali metal carbonate, for example cesium or potassium carbonate, in an appropriate solvent such as N-methyl pyrollidione or DMF at temperatures between 30-150° C. See Scheme 16a and 16b.

Scheme 16a

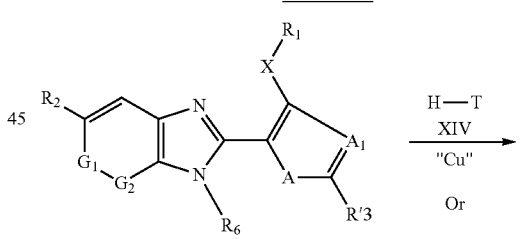

Iba, that is a compound of formula I
wherein X is S, S(O) or $SO_2$ $R'3$ is chlorine,
bromine or iodine, H—T
XIV
"Cu"

Or

NaH
DMF or
NMP
30-150° C.

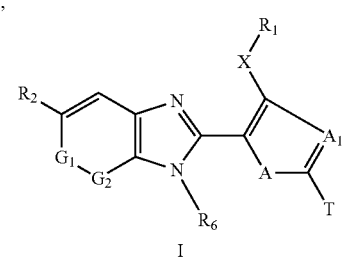

T is $R_3$ when $R_3$ is
heteroaromatic linked
by the nitrogen

Scheme 16b

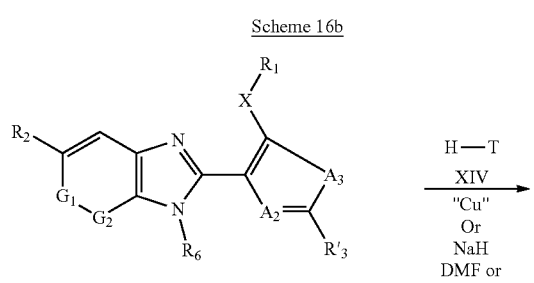

Ibb, that is a compound of formula I
wherein X is S, S(O) or SO₂

R'₃ is chlorine, bromine or iodine

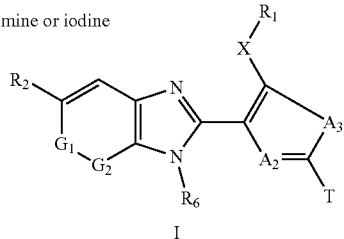
I

T is R₃ when R₃ is heteroaromatic linked by the nitrogen

Compounds of formula I, wherein Y is S, can be prepared (scheme 17) by reacting compounds of formula I-1 or I-2, wherein Y is O with a reagent that could transfer a sulphur atom such as, for example, the Lawesson's reagent in a solvent such as, for example dimethylformamide or toluene, usually at temperature between 50 to 150° C. This type of transformation is known to a person skilled in the art and are, for example, described in Tetrahedron (2007), 63(48), 11862-11877 or US20120309796.

Scheme 17

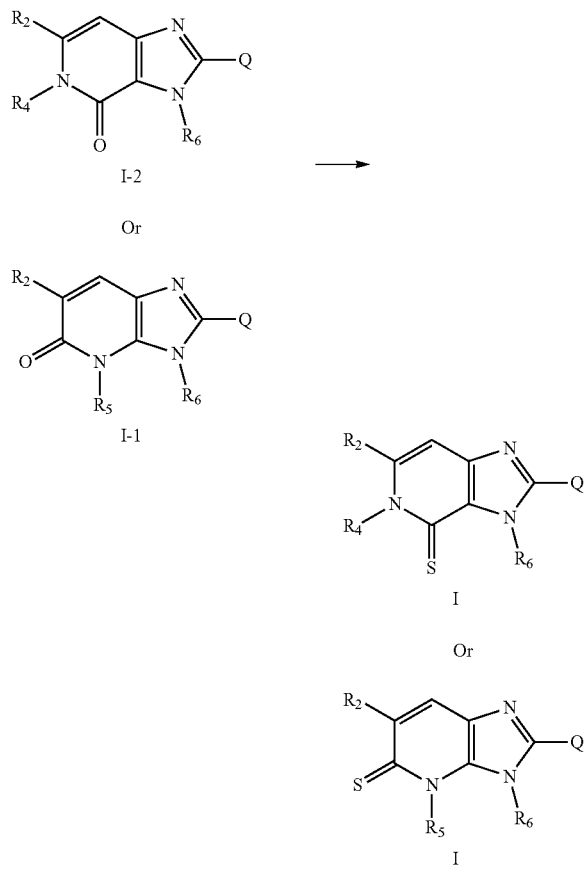

Alternatively, the O of the C(O) can be transformed on S on previews intermediate such as for example, compounds of formula XII or XI.

For preparing all other compounds of the formula (I) functionalized according to the definitions of formula III and Q, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 4 below can be prepared according to the methods described above. The examples which follow are intended to illustrate the invention and show preferred compounds of formula I. "Ph" represents the phenyl group.

Table 1: This table discloses in combination with Table 1a below 575 compounds of formula I-1a:

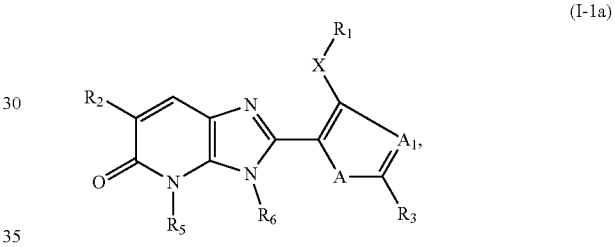

(I-1a)

wherein $R_3$ is described in Table 1a:

TABLE 1

| Comp. No. | $R_6$ | X | $R_1$ | A | $R_2$ | $R_5$ | $A_1$ |
|---|---|---|---|---|---|---|---|
| 1.001 | $CH_3$ | S | —$CH_2CH_3$ | S | $CF_3$ | $CH_3$ | CH |
| 1.002 | $CH_3$ | $SO_2$ | —$CH_2CH_3$ | S | $CF_3$ | $CH_3$ | CH |
| 1.003 | $CH_3$ | S | —$CH_2CH_3$ | S | $CF_3$ | $CH_2CH_3$ | CH |
| 1.004 | $CH_3$ | $SO_2$ | —$CH_2CH_3$ | S | $CF_3$ | $CH_2CH_3$ | CH |
| 1.005 | $CH_3$ | S | —$CH_2CH_3$ | S | $CF_3$ | $CH_3$ | N |
| 1.006 | $CH_3$ | $SO_2$ | —$CH_2CH_3$ | S | $CF_3$ | $CH_3$ | N |
| 1.007 | $CH_3$ | S | —$CH_2CH_3$ | S | $CF_3$ | $CH_2CH_3$ | N |
| 1.008 | $CH_3$ | $SO_2$ | —$CH_2CH_3$ | S | $CF_3$ | $CH_2CH_3$ | N |
| 1.009 | $CH_3$ | S | —$CH_2CH_3$ | S | $CF_2CF_3$ | $CH_3$ | CH |
| 1.010 | $CH_3$ | $SO_2$ | —$CH_2CH_3$ | S | $CF_2CF_3$ | $CH_3$ | CH |
| 1.011 | $CH_3$ | S | —$CH_2CH_3$ | S | $CF_2CF_3$ | $CH_2CH_3$ | CH |
| 1.012 | $CH_3$ | $SO_2$ | —$CH_2CH_3$ | S | $CF_2CF_3$ | $CH_2CH_3$ | CH |
| 1.013 | $CH_3$ | S | —$CH_2CH_3$ | S | $CF_2CF_3$ | $CH_3$ | N |
| 1.014 | $CH_3$ | $SO_2$ | —$CH_2CH_3$ | S | $CF_2CF_3$ | $CH_3$ | N |
| 1.015 | $CH_3$ | S | —$CH_2CH_3$ | S | $CF_2CF_3$ | $CH_2CH_3$ | N |
| 1.016 | $CH_3$ | $SO_2$ | —$CH_2CH_3$ | S | $CF_2CF_3$ | $CH_2CH_3$ | N |
| 1.017 | $CH_3$ | S | —$CH_2CH_3$ | S | $CF_2CF_3$ | $CH_3$ | CH |
| 1.018 | $CH_3$ | S | —$CH_2CH_3$ | S | $SCF_3$ | $CH_3$ | CH |
| 1.019 | $CH_3$ | $SO_2$ | —$CH_2CH_3$ | S | $SCF_3$ | $CH_3$ | CH |
| 1.020 | $CH_3$ | S | —$CH_2CH_3$ | S | $SCF_3$ | $CH_2CH_3$ | CH |
| 1.021 | $CH_3$ | $SO_2$ | —$CH_2CH_3$ | S | $SCF_3$ | $CH_2CH_3$ | CH |
| 1.022 | $CH_3$ | S | —$CH_2CH_3$ | S | $SCF_3$ | $CH_3$ | N |
| 1.023 | $CH_3$ | $SO_2$ | —$CH_2CH_3$ | S | $SCF_3$ | $CH_3$ | N |
| 1.024 | $CH_3$ | S | —$CH_2CH_3$ | S | $SCF_3$ | $CH_2CH_3$ | N |
| 1.025 | $CH_3$ | $SO_2$ | —$CH_2CH_3$ | S | $SCF_3$ | $CH_2CH_3$ | N |

TABLE 1a

| Comp. No | R₃ |
|---|---|
| Y1 | phenyl |
| Y2 | 2-chlorophenyl |
| Y3 | 3-chlorophenyl |
| Y4 | 4-chlorophenyl |
| Y5 | 2-(trifluoromethyl)phenyl |
| Y6 | 3-(trifluoromethyl)phenyl |
| Y7 | 4-(trifluoromethyl)phenyl |
| Y8 | 5-chloropyridin-2-yl |
| Y9 | 3-chloropyridin-2-yl |
| Y10 | 4-(trifluoromethyl)pyridin-2-yl |
| Y11 | 4-cyanophenyl |

TABLE 1a-continued

| Comp. No | R₃ |
|---|---|
| Y12 | 3,5-dichloropyridin-2-yl |
| Y13 | 5-fluoropyridin-2-yl |
| Y14 | 3-fluoropyridazin-6-yl |
| Y15 | 3,5-difluoropyridin-2-yl |
| Y16 | 3-fluoro-5-(trifluoromethyl)pyridin-2-yl |
| Y17 | 5-chloropyrimidin-2-yl |
| Y18 | pyrimidin-2-yl |
| Y11 | 3-(trifluoromethyl)-1H-pyrazol-1-yl |
| Y12 | 3-chloro-1H-pyrazol-1-yl |
| Y13 | 5-cyanopyrimidin-2-yl |
| Y14 | 4-(trifluoromethyl)-1H-pyrazol-1-yl |
| Y15 | 4-chloro-1H-pyrazol-1-yl |

TABLE 1a-continued

| Comp. No | R₃ |
|---|---|
| Y16 | cyclopropyl |
| Y17 | 1-cyanocyclopropyl |
| Y18 | 1-methylcyclopropyl |
| Y19 | 1-(trifluoromethyl)cyclopropyl |
| Y20 | (E)-2-(2-(trifluoromethyl)phenyl)vinyl |
| Y21 | 2-(2-(trifluoromethyl)phenyl)ethyl |
| Y22 | 2-(2-(trifluoromethyl)phenyl)ethynyl |
| Y23 | 6-cyanopyridin-3-yl |

And the N-oxides or tautomers of the compounds of the combination of Table 1 with Table 1a.

For example: compound 1.001Y1 is a compound of the following formula

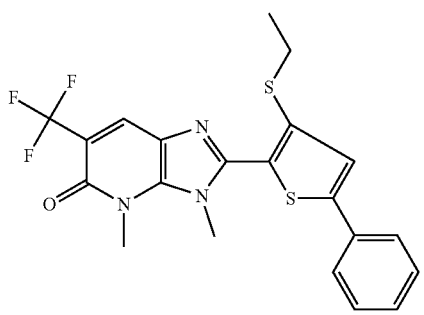 [SMILES: CCSc1cc(-c2ccccc2)sc1-c1nc2cc(C(F)(F)F)c(=O)n(C)c2n1C]

Table 2: This table discloses in combination with Table 2a below 575 compounds of formula I-1b:

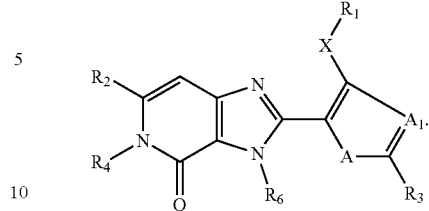

(I-1b)

wherein $R_3$ is described in Table 2a:

TABLE 2

| Comp. No. | $R_6$ | X | $R_1$ | A | $R_2$ | $R_4$ | $A_1$ |
|---|---|---|---|---|---|---|---|
| 2.001 | $CH_3$ | S | —$CH_2CH_3$ | S | $CF_3$ | $CH_3$ | CH |
| 2.002 | $CH_3$ | $SO_2$ | —$CH_2CH_3$ | S | $CF_3$ | $CH_3$ | CH |
| 2.003 | $CH_3$ | S | —$CH_2CH_3$ | S | $CF_3$ | $CH_2CH_3$ | CH |
| 2.004 | $CH_3$ | $SO_2$ | —$CH_2CH_3$ | S | $CF_3$ | $CH_2CH_3$ | CH |
| 2.005 | $CH_3$ | S | —$CH_2CH_3$ | S | $CF_3$ | $CH_3$ | N |
| 2.006 | $CH_3$ | $SO_2$ | —$CH_2CH_3$ | S | $CF_3$ | $CH_3$ | N |
| 2.007 | $CH_3$ | S | —$CH_2CH_3$ | S | $CF_3$ | $CH_2CH_3$ | N |
| 2.008 | $CH_3$ | $SO_2$ | —$CH_2CH_3$ | S | $CF_3$ | $CH_2CH_3$ | N |
| 2.009 | $CH_3$ | S | —$CH_2CH_3$ | S | $CF_2CF_3$ | $CH_3$ | CH |
| 2.010 | $CH_3$ | $SO_2$ | —$CH_2CH_3$ | S | $CF_2CF_3$ | $CH_3$ | CH |
| 2.011 | $CH_3$ | S | —$CH_2CH_3$ | S | $CF_2CF_3$ | $CH_2CH_3$ | CH |
| 2.012 | $CH_3$ | $SO_2$ | —$CH_2CH_3$ | S | $CF_2CF_3$ | $CH_2CH_3$ | CH |
| 2.013 | $CH_3$ | S | —$CH_2CH_3$ | S | $CF_2CF_3$ | $CH_3$ | N |
| 2.014 | $CH_3$ | $SO_2$ | —$CH_2CH_3$ | S | $CF_2CF_3$ | $CH_3$ | N |
| 2.015 | $CH_3$ | S | —$CH_2CH_3$ | S | $CF_2CF_3$ | $CH_2CH_3$ | N |
| 2.016 | $CH_3$ | $SO_2$ | —$CH_2CH_3$ | S | $CF_2CF_3$ | $CH_2CH_3$ | N |
| 2.017 | $CH_3$ | S | —$CH_2CH_3$ | S | $CF_2CF_3$ | $CH_3$ | CH |
| 2.018 | $CH_3$ | S | —$CH_2CH_3$ | S | $SCF_3$ | $CH_3$ | CH |
| 2.019 | $CH_3$ | $SO_2$ | —$CH_2CH_3$ | S | $SCF_3$ | $CH_3$ | CH |
| 2.020 | $CH_3$ | S | —$CH_2CH_3$ | S | $SCF_3$ | $CH_2CH_3$ | CH |
| 2.021 | $CH_3$ | $SO_2$ | —$CH_2CH_3$ | S | $SCF_3$ | $CH_2CH_3$ | CH |
| 2.022 | $CH_3$ | S | —$CH_2CH_3$ | S | $SCF_3$ | $CH_3$ | N |
| 2.023 | $CH_3$ | $SO_2$ | —$CH_2CH_3$ | S | $SCF_3$ | $CH_3$ | N |
| 2.024 | $CH_3$ | S | —$CH_2CH_3$ | S | $SCF_3$ | $CH_2CH_3$ | N |
| 2.025 | $CH_3$ | $SO_2$ | —$CH_2CH_3$ | S | $SCF_3$ | $CH_2CH_3$ | N |

TABLE 2a

| Comp. No | R₃ |
|---|---|
| Y1 | phenyl |
| Y2 | 2-chlorophenyl |
| Y3 | 3-chlorophenyl |
| Y4 | 4-chlorophenyl |

TABLE 2a-continued
| Comp. No | R₃ |
|---|---|
| Y5 | 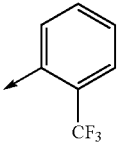 |
| Y6 | 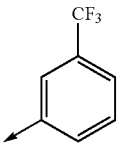 |
| Y7 | 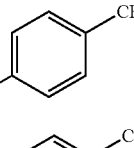 |
| Y8 | 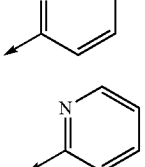 |
| Y9 | 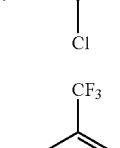 |
| Y10 | 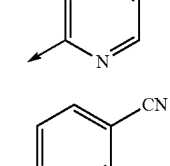 |
| Y11 |  |
| Y12 | 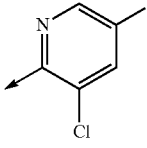 |
| Y13 | 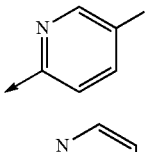 |
| Y14 | 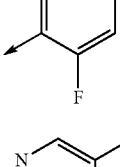 |
| Y15 | 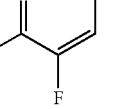 |
| Y16 | 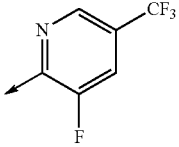 |
| Y17 | 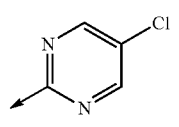 |
| Y18 | 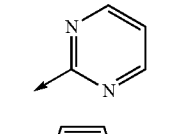 |
| Y11 | 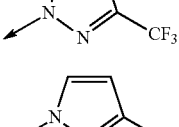 |
| Y12 | 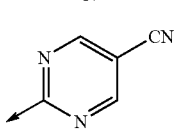 |
| Y13 | 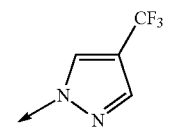 |
| Y14 | 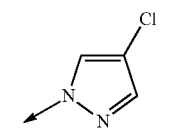 |
| Y15 | 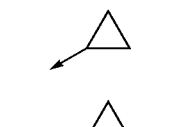 |
| Y16 | 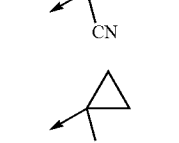 |
| Y17 | 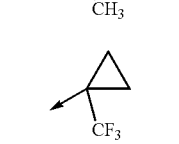 |
| Y18 | 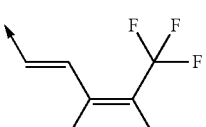 |
| Y19 |  |
| Y20 |  |

TABLE 2a-continued

| Comp. No | R₃ |
|---|---|
| Y21 | 2-(trifluoromethyl)phenethyl |
| Y22 | 2-(trifluoromethyl)phenylethynyl |
| Y23 | 6-cyanopyridin-3-yl (attached via 2-position) | and the N-oxides and tautomers of the compounds of Table 2 in combination with Table 2a.

For example: compound 2.001Y1 is a compound of the following formula

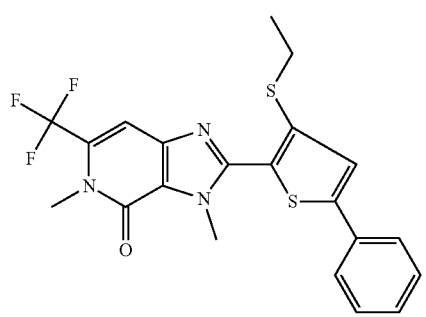

Table 3: This table discloses in combination with Table 3a below 575 compounds of formula I-1a:

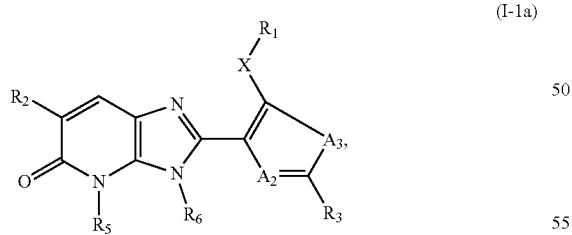

(I-1a)

wherein $R_3$ is described in Table 3a:

TABLE 3

| Comp. No. | $R_6$ | X | $R_1$ | $A_3$ | $R_2$ | $R_5$ | $A_2$ |
|---|---|---|---|---|---|---|---|
| 3.001 | $CH_3$ | S | —$CH_2CH_3$ | S | $CF_3$ | $CH_3$ | CH |
| 3.002 | $CH_3$ | $SO_2$ | —$CH_2CH_3$ | S | $CF_3$ | $CH_3$ | CH |
| 3.003 | $CH_3$ | S | —$CH_2CH_3$ | S | $CF_3$ | $CH_2CH_3$ | CH |
| 3.004 | $CH_3$ | $SO_2$ | —$CH_2CH_3$ | S | $CF_3$ | $CH_2CH_3$ | CH |

TABLE 3-continued

| Comp. No. | $R_6$ | X | $R_1$ | $A_3$ | $R_2$ | $R_5$ | $A_2$ |
|---|---|---|---|---|---|---|---|
| 3.005 | $CH_3$ | S | —$CH_2CH_3$ | S | $CF_3$ | $CH_3$ | N |
| 3.006 | $CH_3$ | $SO_2$ | —$CH_2CH_3$ | S | $CF_3$ | $CH_3$ | N |
| 3.007 | $CH_3$ | S | —$CH_2CH_3$ | S | $CF_3$ | $CH_2CH_3$ | N |
| 3.008 | $CH_3$ | $SO_2$ | —$CH_2CH_3$ | S | $CF_3$ | $CH_2CH_3$ | N |
| 3.009 | $CH_3$ | S | —$CH_2CH_3$ | S | $CF_2CF_3$ | $CH_3$ | CH |
| 3.010 | $CH_3$ | $SO_2$ | —$CH_2CH_3$ | S | $CF_2CF_3$ | $CH_3$ | CH |
| 3.011 | $CH_3$ | S | —$CH_2CH_3$ | S | $CF_2CF_3$ | $CH_2CH_3$ | CH |
| 3.012 | $CH_3$ | $SO_2$ | —$CH_2CH_3$ | S | $CF_2CF_3$ | $CH_2CH_3$ | CH |
| 3.013 | $CH_3$ | S | —$CH_2CH_3$ | S | $CF_2CF_3$ | $CH_3$ | N |
| 3.014 | $CH_3$ | $SO_2$ | —$CH_2CH_3$ | S | $CF_2CF_3$ | $CH_3$ | N |
| 3.015 | $CH_3$ | S | —$CH_2CH_3$ | S | $CF_2CF_3$ | $CH_2CH_3$ | N |
| 3.016 | $CH_3$ | $SO_2$ | —$CH_2CH_3$ | S | $CF_2CF_3$ | $CH_2CH_3$ | N |
| 3.017 | $CH_3$ | S | —$CH_2CH_3$ | S | $CF_2CF_3$ | $CH_3$ | CH |
| 3.018 | $CH_3$ | S | —$CH_2CH_3$ | S | $SCF_3$ | $CH_3$ | CH |
| 3.019 | $CH_3$ | $SO_2$ | —$CH_2CH_3$ | S | $SCF_3$ | $CH_3$ | CH |
| 3.020 | $CH_3$ | S | —$CH_2CH_3$ | S | $SCF_3$ | $CH_2CH_3$ | CH |
| 3.021 | $CH_3$ | $SO_2$ | —$CH_2CH_3$ | S | $SCF_3$ | $CH_2CH_3$ | CH |
| 3.022 | $CH_3$ | S | —$CH_2CH_3$ | S | $SCF_3$ | $CH_3$ | N |
| 3.023 | $CH_3$ | $SO_2$ | —$CH_2CH_3$ | S | $SCF_3$ | $CH_3$ | N |
| 3.024 | $CH_3$ | S | —$CH_2CH_3$ | S | $SCF_3$ | $CH_2CH_3$ | N |
| 3.025 | $CH_3$ | $SO_2$ | —$CH_2CH_3$ | S | $SCF_3$ | $CH_2CH_3$ | N |

TABLE 3a

| Comp. No | R₃ |
|---|---|
| Y1 | phenyl |
| Y2 | 2-chlorophenyl |
| Y3 | 3-chlorophenyl |
| Y4 | 4-chlorophenyl |
| Y5 | 2-(trifluoromethyl)phenyl |
| Y6 | 3-(trifluoromethyl)phenyl |
| Y7 | 4-(trifluoromethyl)phenyl |

TABLE 3a-continued
| Comp. No | R₃ |
|---|---|
| Y8 | 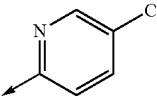 5-chloropyridin-2-yl |
| Y9 | 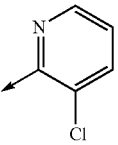 3-chloropyridin-2-yl |
| Y10 | 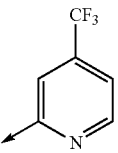 4-(trifluoromethyl)pyridin-2-yl |
| Y11 | 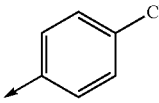 4-cyanophenyl |
| Y12 | 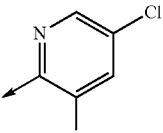 3,5-dichloropyridin-2-yl |
| Y13 | 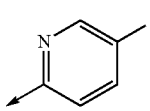 5-fluoropyridin-2-yl |
| Y14 | 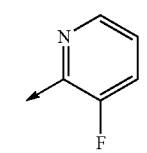 3-fluoropyridin-2-yl |
| Y15 |  3,5-difluoropyridin-2-yl |
| Y16 | 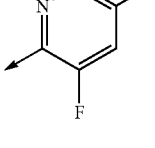 3-fluoro-5-(trifluoromethyl)pyridin-2-yl |
| Y17 | 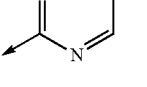 5-chloropyrimidin-2-yl |
| Y18 | 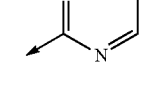 pyrimidin-2-yl |
TABLE 3a-continued
| Comp. No | R₃ |
|---|---|
| Y11 | 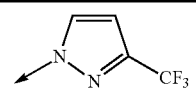 |
| Y12 | 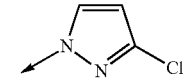 |
| Y13 | 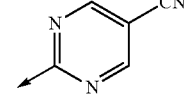 |
| Y14 | 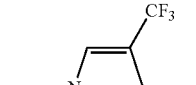 |
| Y15 | 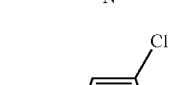 |
| Y16 |  |
| Y17 |  |
| Y18 |  |
| Y19 |  |
| Y20 | 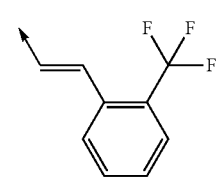 |
| Y21 | 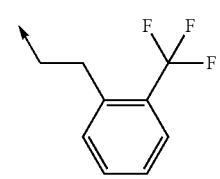 |
| Y22 | 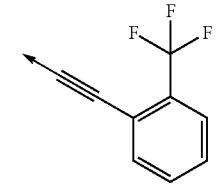 |

TABLE 3a-continued

| Comp. No | R₃ |
|---|---|
| Y23 | 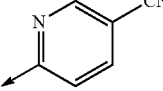 | and the N-oxides or tautomers of the compounds of Table 3 in combination with Table 3a.

For example: compound 1.001Y1 is a compound of the following formula

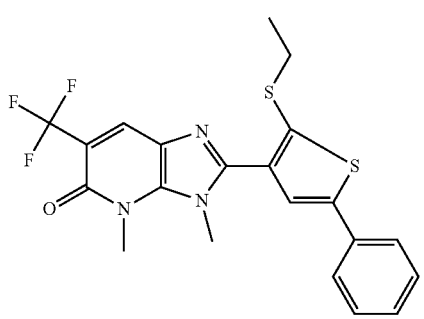 [SMILES: CCSc1sc(-c2ccccc2)cc1-c1nc2cc(C(F)(F)F)c(=O)n(C)c2n1C]

Table 4: This table discloses in combination with Table 4a below the 575 compounds of formula I-1b:

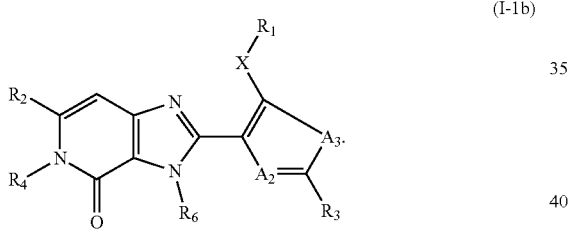

(I-1b)

Wherein R₃ is described in Table 4a:

TABLE 4

| Comp. No. | R₆ | X | R₁ | A₃ | R₂ | R₄ | A₂ |
|---|---|---|---|---|---|---|---|
| 4.001 | $CH_3$ | S | $-CH_2CH_3$ | S | $CF_3$ | $CH_3$ | CH |
| 4.002 | $CH_3$ | $SO_2$ | $-CH_2CH_3$ | S | $CF_3$ | $CH_3$ | CH |
| 4.003 | $CH_3$ | S | $-CH_2CH_3$ | S | $CF_3$ | $CH_2CH_3$ | CH |
| 4.004 | $CH_3$ | $SO_2$ | $-CH_2CH_3$ | S | $CF_3$ | $CH_2CH_3$ | CH |
| 4.005 | $CH_3$ | S | $-CH_2CH_3$ | S | $CF_3$ | $CH_3$ | N |
| 4.006 | $CH_3$ | $SO_2$ | $-CH_2CH_3$ | S | $CF_3$ | $CH_3$ | N |
| 4.007 | $CH_3$ | S | $-CH_2CH_3$ | S | $CF_3$ | $CH_2CH_3$ | N |
| 4.008 | $CH_3$ | $SO_2$ | $-CH_2CH_3$ | S | $CF_3$ | $CH_2CH_3$ | N |
| 4.009 | $CH_3$ | S | $-CH_2CH_3$ | S | $CF_2CF_3$ | $CH_3$ | CH |
| 4.010 | $CH_3$ | $SO_2$ | $-CH_2CH_3$ | S | $CF_2CF_3$ | $CH_3$ | CH |
| 4.011 | $CH_3$ | S | $-CH_2CH_3$ | S | $CF_2CF_3$ | $CH_2CH_3$ | CH |
| 4.012 | $CH_3$ | $SO_2$ | $-CH_2CH_3$ | S | $CF_2CF_3$ | $CH_2CH_3$ | CH |
| 4.013 | $CH_3$ | S | $-CH_2CH_3$ | S | $CF_2CF_3$ | $CH_3$ | N |
| 4.014 | $CH_3$ | $SO_2$ | $-CH_2CH_3$ | S | $CF_2CF_3$ | $CH_3$ | N |
| 4.015 | $CH_3$ | S | $-CH_2CH_3$ | S | $CF_2CF_3$ | $CH_2CH_3$ | N |
| 4.016 | $CH_3$ | $SO_2$ | $-CH_2CH_3$ | S | $CF_2CF_3$ | $CH_2CH_3$ | N |
| 4.017 | $CH_3$ | S | $-CH_2CH_3$ | S | $CF_2CF_3$ | $CH_3$ | CH |
| 4.018 | $CH_3$ | S | $-CH_2CH_3$ | S | $SCF_3$ | $CH_3$ | CH |
| 4.019 | $CH_3$ | $SO_2$ | $-CH_2CH_3$ | S | $SCF_3$ | $CH_3$ | CH |
| 4.020 | $CH_3$ | S | $-CH_2CH_3$ | S | $SCF_3$ | $CH_2CH_3$ | CH |
| 4.021 | $CH_3$ | $SO_2$ | $-CH_2CH_3$ | S | $SCF_3$ | $CH_2CH_3$ | CH |
| 4.022 | $CH_3$ | S | $-CH_2CH_3$ | S | $SCF_3$ | $CH_3$ | N |
| 4.023 | $CH_3$ | $SO_2$ | $-CH_2CH_3$ | S | $SCF_3$ | $CH_3$ | N |
| 4.024 | $CH_3$ | S | $-CH_2CH_3$ | S | $SCF_3$ | $CH_2CH_3$ | N |
| 4.025 | $CH_3$ | $SO_2$ | $-CH_2CH_3$ | S | $SCF_3$ | $CH_2CH_3$ | N |

TABLE 4a

| Comp. No | R₃ |
|---|---|
| Y1 | 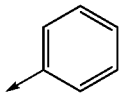 |
| Y2 | 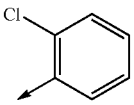 |
| Y3 | 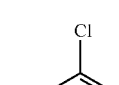 |
| Y4 | 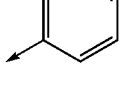 |
| Y5 | 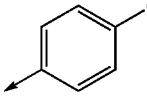 |
| Y6 | 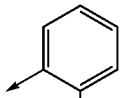 |
| Y7 | 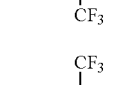 |
| Y8 | 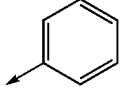 |
| Y9 | 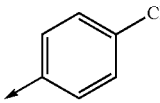 |
| Y10 | 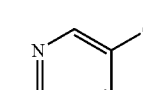 |

TABLE 4a-continued
| Comp. No | R₃ |
|---|---|
| Y11 | 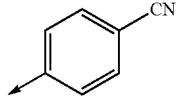 |
| Y12 | 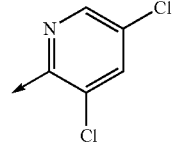 |
| Y13 | 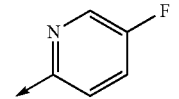 |
| Y14 |  |
| Y15 |  |
| Y16 | 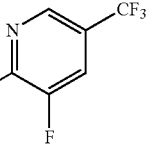 |
| Y17 | 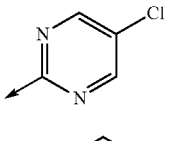 |
| Y18 | 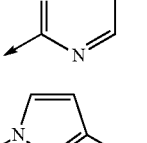 |
| Y11 | 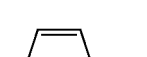 |
| Y12 | 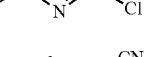 |
| Y13 | 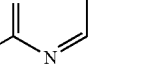 |
| Y14 | 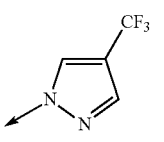 |
| Y15 | 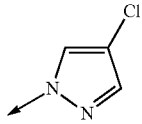 |
| Y16 |  |
| Y17 |  |
| Y18 | 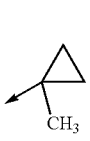 |
| Y19 | 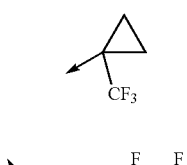 |
| Y20 | 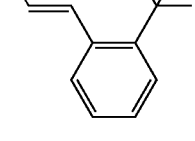 |
| Y21 | 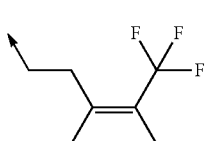 |
| Y22 | 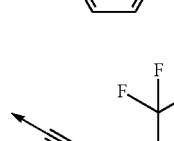 |
| Y23 | 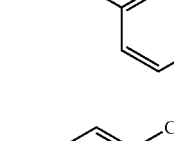 |
and the N-oxides and tautomers of the compounds of Table 4 in combination with Table 4a.
For example: compound 4.001Y1 is a compound of the following formula

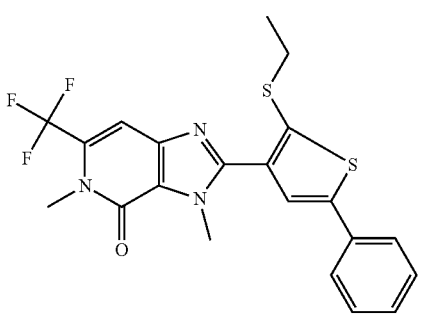 [SMILES: CCSc1sc(-c2ccccc2)cc1-c1nc2cc(C(F)(F)F)n(C)c(=O)c2n1C]

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp *Acaricalus* spp, *Aceria* spp, *Acarus siro*, *Amblyomma* spp., *Argas* spp., *Boophi-lus* spp., *Brevipalpus* spp., *Bryobia* spp, *Calipitrimerus* spp., *Chorioptes* spp., *Dermanyssus gallinae*, *Dermatophagoides* spp., *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotino-phara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera sp*, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp., *Trialeurodes* spp., *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order lsoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*,

*Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocolletis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absolute*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharine.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., *and Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; Deroceras (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae *Helicigona arbustorum*); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose,* or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |

TABLE B-continued

Examples of native woodborers of economic importance.

| Family | Species | Host or Crop Infested |
|---|---|---|
| Cerambycidae | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as Cyclocephala spp. (e.g. masked chafer, C. lurida), Rhizotrogus spp. (e.g. European chafer, R. majalis), Cotinus spp. (e.g. Green June beetle, C. nitida), Popillia spp. (e.g. Japanese beetle, P. japonica), Phyllophaga spp. (e.g. May/June beetle), Ataenius spp. (e.g. Black turfgrass ataenius, A. spretulus), Maladera spp. (e.g. Asiatic garden beetle, M. castanea) and Tomarus spp.), ground pearls (Margarodes spp.), mole crickets (tawny, southern, and short-winged; Scapteriscus spp., Gryllotalpa africana) and leatherjackets (European crane fly, Tipula spp.).

The present invention may also be used to control insect pests of turfgrass that are thatch dwelling, including armyworms (such as fall armyworm Spodoptera frugiperda, and common armyworm Pseudaletia unipuncta), cutworms, billbugs (Sphenophorus spp., such as S. venatus verstitus and S. parvulus), and sod webworms (such as Crambus spp. and the tropical sod webworm, Herpetogramma phaeopteralis).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and green bugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Lam inosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g. tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):

Emulsifiable concentrates:

| | |
|---|---|
| active ingredient: | 1 to 95%, preferably 5 to 20% |
| surfactant: | 1 to 30%, preferably 10 to 20% |
| solvent: | 5 to 98%, preferably 70 to 85% |

Dusts:

| | |
|---|---|
| active ingredient: | 0.1 to 10%, preferably 0.1 to 1% |
| solid carrier: | 99.9 to 90%, preferably 99.9 to 99% |

Suspension concentrates:

| | |
|---|---|
| active ingredient: | 5 to 75%, preferably 10 to 50% |
| water: | 94 to 24%, preferably 88 to 30% |
| surfactant: | 1 to 40%, preferably 2 to 30% |

Wettable powders:

| | |
|---|---|
| active ingredient: | 0.5 to 90%, preferably 1 to 80% |
| surfactant: | 0.5 to 20%, preferably 1 to 15% |
| solid carrier: | 5 to 99%, preferably 15 to 98% |

Granulates:

| | |
|---|---|
| active ingredient: | 0.5 to 30%, preferably 3 to 15% |
| solid carrier: | 99.5 to 70%, preferably 97 to 85% |

PREPARATORY EXAMPLES

"Mp" means melting point in ° C. Free radicals represent methyl groups. $^1$H and $^{19}$F NMR measurements were recorded on Brucker 400 MHz or 300 MHz spectrometers, chemical shifts are given in ppm relevant to a TMS standard. Spectra measured in deuterated solvents as indicated.

LCMS Methods:

Method A (SQD13):

Spectra were recorded on a Mass Spectrometer from Waters (SQD Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Synthesis of Intermediates:

Intermediate 1: Synthesis of 4-amino-1-methyl-3-(methylamino)-6-(trifluoromethyl)pyridin-2-one

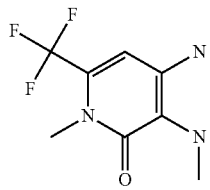

Step A: 1-methyl-3-(methylamino)-6-(trifluoromethyl)pyridin-2-one

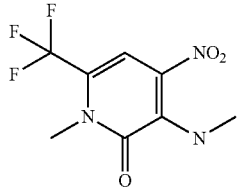 [SMILES: CNc1c([N+](=O)[O-])cc(C(F)(F)F)n(C)c1=O]

To a solution of 3-amino-1-methyl-6-(trifluoromethyl)pyridin-2-one (1.00 g, 5.20 mmol, Commercially available or synthesised as described for example in Synthesis 2005, No. 8, pp 1269-1278, Synthesis 2011, No. 7, pp 1149-1156) in 1,4-dioxane (62.5 mL, 726 mmol) and pyridine (1.49 mL, 18.2 mmol) under argon was additionned diacetoxycopper (2.39 g, 13.0 mmol). The mixture was stirred for 15 min before addition of methylboronic acid (0.803 g, 13.0 mmol). The resulting green/blue suspension was refluxed for 5 hours. After cooling, the solution was filtered through a celite pad. The dark green solution was concentrated under vacuum and was subjected to column chromatography over silica gel, eluting with ethyl acetate/cyclohexane. The selected fractions were evaporated to yield the title compound (0.71 g). $^1$H NMR (400 MHz, CDCl$_3$) δ ppm 7.27 (s, 1H); 6.72 (d, 1H); 6.04 (d, 2H), 5.46 (bs, 1H), 3.68 (s, 3H), 2.88 (d, 3H).

Step B: 1-methyl-3-(methylamino)-4-nitro-6-(trifluoromethyl)pyridin-2-one

A solution of 1-methyl-3-(methylamino)-6-(trifluoromethyl)pyridin-2-one (4.00 g, 19.4 mmol) sulfuric acid (58.2 mL) was cooled with an ice bath at 0° C. Then, ice (20.0 g) and nitric acid (1.88 g, 1.35 mL, 19.4 mmol) were added. After 15 min at 0-10° C., the brown thick solution was poured into iced water. The orange precipitate forms was filtrated off, rinsing with water and drying under vacuum to give an orange solid. The water phase was extracted 3 times with AcOEt and the orange solid, obtained before, was added to the combinated organic phase. The combinated organic phase was washed with a saturated solution of sodium hydrogenocarbonate, water and brine, dried over magnesium sulfate and concentrated under vacuum to give yield the title compound (4.0 g). The compound was used without extrapurification for the next step. LC-MS (Method A): RT 0.91, 252 (M+H$^+$), 250 (M−H$^+$).

Step C: 4-amino-1-methyl-3-(methylamino)-6-(trifluoromethyl)pyridin-2-one

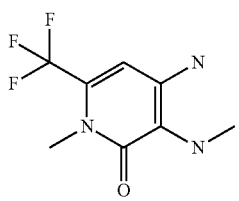

To a solution of 1-methyl-3-(methylamino)-4-nitro-6-(trifluoromethyl)pyridin-2-one (3.0 g, 11.9 mmol) in propan-2-ol (98.1 g, 125 mL, 1620 mmol) was added tin(II) chloride dihydrate (8.24 g, 43.0 mmol) followed by hydrogen chloride (10 mL, 120 mmol, 37%). The resulting solution was stirred at 70° C. for one hour, and, then allowed to cool down to ambient temperature. The reaction mixture was poured into water, and pH was adjusted to 10-12 with a concentrated solution of sodium hydroxide (30%). The aqueous phase was extracted three times with ethyl acetate, the organic phases were combined, dried over magnesium sulfate and concentrated under vacuum. subjected to column chromatography over silica gel, eluting with ethyl acetate/cyclohexane. The selected fractions were evaporated to yield the title compound (2.15 g). $^1$H NMR (400 MHz, CDCl$_3$) δ ppm 6.30 (s, 1H); 4.15 (bs, 2H), 3.8 (bs, 1H), 3.60 (s, 3H), 2.64 (s, 3H).

Intermediate 2: 4-amino-1-ethyl-3-(methylamino)-6-(trifluoromethyl)pyridin-2-one

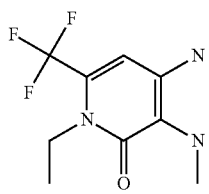

Step A: 1-ethyl-3-(methylamino)-6-(trifluoromethyl)pyridin-2-one

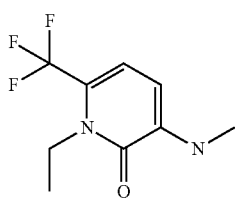

To a solution of 3-amino-1-ethyl-6-(trifluoromethyl)pyridin-2-one (5.00 g, 24.3 mmol, Commercially available or synthesised by analogy with literature, for example, Synthesis 2005, No. 8, pp 1269-1278 and Synthesis 2011, No. 7, pp 1149-1156) in acetonitrile (150 mL) was added formaldehyde (37 mass %) in aq solution (14.5 ml, 194 mmol) and acetic acid (6.96 ml, 121 mmol). The resulting suspension stirred for 1 hour, then sodium cyanoborohydride (6.42 g, 97.0 mmol) was added in 5 portions over 3 hours and the mixture was stirred over night. The solution was diluted with water and extracted with ethyl acetate (3×). The combined organic layer was dried over Na$_2$SO$_4$, filtered, concentrated and purified by column chromatography using cyclohexane-ethyl acetate (100-200 silica gel) to give the desired compound as a white solid. $^1$H NMR (400 MHz, CDCl$_3$) δ ppm 6.70 (d, 1H), 6.04 (d, 1H), 5.44 (sb, 1H), 4.15 (q, 2H), 2.85 (s, 3H), 1.32 (t, 3H).

Step B: 1-ethyl-3-(methylamino)-4-nitro-6-(trifluoromethyl)pyridin-2-one

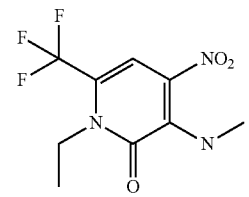 [SMILES: CCn1c(C(F)(F)F)cc([N+](=O)[O-])c(NC)c1=O]

The 1-ethyl-3-(methylamino)-4-nitro-6-(trifluoromethyl)pyridin-2-one was prepared as for Example 3, step B. LC-MS (Method A): RT 0.98, 266 (M+H$^+$), 264 (M−H$^+$).

Step C: 4-amino-1-ethyl-3-(methylamino)-6-(trifluoromethyl)pyridin-2-one

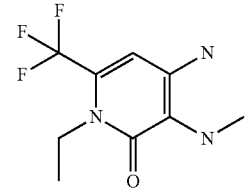 [SMILES: CCn1c(C(F)(F)F)cc(N)c(NC)c1=O]

The 4-amino-1-ethyl-3-(methylamino)-6-(trifluoromethyl)pyridin-2-one was prepared as for Example 3, step C. LC-MS (Method A): RT 0.47, 236 (M+H$^+$).

Intermediate 3: 4-bromo-2-(4-chlorophenyl)thiazole-5-carboxylic acid

Step A: Preparation of 4-bromo-2-(4-chlorophenyl)thiazole

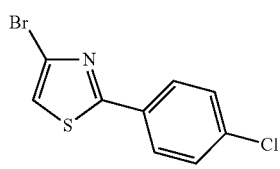 [SMILES: Clc1ccc(-c2nc(Br)cs2)cc1]

A mixture of 2,4-dibromothiazole (482 mg, 2 mmol), Pd(PPh$_3$)$_4$ (116 mg, 0.1 mmol), cesium carbonate (978 mg, 3 mmol) and 4-chlorophenylboronic acid (312 mg, 2 mmol) dissolved in 20 ml of DME and 10 ml of H$_2$O was refluxed for 16 h under nitrogen. After this time, the mixture was diluted with water and extracted with ethyl acetate three times. The combined organic layers were dried over sodium sulfate, filtered and concentrated in vacuo. The residue was purified by flash column chromatography on silica gel to give the title compound.

$^1$H NMR (400 MHz, DMSO-d6): δ 7.59 (d, 2H), 7.94 (d, 2H), 7.95 (s, 1H); EI-MS: 273/275 (M).

Step B: Preparation of 4-bromo-2-(4-chlorophenyl)thiazole-5-carboxylic acid

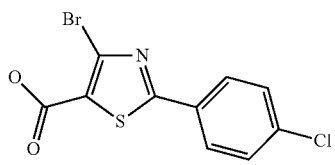 [SMILES: O=C(O)c1sc(-c2ccc(Cl)cc2)nc1Br]

A solution of i-Pr$_2$NH (253 mg, 2.5 mmol) in 5 ml of THF was treated dropwise with n-BuLi (1 mL, 2.5 mmol; 2.5M in hexane) at −60° C. under nitrogen. After the addition, 4-Bromo-2-(4-chlorophenyl)thiazole (546 mg, 2 mmol) dissolved in 2 mL of THF, was added slowly to the reaction mixture, and stirring continued for a further 20 min. The reaction mixture was then poured into dry ice and stirred until the dry ice dissolved. The reaction mixture was poured into dilute hydrochloric acid and extracted with ethyl acetate three times. The combined organic layers were dried over sodium sulfate, filtered and concentrated in vacuo. The residue was purified by flash column chromatography on silica gel to give the title product as a white solid. $^1$H NMR (400 MHz, DMSO-d6): δ 7.61 (d, 2H), 8.01 (d, 2H).

Intermediate 4: Preparation of 3-ethylsulfanyl-5-iodo-thiophene-2-carboxylic acid Step A: Preparation of 3-ethylsulfanylthiophene-2-carboxylic acid

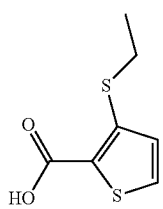

A solution of 3-bromothiophene-2-carboxylic acid (CAS: 7311-64-0, 10.35 g, 50 mmol) and EtSNa (12.6 g, 150 mmol) in 60 ml of DMF was refluxed for 4 hours. Then, the mixture was poured into dilute hydrochloric acid and extracted with ethyl acetate three times. The combined organic layers were dried over sodium sulfate, filtered and concentrated under vacuum. The residue was purified by flash column chromatography on silica gel to give the title compound.

$^1$H NMR (400 Mz, DMSO-d$_6$): δ 1.28 (t, 3H), 3.04 (q, 2H), 7.16 (d, 1H), 7.86 (d, 1H), 12.91 (s, 1H).

Step B: Preparation of methyl 3-ethylsulfanylthiophene-2-carboxylate

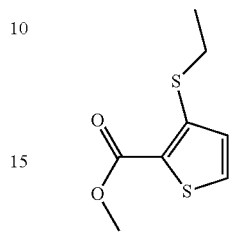

Diazomethane (30 mL, 15 mmol, 0.5 mol/L in diethyl ether) was added to a solution of compound 3-ethylsulfanylthiophene-2-carboxylic acid (1.88 g, 10 mmol) in diethyl ether (50 mL) at ambient temperature. The mixture was stirred at ambient temperature for 2 hours and poured into dilute hydrochloric acid, and extracted three times with ethyl acetate. The combined organic layers were dried over sodium sulfate, filtered and concentrated under vacuum. The residue was purified by flash column chromatography on silica gel to give the title product.

$^1$H NMR (400 Mz, DMSO-d$_6$): δ 1.29 (t, 3H), 3.05 (q, 2H), 3.78 (s, 3H), 7.21 (d, 1H), 7.93 (d, 1H).

Step C: Preparation of methyl 3-ethylsulfanyl-5-iodo-thiophene-2-carboxylate

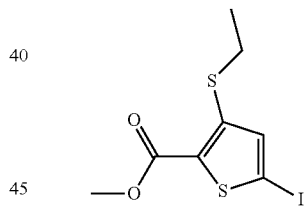

To a solution of diisopropylamine (3.03 g, 30 mmol) in 40 mL of dry tetrahydrofurane at −78° C. was added n-butyllithium (12 mL, 30 mmol, 2.5 M in hexane) under a nitrogen atmosphere. After stirring for 25 min. at −78° C., a solution of methyl 3-ethylsulfanylthiophene-2-carboxylate (5.05 g, 25 mmol) in 20 mL of dry tetrahydrofurane was added slowly during a 10 min period. The mixture was then allowed to stand at −78° C. for an additional 20 min and then treated with a solution of iodine (7 g, 27.5 mmol) in 20 mL of dry tetrahydrofurane. The cooling bath was removed and the solution was allowed to warm to ambient temperature over 1 h. The reaction mixture was then acidified with 1 M HCl and 100 mL of ether was added. The aqueous layer was extracted with ether (3×100 mL) and the combined organic layers were washed with water, dried over MgSO$_4$, and concentrated under vacuum. The residue was purified by flash column chromatography on silica gel to give the title product.

$^1$H NMR (400 Mz, DMSO-d$_6$): δ 1.26 (t, 3H), 3.06 (q, 2H), 3.76 (s, 3H), 7.44 (s, 1H).

Step D: Preparation of 3-ethylsulfanyl-5-iodo-thiophene-2-carboxylic acid

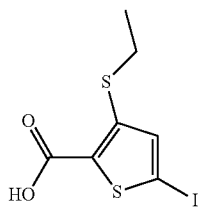

A mixture of methyl 3-ethylsulfanyl-5-iodo-thiophene-2-carboxylate (3.28 g, 10 mmol) and LiOH (480 mg, 20 mmol) in 30 ml of water and 30 ml of THF was stirred at ambient temperature for 16 h. The reaction mixture was then poured into diluted hydrochloric acid and extracted with ethyl acetate three times. The combined organic layers were dried over sodium sulfate, filtered and concentrated under vacuum. The residue was purified by flash column chromatography on silica gel to provide the title product.

$^1$H NMR (400 Mz, DMSO-d$_6$): δ 1.26 (t, 3H), 3.02 (q, 2H), 7.38 (s, 1H), 13.05 (s, 1H).

Intermediate 5: 2-bromo-5-ethylsulfanyl-thiazole-4-carboxylic acid

Step A: Preparation of ethyl 5-ethylsulfanylthiazole-4-carboxylate

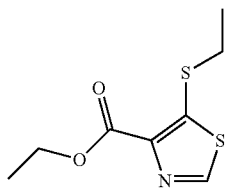

As described in WO15000715, A solution of ethyl isocyanoacetate (5.6 g, 0.05 mol) in 100 ml of THF was added dropwise to a suspension of potassium tert-butoxide (6.1 g, 0.055 mol) in 20 ml of THF at −40° C. The mixture was cooled to −60° C., and a solution of carbon disulfide (3.8 g, 0.05 mol) was added dropwise while keeping the temperature below −50° C. The mixture was warmed to 10° C. and ethyl bromide (5.4 g, 0.05 mol) was added. The mixture was allowed to stir for 2 h and was concentrated in vacuum. The product was purified by column chromatography on silica gel to get the title compound.

$^1$H NMR (400 MHz, DMSO-d$_6$) δ 1.27-1.37 (m, 6H), 3.03-3.10 (q, 2H), 4.25-4.32 (q, 2H), 8.92 (s, 1H).

Step B: Preparation of ethyl 2-bromo-5-ethylsulfanyl-thiazole-4-carboxylate

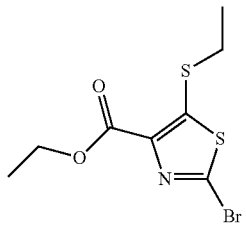

Bromine (0.48 g, 3 mmol) was added to the solution of ethyl 5-ethylsulfanylthiazole-4-carboxylate (219 mg, 1 mmol) in 10 ml of CCl$_4$ at 0° C. The mixture was stirred overnight at r.t, the mixture was poured into water, and extracted with dichloromethane three times. The combined organic layers were dried over sodium sulfate, filtered and concentrated in vacuo. The crude product was purified by column chromatography on silica gel to give the title compound.

$^1$H-NMR (400 Mz, DMSO-d$_6$) δ: δ 1.32-1.24 (m, 6H), 3.03-3.00 (q, 2H), 4.27-4.21 (q, 2H).

Step C: Preparation of 2-bromo-5-ethylsulfanyl-thiazole-4-carboxylic acid

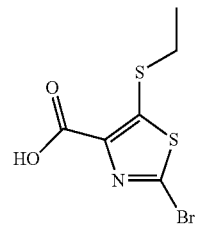

A mixture of ethyl 2-bromo-5-ethylsulfanyl-thiazole-4-carboxylate (2.92 g, 9.8 mol) and NaOH (780 mg, 19.6 mol) in 20 ml of water and 40 ml of THF was stirred at room temperature overnight. The reaction mixture was poured into diluted hydrochloric acid and concentrated in vacuo. Then, the deposited precipitate was filtrated, washed with water three times, and concentrated in vacuo, to obtain the title compound.

$^1$H NMR (400 MHz, DMSO-d$_6$) δ 1.31-1.18 (t, 3H), 3.03-2.97 (q, 2H), 13.32 (s, 1H);

Example P1: Preparation of 2-[5-(4-chlorophenyl)-3-ethylsulfanyl-2-thienyl]-5-ethyl-3-methyl-6-(trifluoromethyl)-3aH-imidazo[4,5-c]pyridin-4-one A1

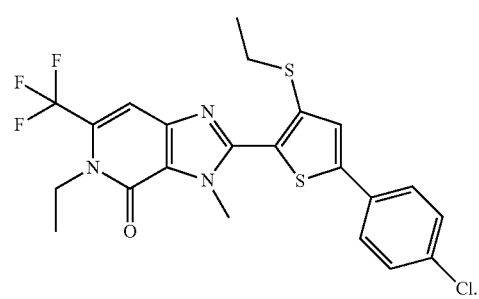

Step A: Preparation of N-[4-amino-1-ethyl-2-oxo-6-(trifluoromethyl)-3-pyridyl]-5-(4-chlorophenyl)-3-ethylsulfanyl-N-methyl-thiophene-2-carboxamide and 5-(4-chlorophenyh-N-[1-ethyl-3-(methylamino)-2-oxo-6-(trifluoromethyl)-3H-pyridin-4-yl]-3-ethyl-sulfanyl-thiophene-2-carboxamide

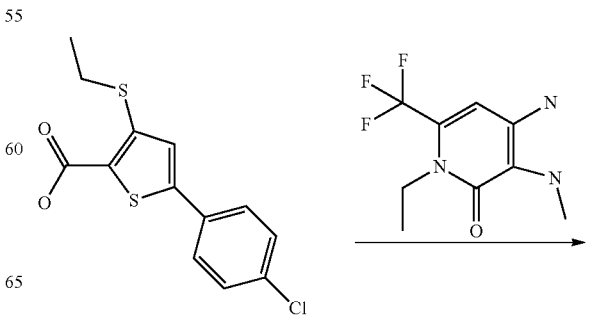

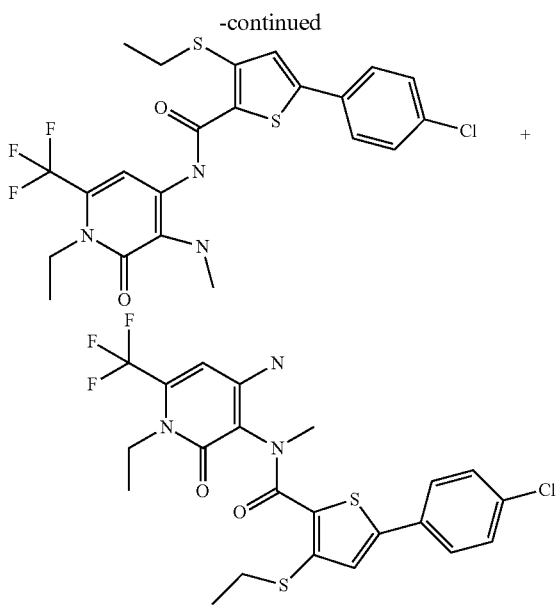

5-(4-chlorophenyl)-3-ethylsulfanyl-thiophene-2-carboxylic acid (209 mg, 0.701 mmol) was dissolved in dichloromethane (1.14 mL) and was added of oxalyl dichloride (0.125 mL, 1.40 mmol) and N,N-dimethylformamide (1 drop). The mixture was stirred for 30 min at room temperature then at reflux for 30 min. The solvent was removed and dried by vacuum.

The 5-(4-chlorophenyl)-3-ethylsulfanyl-thiophene-2-carbonyl chloride (222 mg, 0.701 mmol) was diluted with 0.5 ml of THF and added at a mixture of 4-amino-1-ethyl-3-(methylamino)-6-(trifluoromethyl)-3H-pyridin-2-one (Prepared in Intermediate 2, 150 mg, 0.64 mmol) in tetrahydrofuran (1.28 mL) and pyridine (0.15 mL, 1.91 mmol). The mixture was stirred at reflux for 3 hours. The solution was diluted with a saturated solution of sodium carbonate and ethyl acetate. the aqueous phase was extracted with ethyl acetate (2×). The combined organic layer was dried over $Na_2SO_4$, filtered, concentrated and purified by column chromatography using cyclohexane-ethyl acetate to give the desired compounds (180 mg). The mixture was used without extra purification for the next step. LC-MS (Method A): RT 1.09, 516 (M+H$^+$).

Step B: Preparation of 2-[5-(4-chlorophenyl)-3-ethylsulfanyl-2-thienyl]-5-ethyl-3-methyl-6-(trifluoromethyl)-3aH-imidazo[4,5-c]pyridin-4-one A1

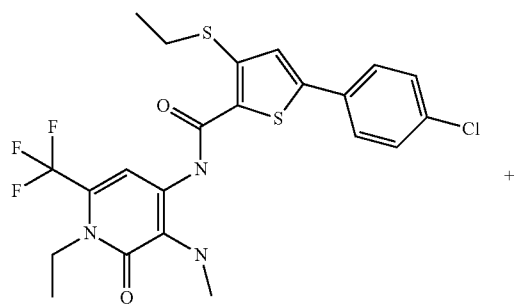

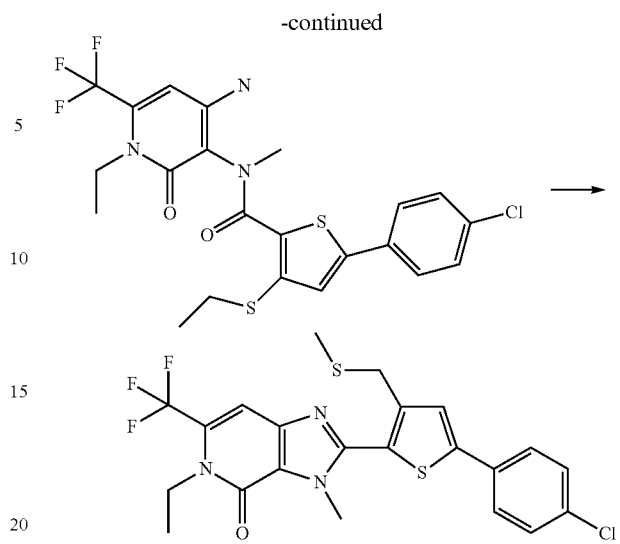

A microwave vial was charged with a mixture of of N-[4-amino-1-ethyl-2-oxo-6-(trifluoromethyl)-3-pyridyl]-5-(4-chlorophenyl)-3-ethylsulfanyl-N-methyl-thiophene-2-carboxamide and 5-(4-chlorophenyl)-N-[1-ethyl-3-(methylamino)-2-oxo-6-(trifluoromethyl)-3H-pyridin-4-yl]-3-ethylsulfanyl-thiophene-2-carboxamide (0.14 g, 0.2713 mmol) acetic acid (1.36 mL). Then, the mixture was stirred for 15' at 140° C. under microwaves then 40' at 150° C. The reaction mixture was diluted with water (10 mL) and extracted two time with ethyl acetate. The combined organic phases were washed with water and dried over sodium sulfate and concentrated under vacuum. The residue was subjected to column chromatography, eluting with ethyl acetate/cyclohexane. The selected fractions were evaporated to yield the title compound (81 mg). LC-MS (Method A): RT 1.32, 498 (M+H$^+$).

Step C: Preparation of 2-[5-(4-chlorophenyl)-3-ethylsulfonyl-2-thienyl]-5-ethyl-3-methyl-6-(trifluoromethyl)-3aH-imidazo[4,5-c]pyridin-4-one A2

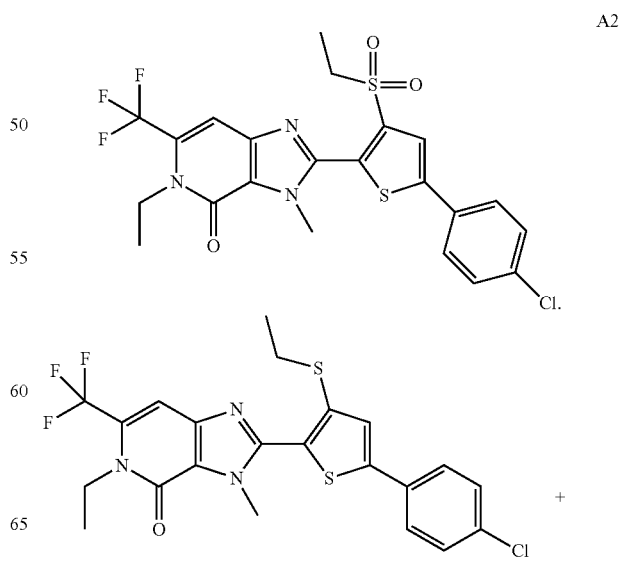

-continued

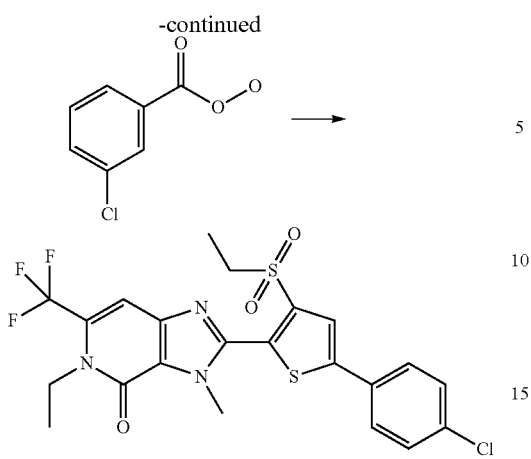

A solution of 2-[5-(4-chlorophenyl)-3-ethylsulfanyl-2-thienyl]-5-ethyl-3-methyl-6-(trifluoromethyl)-3aH-imidazo[4,5-c]pyridin-4-one (A1, 2.003Y4) (preparation described before, 80 mg, 0.16 mmol) in dichloromethane (3.2 ml) was added mCPBA (70 wt % in water) (95.05 mg, 0.386 mmol) in one portion and mixture was stirred at ambient temperature for 2 h. The reaction mixture was diluted with dichloromethane and water, then after separation, the organic phase was washed with a solution of NaOH 1M, water and brine. The organic phase is dried over sodium sulfate and concentrated under vacuum to afford the title compound (60 mg) as a solid. LC-MS (method A): RT 1.19, 530 (M+H$^+$).

Example P2: Preparation of 5-ethyl-2-(3-ethylsulfanyl-5-iodo-2-thienyl)-3-methyl-6-(trifluoromethyl) imidazo[4,5-c]pyridin-4-one A39 and 5-ethyl-2-(3-ethylsulfonyl-5-iodo-2-thienyl)-3-methyl-6-(trifluoromethyl)imidazo[4,5-c]pyridin-4-one A40

Step A: Preparation of N-[4-amino-1-ethyl-2-oxo-6-(trifluoromethyl)-3-pyridyl]-3-ethylsulfanyl-5-iodo-N-methyl-thiophene-2-carboxamide

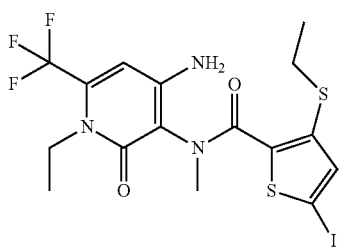 [SMILES: CCSc1cc(I)sc1C(=O)N(C)c1c(N)cc(C(F)(F)F)n(CC)c1=O]

3-ethylsulfanyl-5-iodo-thiophene-2-carboxylic acid (1.3 g, 4.1 mmol) was dissolved in dichloromethane (20 mL) and 2 drops of dimethylformamide were added. Oxalyl dichloride (0.46 mL, 5.4 mmol) was added and the reaction mixture was stirred at room temperature overnight. Then the reaction mixture was evaporated to give 3-ethylsulfanyl-5-iodo-thiophene-2-carbonyl chloride as intermediate 1. 4-amino-1-ethyl-3-(methylamino)-6-(trifluoromethyl)pyridin-2-one (0.55 g, 2.3383 mmol) was suspended in ethylacetate (23 mL) and triethylamine (0.81 mL, 5.84 mmol) was added. The intermediate 1 was dissolved in ethylacetate (5 mL) and added at 0° C. via a dropping funnel. The resulting mixture was warm up to room temperature and stirred for 5 hours. The reaction mixture was extracted with ethylacetate and HCl 1N. The organic layer was washed with NaHCO$_3$ saturated solution and brine, dried over Na$_2$SO$_4$ and concentrated under vacuum. The crude product was purified by flash chromatography to give the title compound (0.902 g) as a solid. LC-MS (method A): RT 0.97, 532 (M+H+).

Step B: Preparation of 5-ethyl-2-(3-ethylsulfanyl-5-iodo-2-thienyl)-3-methyl-6-(trifluoromethyl)imidazo[4,5-c]pyridin-4-one A39

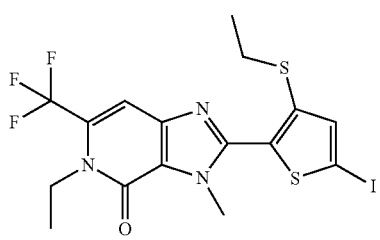 [SMILES: CCSc1cc(I)sc1-c1nc2cc(C(F)(F)F)n(CC)c(=O)c2n1C]

In a microwave vial, N-[4-amino-1-ethyl-2-oxo-6-(trifluoromethyl)-3-pyridyl]-3-ethylsulfanyl-5-iodo-N-methyl-thiophene-2-carboxamide (0.900 g, 1.69 mmol) was suspended in acetic acid (9.00 mL) and the resulting mixture was irradiated to 160° C. for 2 hours. The reaction mixture was poured into water and the white brown suspension obtained was filtered. The brown filter cake was washed with water and then the solid was dissolved in ethylacetate, dried over Na$_2$SO$_4$, filtered and evaporated. To remove the excess of acetic acid, the solid was dissolved again in ethylacetate, dried over Na$_2$SO$_4$, filtered and evaporated to give the title compound (0.79 g). LC-MS (method A): RT 1.24, 514 (M+H+). Mp: 120-123° C.

Step C: Preparation of 5-ethyl-2-(3-ethylsulfonyl-5-iodo-2-thienyl)-3-methyl-6-(trifluoromethyl) imidazo[4,5-c]pyridin-4-one A40

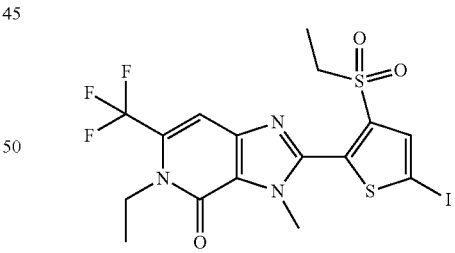

5-ethyl-2-(3-ethylsulfanyl-5-iodo-2-thienyl)-3-methyl-6-(trifluoromethyl)imidazo[4,5-c]pyridin-4-one (0.709 g, 1.381 mmol) was dissolved in chloroform (17.5 mL) and the resulting mixture was cooled to 0° C., under argon. MCPBA (0.7739 g, 3.453 mmol) was added and the mixture was warm up to room temperature and stirred overnight. LC-MS analysis showed reaction completion. Na$_2$S$_2$O$_3$ sat sol was added and the resulting mixture was stirred for 1 hour at room temperature and extracted with dichloromethane. The organic phase was washed with NaHCO$_3$ sat solution, dried over Na$_2$SO$_4$, filtered and evaporated. The crude was purified by flash chromatography over silica gel to give the title compound (0.63 g) as a solid. LC-MS (method A): RT 1.06, 546 (M+H+). Mp: 165-166° C.

The 2-(3-ethylsulfanyl-5-iodo-2-thienyl)-3,5-dimethyl-6-(trifluoromethyl)imidazo[4,5-c]pyridin-4-one A43 and 2-(3-ethylsulfonyl-5-iodo-2-thienyl)-3,5-dimethyl-6-(trifluoromethyl)imidazo[4,5-c]pyridin-4-one A44

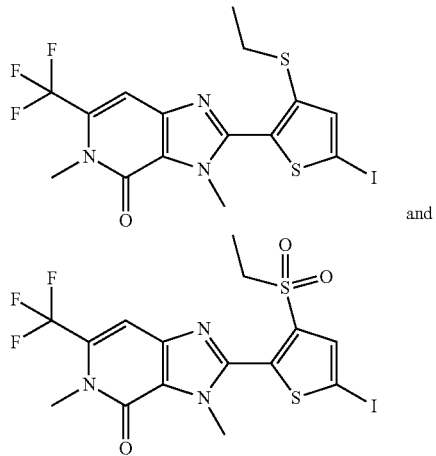

and were prepared using intermediate 1 and intermediate 4 with and a similar protocol:

2-(3-ethylsulfanyl-5-iodo-2-thienyl)-3,5-dimethyl-6-(trifluoromethyl)imidazo[4,5-c]pyridin-4-one A43: $^1$H NMR (400 MHz, CDCl$_3$) δ ppm 7.25 (s, 2H), 4.12 (s, 3H), 3.72 (s, 3H), 2.84 (q, 2H), 1.22 (t, 3H)

2-(3-ethylsulfonyl-5-iodo-2-thienyl)-3,5-dimethyl-6-(trifluoromethyl)imidazo[4,5-c]pyridin-4-one A44: $^1$H NMR (400 MHz, CDCl$_3$) δ ppm 7.70 (s, 1H), 7.20 (s, 1H), 4.05 (s, 3H), 3.70 (s, 3H), 3.34 (q, 2H), 1.28 (t, 3H)

The 2-(2-bromo-5-ethylsulfanyl-thiazol-4-yl)-3,5-dimethyl-6-(trifluoromethyl)imidazo[4,5-c]pyridin-4-one A46 and 2-(2-bromo-5-ethylsulfonyl-thiazol-4-yl)-3,5-dimethyl-6-(trifluoromethyl)imidazo[4,5-c]pyridin-4-one A47

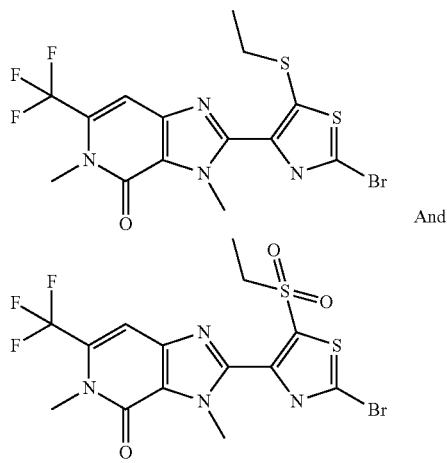

And were prepared using intermediate 1 and intermediate 5 with and a similar protocol:

2-(2-bromo-5-ethylsulfanyl-thiazol-4-yl)-3,5-dimethyl-6-(trifluoromethyl)imidazo[4,5-c]pyridin-4-one A46: $^1$H NMR (400 MHz, CDCl$_3$) δ ppm 7.32 (s, 1H), 4.38 (s, 3H), 3.72 (s, 3H), 3.04 (q, 2H), 1.38 (t, 3H)

2-(2-bromo-5-ethylsulfonyl-thiazol-4-yl)-3,5-dimethyl-6-(trifluoromethyl)imidazo[4,5-c]pyridin-4-one A47: $^1$H NMR (400 MHz, CDCl$_3$) δ ppm 7.22 (s, 1H), 4.30 (s, 3H), 4.04 (q, 2H), 3.72 (s, 3H), 1.46 (t, 3H)

Example P3: Preparation of 5-ethyl-2-[3-ethylsulfonyl-5-(3-fluorophenyl)-2-thienyl]-3-methyl-6-(trifluoromethyl)imidazo[4,5-c]pyridin-4-one A41

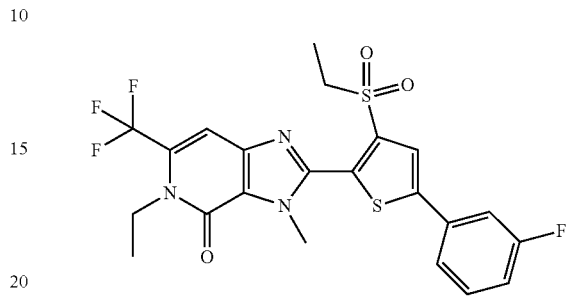

(3-fluorophenyl)boronic acid (61 mg, 0.4401 mmol) was suspended in tetrahydrofuran (3.6 mL) and water (1.2 mL), in a 25 mL three neck flask under argon. 5-ethyl-2-(3-ethylsulfonyl-5-iodo-2-thienyl)-3-methyl-6-(trifluoromethyl)imidazo[4,5-c]pyridin-4-one (200 mg, 0.3668 mmol) was added and the mixture was degassed for 30 min. XPHOS PALLADACYCLE GEN 2 (2.9 mg, 0.003668 mmol) was added and the yellow mixture was degassed for 20 min again. Sodium carbonate (2M, 0.3668 mL) was degassed for 40 min and added to the mixture. The resulting mixture was heated to 50° C. (IT). The mixture was stirred overnight. After heating 24 h, LC-MS analysis showed reaction completion. The reaction mixture was cooled to room temperature, diluted with ethylacetate, and washed with a saturated NaHCO$_3$ solution and brine. The organic phases were dried over Na$_2$SO$_4$, filtered and evaporated. The crude product was purified by flash chromatography over silica gel to give the title compound (143 mg) as a solid. LC-MS (method A): RT 1.15, 514 (M+H$^+$). Mp: 194-195° C.

Example P4: Preparation of 2-[5-(3,5-difluorophenyl)-3-ethylsulfonyl-2-thienyl]-5-ethyl-3-methyl-6-(trifluoromethyl)imidazo[4,5-c]pyridin-4-one A42

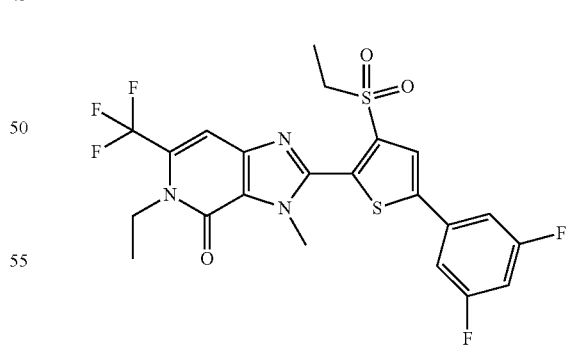

3,5-difluorobenzeneboronic acid (70.92 mg, 0.4401 mmol) was suspended in tetrahydrofuran (3.6 mL) and water (1.2 mL), in a 25 mL three neck flask under argon. 5-ethyl-2-(3-ethylsulfonyl-5-iodo-2-thienyl)-3-methyl-6-(trifluoromethyl)imidazo[4,5-c]pyridin-4-one (200 mg, 0.3668 mmol) was added and the mixture was degassed for 30 min. XPHOS PALLADACYCLE GEN 2 (2.9 g, 0.003668 mmol) was added and the yellow mixture was degassed for 20 min again. Sodium carbonate (2M, 0.3668 mL) was degassed for 40 min and added to the mixture. The resulting mixture was heated to 50° C. (IT). The mixture was stirred overnight. After heating 24 h, LC-MS analysis showed reaction completion. The reaction mixture was cooled to room temperature, diluted with ethylacetate, and washed with a saturated NaHCO3 solution and brine. The organic phases were dried over Na2SO4, filtered and evaporated. The crude product was purified by flash chromatography over silica gel to give the title compound (109 mg) as a solid. LC-MS (method A): RT 1.17, 532 (M+H+). Mp: 180-182° C.

Example P5: Preparation of 2-[2-(4-chlorophenyl)-5-ethylsulfonyl-thiazol-4-yl]-3,5-dimethyl-6-(trifluoromethyl)imidazo[4,5-c]pyridin-4-one A48

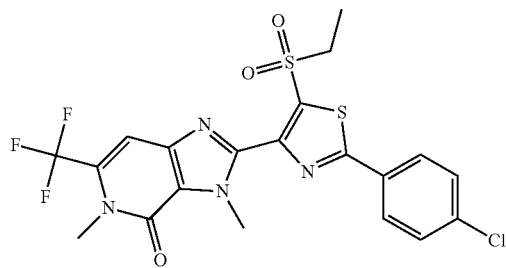 [SMILES: CCS(=O)(=O)c1sc(-c2ccc(Cl)cc2)nc1-c1nc2cc(C(F)(F)F)n(C)c(=O)c2n1C]

A solution of 2-(2-bromo-5-ethylsulfonyl-thiazol-4-yl)-3,5-dimethyl-6-(trifluoromethyl)imidazo[4,5-c]pyridin-4-one A47 (preparation described before, 0.100 g, 0.206 mmol) in a mixture of water (1.5 mL) and toluene (1.5 mL) was added potassium phosphate tribasic (0.271 g, 1.24 mmol), (4-chlorophenyl)boronic acid (0.118 g, 0.742 mmol) in a vial. The vial was flushed with argon and tetrakis(triphenylphosphine)palladium(0) (0.0119 g, 0.0103 mmol) was added. The reaction mixture was stirred at reflux for 2 hours. The reaction mixture was diluted with water and extracted two times with ethyl acetate. The combined organic phases were washed with brine (2 times) and dried over sodium sulfate and concentrated under vacuum. The residue was subjected to column chromatography over silica gel, eluting with ethyl acetate/cyclohexane to give the title compound (0.02 g) that was sum it to purification via HPLC to give 8 mg of the desired product (90% purity). $^1$H NMR (400 MHz, CHLOROFORM-d) δ ppm 1.48 (t, 3H), 3.73 (s, 3H), 4.01 (q, 2H), 4.35 (s, 3H), 7.25 (s, 1H), 7.48-7.53 (m, 2H), 7.91-7.97 (m, 2H).

Example P6: Preparation of Compound A3 to A29

Protocol:

Boronic acids (2 eq.) were weighed manually into a conical microwave vial. 0.3 mL DME was added with a multipipette into the vials. A stock solution of the scaffold A44 was prepared by mixing 87.35 mg in 3.6 mL DME and 0.3 mL of this solution was dispensed into vials. Then, 0.3 mL of water was added to the vials. A solution of Na$_2$CO$_3$ (2 M) was prepared (2.12 g in10 mL of water) and 40 uL of this solution was distributed in vials.

A stock suspension of the X-Phos precatalyst Buchwald 2nd Generation (0.1 eq.) was prepared by mixing 14.16 mg in 3.6 mL. 0.3 mL of this solution was dispensed into vials.

The vials were flushed with argon and capped.

Reaction take place in a microwave oven at 100° C. for 10 min. Then, the solvent was evaporated and the crude diluted in water, then extracted 3 times extractions ethyl acetate. After evaporation, the crude was purification on a reverse phase preparative system.

QC method: Spectra were recorded on a Mass Spectrometer (ACQUITY UPLC) from Waters (SQD, SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/hr, Desolvation Gas Flow: 700 L/hr, Mass range: 140 to 800 Da), DAD Wavelength range (nm): 210 to 400, and an Acquity UPLC from Waters: Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=Water/Methanol 9:1, 0.1% formic acid, B=Acetonitrile+0.1% formic acid, gradient: 0-100% B in 2.5 min; Flow (ml/min) 0.75

|  | RT | M (calculated) | (M + H)$^+$ (measured) |
|---|---|---|---|
| A3 | 1.74 | 499.06 | 500.08 |
| A4 | 1.85 | 527.06 | 528.09 |
| A5 | 1.25 | 483.06 | 484.06 |
| A6 | 1.73 | 481.07 | 482.32 |
| A7 | 1.84 | 549.06 | 550.29 |
| A8 | 1.86 | 515.04 | 516.04 |
| A9 | 1.69 | 487.03 | 488.19 |
| A10 | 1.92 | 565.06 | 566.17 |
| A11 | 1.68 | 550.06 | 551.08 |
| A12 | 1.79 | 517.06 | 518.05 |
| A13 | 1.75 | 499.06 | 500.24 |
| A14 | 1.87 | 525.10 | 526.35 |
| A15 | 1.90 | 533.03 | 534.03 |
| A16 | 2.19 | 627.05 | 628.04 |
| A17 | 1.60 | 506.07 | 507.06 |
| A18 | 1.17 | 482.07 | 483.29 |
| A19 | 1.93 | 565.06 | 566.16 |
| A20 | 1.73 | 529.08 | 530.08 |
| A21 | 1.63 | 445.07 | 446.28 |
| A22 | 1.98 | 529.05 | 530.06 |
| A23 | 1.81 and 1.85 | 507.09 | 508.33 |
| A24 | 1.41 | 513.08 | 514.21 |
| A25 | 1.59 | 506.07 | 507.27 |
| A26 | 1.92 | 567.05 | 568.17 |
| A27 | 1.77 | 517.06 | 518.30 |
| A28 | 2.02 | 617.05 | 618.29 |
| A29 | 1.76 | 517.06 | 518.22 |

Example P7: Preparation of Compound A30 to A38

Protocol:

Boronic acids (2 eq.) were weighed manually into a conical microwave vial and 0.3 mL DME was added with a multipipette into the vials.

A stock solution of the scaffold A47 was prepared by mixing 87.35 mg in 3.6 mL DME. Then, 0.3 mL of this solution was dispensed into vials. 0.3 mL H$_2$O was added into the vials.

A solution of Na$_2$CO$_3$ (2 M) was prepared (2.12 g in10 mL H$_2$O) and 40 uL was added into the vials.

A stock suspension of the X-Phos precatalyst Buchwald 2nd Generation (0.1 eq.) was prepared by mixing 14.16 mg in 3.6 mL and 0.3 mL of this solution was dispensed into vials.

The vials were flushed with argon and capped.

Reaction take place in a microwave oven at 100° C. for 10 min. Then, the solvent was evaporated and the crude diluted in water, then extracted 3 times extractions ethyl acetate. After evaporation, the crude was purification on a reverse phase preparative system.

QC method: Spectra were recorded on a Mass Spectrometer (ACQUITY UPLC) from Waters (SQD, SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/hr, Desolvation Gas Flow: 700 L/hr, Mass range: 140 to 800 Da), DAD Wavelength range (nm): 210 to 400, and an Acquity UPLC from Waters: Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=Water/Methanol 9:1, 0.1% formic acid, B=Acetonitrile+0.1% formic acid, gradient: 0-100% B in 2.5 min; Flow (ml/min) 0.75

|  | RT | M (calculated) | $(M + H)^+$ (measured) |
|---|---|---|---|
| A30 | 1.84 | 482.07 | 483.07 |
| A31 | 1.45 | 483.06 | 484.25 |
| A32 | 1.21 | 486.08 | 487.30 |
| A33 | 1.42 | 486.08 | 487.07 |
| A34 | 1.82 | 551.05 | 552.07 |
| A35 | 1.86 | 500.06 | 501.05 |
| A36 | 1.72 | 507.06 | 508.06 |
| A37 | 1.50 | 489.02 | 490.00 |
| A38 | 1.75 | 488.03 | 489.08 |

Table 5: This table discloses preferred compounds of the formula I-1b:

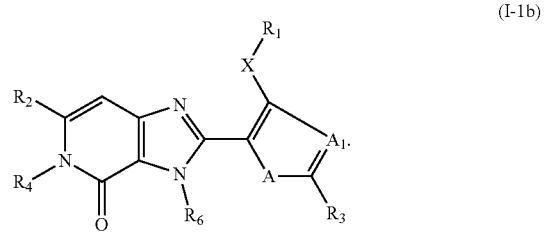

TABLE 5

| Comp. No. | $R_6$ | X | $R_1$ | A | $R_2$ | $R_4$ | $A_1$ | $R_3$ |
|---|---|---|---|---|---|---|---|---|
| A1 (2.001 Y4) | $CH_3$ | S | $-CH_2CH_3$ | S | $CF_3$ | $CH_3$ | CH | 4-Cl-phenyl |
| A2 (2.002 Y4) | $CH_3$ | $SO_2$ | $-CH_2CH_3$ | S | $CF_3$ | $CH_3$ | CH | 4-Cl-phenyl |
| A3 | $CH_3$ | $SO_2$ | $-CH_2CH_3$ | S | $CF_3$ | $CH_3$ | CH | 4-F-phenyl |
| A4 | $CH_3$ | $SO_2$ | $-CH_2CH_3$ | S | $CF_3$ | $CH_3$ | CH | 3-(SMe)-phenyl |
| A5 | $CH_3$ | $SO_2$ | $-CH_2CH_3$ | S | $CF_3$ | $CH_3$ | CH | pyrimidin-5-yl |
| A6 (2.002 Y1) | $CH_3$ | $SO_2$ | $-CH_2CH_3$ | S | $CF_3$ | $CH_3$ | CH | phenyl |

TABLE 5-continued
| Comp. No. | R$_6$ | X | R$_1$ | A | R$_2$ | R$_4$ | A$_1$ | R$_3$ |
|---|---|---|---|---|---|---|---|---|
| A7 (2.002 Y5) | CH$_3$ | SO$_2$ | —CH$_2$CH$_3$ | S | CF$_3$ | CH$_3$ | CH | 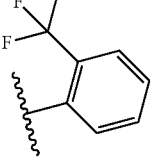 |
| A8 (2.002 Y3) | CH$_3$ | SO$_2$ | —CH$_2$CH$_3$ | S | CF$_3$ | CH$_3$ | CH | 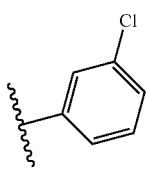 |
| A9 | CH$_3$ | SO$_2$ | —CH$_2$CH$_3$ | S | CF$_3$ | CH$_3$ | CH | 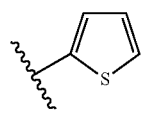 |
| A10 | CH$_3$ | SO$_2$ | —CH$_2$CH$_3$ | S | CF$_3$ | CH$_3$ | CH | 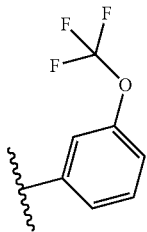 [SMILES: *c1cccc(OC(F)(F)F)c1] |
| A11 | CH$_3$ | SO$_2$ | —CH$_2$CH$_3$ | S | CF$_3$ | CH$_3$ | CH | 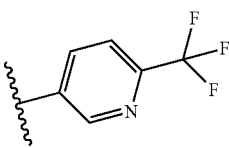 [SMILES: *c1ccc(C(F)(F)F)nc1] |
| A12 | CH$_3$ | SO$_2$ | —CH$_2$CH$_3$ | S | CF$_3$ | CH$_3$ | CH | 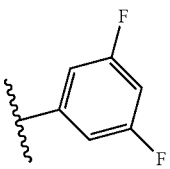 [SMILES: *c1cc(F)cc(F)c1] |
| A13 | CH$_3$ | SO$_2$ | —CH$_2$CH$_3$ | S | CF$_3$ | CH$_3$ | CH | 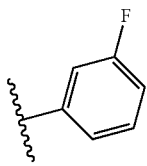 [SMILES: *c1cccc(F)c1] |
| A14 | CH$_3$ | SO$_2$ | —CH$_2$CH$_3$ | S | CF$_3$ | CH$_3$ | CH | 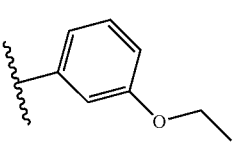 [SMILES: *c1cccc(OCC)c1] |
| A15 | CH$_3$ | SO$_2$ | —CH$_2$CH$_3$ | S | CF$_3$ | CH$_3$ | CH | 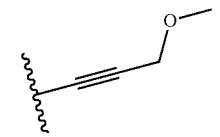 [SMILES: *C#CCOC] |

TABLE 5-continued
| Comp. No. | R$_6$ | X | R$_1$ | A | R$_2$ | R$_4$ | A$_1$ | R$_3$ |
|---|---|---|---|---|---|---|---|---|
| A16 | CH$_3$ | SO$_2$ | —CH$_2$CH$_3$ | S | CF$_3$ | CH$_3$ | CH | 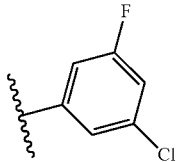 [SMILES: *c1cc(F)cc(Cl)c1] |
| A17 (2.002 Y11) | CH$_3$ | SO$_2$ | —CH$_2$CH$_3$ | S | CF$_3$ | CH$_3$ | CH | 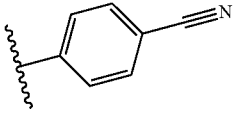 [SMILES: *c1ccc(C#N)cc1] |
| A18 | CH$_3$ | SO$_2$ | —CH$_2$CH$_3$ | S | CF$_3$ | CH$_3$ | CH | 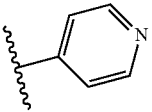 [SMILES: *c1ccncc1] |
| A19 | CH$_3$ | SO$_2$ | —CH$_2$CH$_3$ | S | CF$_3$ | CH$_3$ | CH | 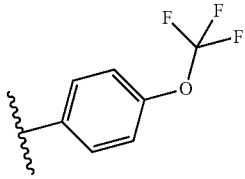 [SMILES: *c1ccc(OC(F)(F)F)cc1] |
| A20 | CH$_3$ | SO$_2$ | —CH$_2$CH$_3$ | S | CF$_3$ | CH$_3$ | CH | 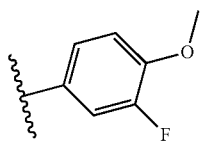 [SMILES: *c1ccc(OC)c(F)c1] |
| A21 | CH$_3$ | SO$_2$ | —CH$_2$CH$_3$ | S | CF$_3$ | CH$_3$ | CH | 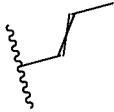 |
| A22 | CH$_3$ | SO$_2$ | —CH$_2$CH$_3$ | S | CF$_3$ | CH$_3$ | CH | 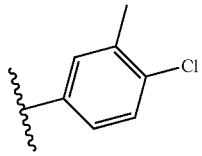 [SMILES: *c1ccc(Cl)c(C)c1] |
| A23 | CH$_3$ | SO$_2$ | —CH$_2$CH$_3$ | S | CF$_3$ | CH$_3$ | CH | 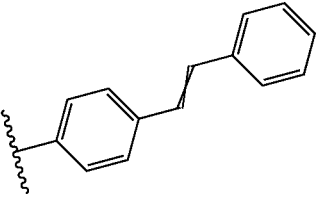 [SMILES: *c1ccc(C=Cc2ccccc2)cc1] |
| A24 | CH$_3$ | SO$_2$ | —CH$_2$CH$_3$ | S | CF$_3$ | CH$_3$ | CH | 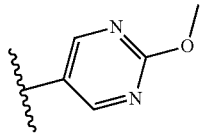 [SMILES: *c1cnc(OC)nc1] |

TABLE 5-continued

| Comp. No. | R$_6$ | X | R$_1$ | A | R$_2$ | R$_4$ | A$_1$ | R$_3$ |
|---|---|---|---|---|---|---|---|---|
| A25 | CH$_3$ | SO$_2$ | —CH$_2$CH$_3$ | S | CF$_3$ | CH$_3$ | CH | 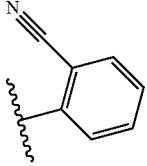 [SMILES: *c1ccccc1C#N] |
| A26 | CH$_3$ | SO$_2$ | —CH$_2$CH$_3$ | S | CF$_3$ | CH$_3$ | CH | 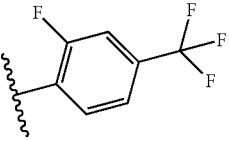 [SMILES: *c1ccc(C(F)(F)F)cc1F] |
| A27 | CH$_3$ | SO$_2$ | —CH$_2$CH$_3$ | S | CF$_3$ | CH$_3$ | CH | 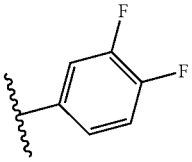 [SMILES: *c1ccc(F)c(F)c1] |
| A28 | CH$_3$ | SO$_2$ | —CH$_2$CH$_3$ | S | CF$_3$ | CH$_3$ | CH | 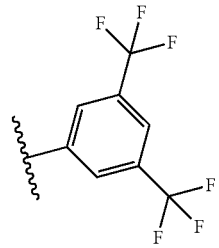 [SMILES: *c1cc(C(F)(F)F)cc(C(F)(F)F)c1] |
| A29 | CH$_3$ | SO$_2$ | —CH$_2$CH$_3$ | S | CF$_3$ | CH$_3$ | CH | 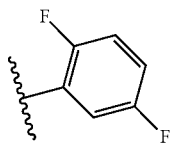 [SMILES: *c1cc(F)ccc1F] |
| A39 | CH$_3$ | S | —CH$_2$CH$_3$ | S | CF$_3$ | CH$_2$CH$_3$ | CH | I |
| A40 | CH$_3$ | SO$_2$ | —CH$_2$CH$_3$ | S | CF$_3$ | CH$_2$CH$_3$ | CH | I |
| A41 | CH$_3$ | SO$_2$ | —CH$_2$CH$_3$ | S | CF$_3$ | CH$_2$CH$_3$ | CH | 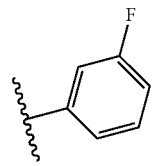 [SMILES: *c1cccc(F)c1] |
| A42 | CH$_3$ | SO$_2$ | —CH$_2$CH$_3$ | S | CF$_3$ | CH$_2$CH$_3$ | CH |  |
| A43 | CH$_3$ | S | —CH$_2$CH$_3$ | S | CF$_3$ | CH$_3$ | CH | I |
| A44 | CH$_3$ | SO$_2$ | —CH$_2$CH$_3$ | S | CF$_3$ | CH$_3$ | CH | I |

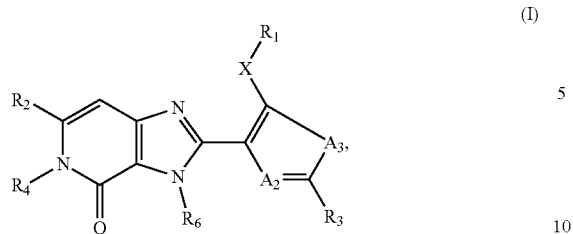
(I)
TABLE 6
| Comp. No. | R6 | X | R1 | A3 | R2 | R4 | A2 | R3 |
|---|---|---|---|---|---|---|---|---|
| A30 (4.006 Y1) | CH3 | SO2 | —CH2CH3 | S | CF3 | CH3 | N | phenyl |
| A31 | CH3 | SO2 | —CH2CH3 | S | CF3 | CH3 | N | pyridin-4-yl |
| A32 | CH3 | SO2 | —CH2CH3 | S | CF3 | CH3 | N | 1-methyl-1H-imidazol-5-yl |
| A33 | CH3 | SO2 | —CH2CH3 | S | CF3 | CH3 | N | 1-methyl-1H-pyrazol-4-yl |
| A34 | CH3 | SO2 | —CH2CH3 | S | CF3 | CH3 | N | 6-(trifluoromethyl)pyridin-3-yl |
| A35 | CH3 | SO2 | —CH2CH3 | S | CF3 | CH3 | N | 3-fluorophenyl |
| A36 (4.006 Y11) | CH3 | SO2 | —CH2CH3 | S | CF3 | CH3 | N | 4-cyanophenyl |
| A37 | CH3 | SO2 | —CH2CH3 | S | CF3 | CH3 | N | thiazol-5-yl |
| A38 | CH3 | SO2 | —CH2CH3 | S | CF3 | CH3 | N | thiophen-3-yl |
| A46 | CH3 | S | —CH2CH3 | S | CF3 | CH3 | N | Br |

TABLE 6-continued

| Comp. No. | $R_6$ | X | $R_1$ | $A_3$ | $R_2$ | $R_4$ | $A_2$ | $R_3$ |
|---|---|---|---|---|---|---|---|---|
| A47 | $CH_3$ | $SO_2$ | —$CH_2CH_3$ | S | $CF_3$ | $CH_3$ | N | Br |
| A48 (4.006 Y4) | $CH_3$ | $SO_2$ | —$CH_2CH_3$ | S | $CF_3$ | $CH_3$ | N | 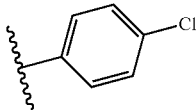 [SMILES: *c1ccc(Cl)cc1] |

FORMULATION EXAMPLES (%=PERCENT BY WEIGHT)

Example F1: Emulsion concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4: Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5: Wettable powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill.
This gives wettable powders, which can be diluted with water to give suspensions of any desired concentration.

Example F6: Extruder granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7: Coated granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8: Suspension concentrate

| Active ingredient | 40% |
|---|---|
| Ethylene glycol | 10% |

-continued

| Example F8: Suspension concentrate | |
|---|---|
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

| Example F9: Powders for dry seed treatment | | | |
|---|---|---|---|
| | a) | b) | c) |
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Example F10: Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Example F11: Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 to 6 of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana*

(53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CON]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E, Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3, 4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+

TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron 586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, a molluscicide selected from the group of substances consisting of bis(tributyltin) oxide (IUPAC name) (913)+TX, bromoacetamide [CON]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imiben-conazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticid in-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ100)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-Wp®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia* pomonella granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox c®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HO®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural Ii®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemba)+TX, canola oil (Lilly Miller Vegol®)+TX, *Chenopodium ambrosioides* near ambrosioides (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX, Z+TX, Z)-3+TX,8+TX,11 Tetradecatrienyl acetate+TX, (Z+TX, Z+TX,E)-7+TX,11+TX,13-Hexadecatrienal+TX, (E+TX, Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-m®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bernipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack+TX, Nematop®)+TX, *Heterorhabditis megidis* (Nemasys H®+TX, BioNem H®+TX, Exhibitline Hm®+TX, Larvanem-m®)+TX, *Hippodamia convergens*+TX, *Hypoaspis aculeifer* (Aculeifer-System®+TX, Entomite-A®)+TX, *Hypoaspis miles* (Hypoline m®+TX, Entomite-m®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-i®+TX, Online i®)+TX, *Orius laevigatus* (Thripor-L®+TX, Oriline i®)+TX, *Orius majusculus* (Online m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac c®+TX, Millenium®+TX, BioNem c®+TX, NemAttack®+TX, Nemastar®+TX, Capsanem®)+TX, *Steinernema feltiae* (NemaShield®+TX, Nemasys f®+TX, BioNem f®+TX, *Steinernema*-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline SrB®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Toiymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zeno+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline Yf®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected from Table 1 to 6 with active ingredients described above comprises a compound selected from Table 1 to 6 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table 1 to 6 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 to 6 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

BIOLOGICAL EXAMPLES

Example B1: Insecticidal Action Against *Bemisia tabaci* (Cotton White Fly): Feeding/Contact Activity Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm:
A3, A6, A10 and A15.

Example B2: Insecticidal Action Against *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
A1, A2, A3, A6, A7, A8, A9, A10, A11, A13, A16, A17, A25, A27, A28, A35, A44 and A48.

Example B3: Insecticidal Action Against *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A2, A3, A4, A6, A7, A8, A10, A11, A12, A13, A16, A17, A18, A19, A21, A22, A25, A26, A27, A29, A33, A35, A44 and A48.

Example B4: Insecticidal Action Against *Myzus persicae* (Green Peach Aphid): Feeding/Contact Activity Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:
A2, A3, A4, A6, A10, A13, A17, A21, A31, A33 and A35.

Example B5: Insecticidal Action Against *Myzus persicae* (Green Peach Aphid): Systemic Activity Roots of pea seedlings infested with an aphid population of mixed ages were placed directly into aqueous test solutions prepared from 10'000 DMSO stock solutions. The samples were assessed for mortality 6 days after placing seedlings into test solutions.

The following compound resulted in at least 80% mortality at a test rate of 24 ppm:
A5.

Example B6: Insecticidal Action Against *Myzus persicae* (Green Peach Aphid): Intrinsic Activity Test compounds prepared from 10'000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compound resulted in at least 80% mortality at a test rate of 12 ppm:
A36.

Example B7: Insecticidal Action Against *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

A1, A2, A3, A4, A5, A6, A7, A8, A9, A10, A11, A12, A13, A14, A15, A16, A17, A19, A20, A21, A22, A23, A24, A25, A26, A27, A29, A30, A31, A32, A33, A34, A35, A44 and A48.

Example B8: Insecticidal Action Against Spodoptera littoralis (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of Spodoptera littoralis by a test sample is given when at least one of the categories mortality, anti-feeding effect, and growth inhibition is higher than the untreated sample.

The following compounds resulted in at least 80% control at an application rate of 200 ppm:

A2, A3, A4, A5, A6, A7, A8, A9, A10, A11, A12, A13, A14, A15, A16, A17, A19, A20, A21, A22, A23, A24, A25, A26, A27, A29, A30, A31, A32, A33, A34, A35, A36, A37, A38, A44 and A48.

Example B9: Insecticidal Action Against Spodoptera littoralis (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. Spodoptera eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:

A3, A4, A6, A10, A11, A15, A17 and A26.

Example B10: Insecticidal Action Against Tetranychus urticae (Two-Spotted Spider Mite): Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:

A6, A19, A20 and A24.

Example B11: Insecticidal Action Against Aedes aegypti (Yellow Fever Mosquito)

Test solutions, at an application rate of 200 ppm in ethanol, were applied to 12 well tissue culture plates. Once the deposits were dry, five, two to five day old adult female Aedes aegypti were added to each well, and sustained with a 10% sucrose solution in a cotton wool plug. Assessment of knockdown was made one hour after introduction, and mortality was assessed at 24 and 48 hours after introduction.

The following compound gave at least 80% control of Aedes aegypti after 48 h and/or 24 h:

A2.

Example B12: Insecticidal Action Against Anopheles stephensi (Indian Malaria Mosquito)

Test solutions, at an application rate of 200 ppm in ethanol, were applied to 12 well tissue culture plates. Once the deposits were dry, five, two to five day old adult female Anopheles stephensi were added to each well, and sustained with a 10% sucrose solution in a cotton wool plug. Assessment of knockdown was made one hour after introduction, and mortality was assessed at 24 and 48 hours after introduction.

The following compound gave at least 80% control of Anopheles stephensi after 48 h and/or 24 h:

A2.

The invention claimed is:
1. A compound of formula I,

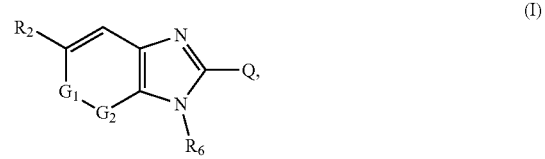

(I)

wherein
Q is $Q_1$ or $Q_2$;

($Q_1$)

($Q_2$)

A and $A_3$, independently from each other, represents S or O;
$A_1$ and $A_2$, independently from each other, represents N or $CR_7$;
X is S, SO or $SO_2$;
$R_1$ is $C_1$-$C_6$alkyl, $C_2$-$C_6$alkenyl, $C_2$-$C_6$haloalkenyl, $C_2$-$C_6$alkynyl, $C_1$-$C_6$haloalkyl, $C_3$-$C_6$cycloalkyl or $C_3$-$C_6$cycloalkyl-$C_1$-$C_4$alkyl; or is $C_3$-$C_6$cycloalkyl mono- or polysubstituted by substituents selected from the group consisting of halogen, cyano and $C_1$-$C_4$alkyl; or is $C_3$-$C_6$cycloalkyl-$C_1$-$C_4$alkyl mono- or polysubstituted by substituents selected from the group consisting of halogen, cyano and $C_1$-$C_4$alkyl;

$R_2$ is hydrogen, halogen, $C_1$-$C_4$haloalkylsulfanyl, $C_1$-$C_4$haloalkylsulfinyl, $C_1$-$C_4$haloalkylsulfonyl, O($C_1$-$C_4$haloalkyl), —SF$_5$, C(O)$C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$alkyl and $C_1$-$C_4$ haloalkyl;

$G_1$ is $NR_4$ and $G_2$ is C(Y); or $G_1$ is C(Y) and $G_2$ is $NR_5$;

Y is O or S;

$R_3$ is hydrogen, halogen, cyano, nitro, amino, $C_1$-$C_6$alkyl, $C_1$-$C_6$haloalkyl, $C_3$-$C_6$cycloalkyl-$C_1$-$C_4$alkyl or $C_3$-$C_6$cycloalkyl which can be mono- or polysubstituted by substituents selected from the group consisting of halogen, $C_1$-$C_2$haloalkyl and cyano; or $R_3$ is $C_2$-$C_6$alkenyl, $C_2$-$C_6$haloalkenyl, $C_2$-$C_6$alkynyl or $C_2$-$C_6$haloalkynyl; or $R_3$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy, —C(O)$C_1$-$C_4$haloalkyl, $C_1$-$C_4$alkylsulfanyl, $C_1$-$C_4$alkylsulfinyl or $C_1$-$C_4$alkylsulfonyl; or $R_3$ is $C_1$-$C_4$alkyl mono- or polysubstituted by substituents selected from the group consisting of cyano, phenyl, pyridine and pyrimidine; or $R_3$ is $C_2$-$C_4$alkenyl mono- or polysubstituted by substituents selected from the group consisting of cyano, $C_3$-$C_6$cycloalkyl, phenyl, pyridine and pyrimidine; or $R_3$ is $C_2$-$C_4$alkynyl mono- or polysubstituted by substituents selected from the group consisting of cyano, $C_1$-$C_4$ alkoxy, $C_3$-$C_6$cycloalkyl, phenyl, pyridine and pyrimidine; or $R_3$ is a five- to ten-membered monocyclic or fused bicyclic ring system linked via a carbon atom to the 5-membered heterocycle, said ring system can be aromatic, partially saturated or fully saturated and can contain 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, nitro, amino, hydroxyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_3$ is a five- to six-membered, aromatic, partially saturated or fully saturated ring system linked via a nitrogen atom to the 5-membered heterocycle, said ring system can be mono- or polysubstituted by substituents selected from the group consisting of halogen, cyano, nitro, amino, hydroxyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulphur, where said ring system may not contain more than one oxygen atom and not more than one sulfur atom;

$R_4$ and $R_5$ are, independently from each other, $C_1$-$C_6$alkyl, $C_1$-$C_6$haloalkyl, or are $C_3$-$C_6$cycloalkyl which can be mono- or poly substituted by $R_7$; or are $C_3$-$C_6$cycloalkyl-$C_1$-$C_4$alkyl which can be mono- or polysubstituted by $R_8$; or $R_4$ and $R_5$ are, independently from each other, $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amino or hydroxyl; or $R_4$ and $R_5$ are, independently from each other, $C_1$-$C_4$ alkyl substituted by $R_9$; or $R_4$ and $R_5$ are, independently from each other, $C_2$-$C_6$alkenyl substituted by $R_9$; or $R_4$ and $R_5$ are, independently from each other, $C_2$-$C_6$alkynyl substituted by $R_9$; or $R_6$ is hydrogen or $C_1$-$C_6$alkyl which can be mono- or polysubstituted by substituents selected from the group consisting of halogen and $C_1$-$C_2$alkylsulfinyl; or $R_6$ is $C_2$-$C_6$alkenyl, $C_2$-$C_6$alkynyl, $C_1$-$C_4$alkoxy-$C_1$-$C_4$alkyl or $C_3$-$C_6$cycloalkyl;

$R_7$ is hydrogen, cyano, halogen, $C_1$-$C_4$alkyl or $C_1$-$C_4$haloalkyl;

$R_8$ is cyano, halogen, $C_1$-$C_4$alkyl or $C_1$-$C_2$haloalkyl;

$R_9$ is cyano, $C_1$-$C_6$alkylsulfanyl, $C_1$-$C_4$alkylsulfonyl, $C_1$-$C_4$alkylsulfinyl, $C_1$-$C_4$haloalkylsulfanyl, $C_1$-$C_4$haloalkylsulfonyl, $C_1$-$C_6$haloalkylsulfinyl, $C_1$-$C_4$alkoxy, $C_1$-$C_4$alkoxy$C_1$-$C_4$alkoxy, $C_3$-$C_6$ cycloalkyl or by phenyl, which itself can be mono- or polysubstituted by substituents selected from the group consisting of halogen, $C_1$-$C_4$alkyl, cyano, $C_1$-$C_4$haloalkyl and $C_1$-$C_4$alkoxy; or an agrochemically acceptable salt, stereoisomer, enantiomer, tautomer or N-oxide thereof.

2. A compound of formula I according to claim 1, wherein $R_3$ is selected from the group consisting of I-0 to I-50:

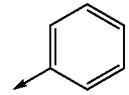

I-0

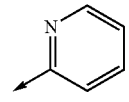

I-1

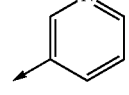

I-2

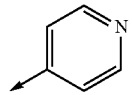

I-3

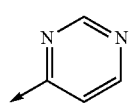

I-4

-continued
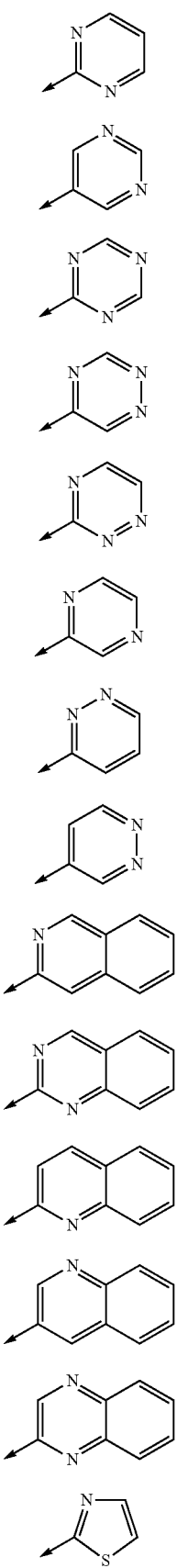
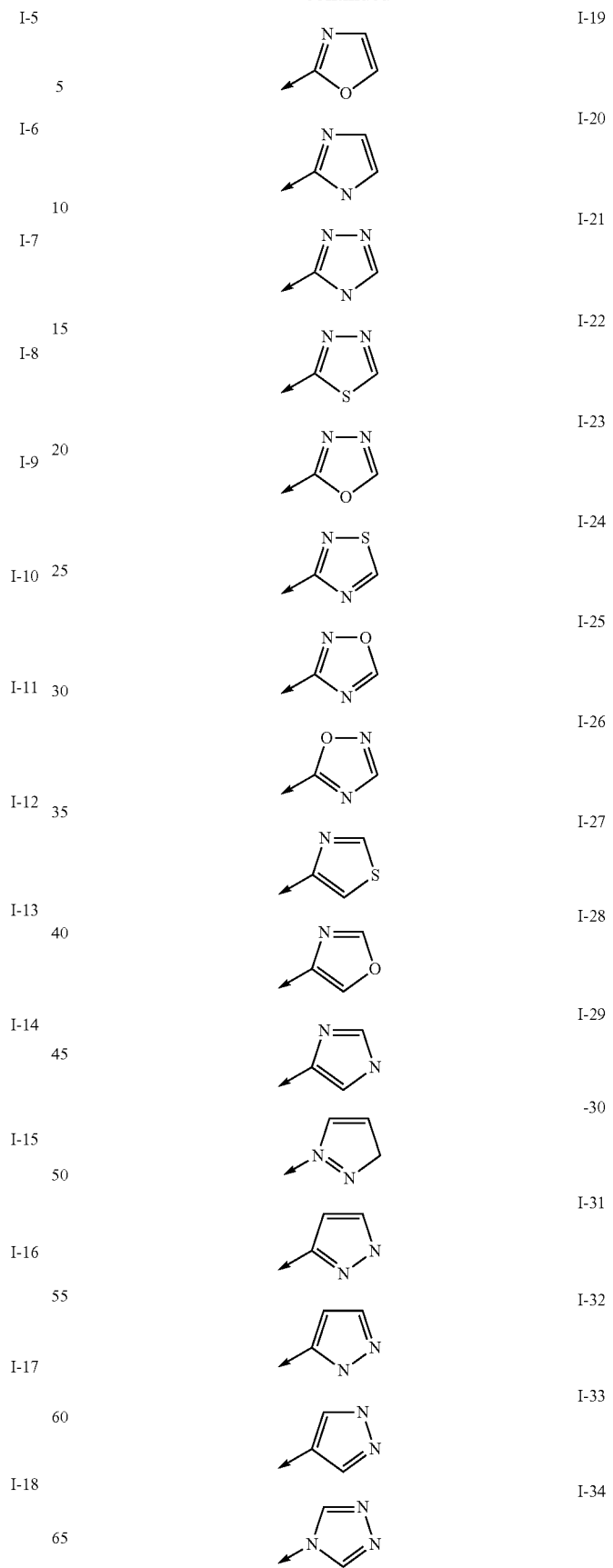

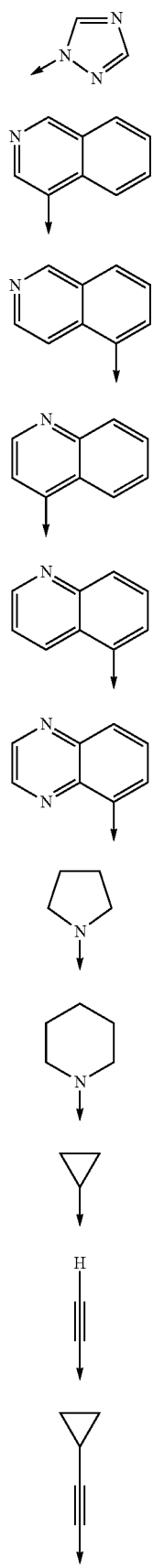

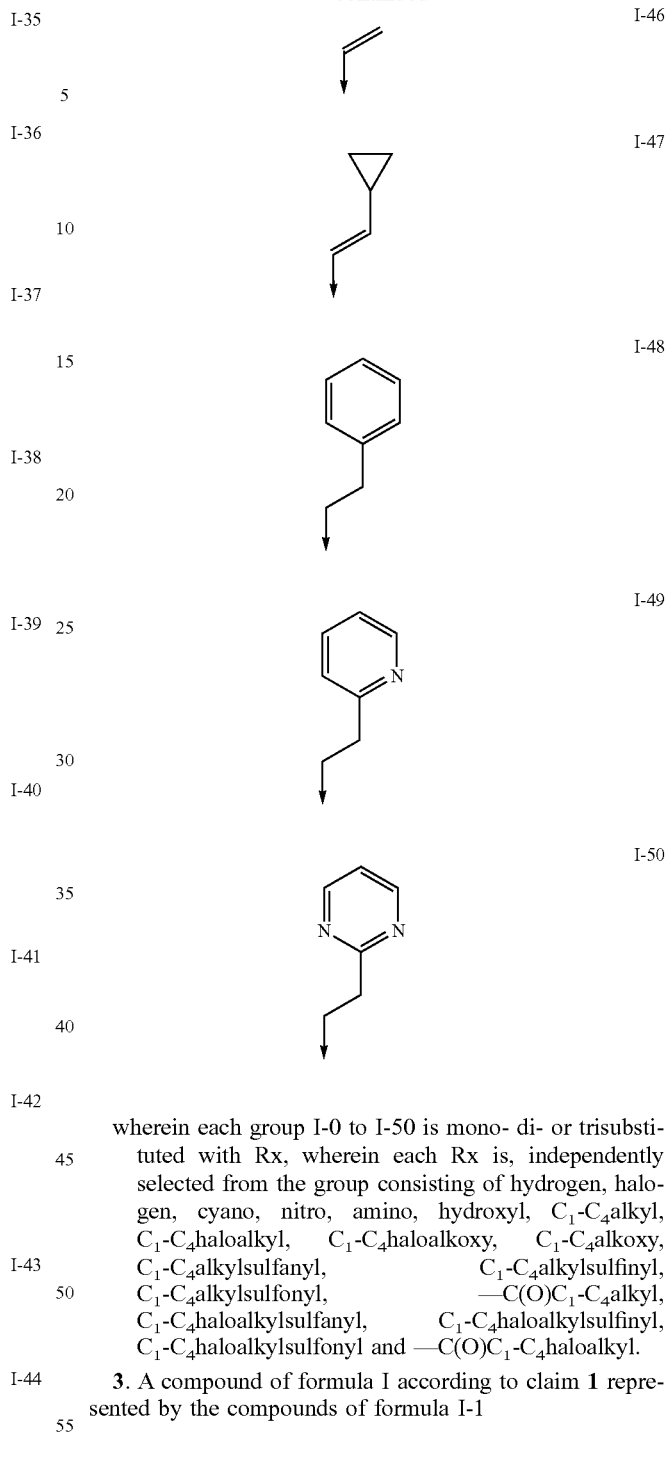

wherein each group I-0 to I-50 is mono- di- or trisubstituted with Rx, wherein each Rx is, independently selected from the group consisting of hydrogen, halogen, cyano, nitro, amino, hydroxyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

3. A compound of formula I according to claim 1 represented by the compounds of formula I-1

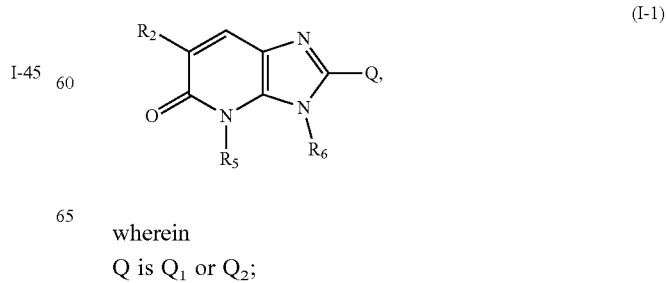

(I-1)

wherein

Q is $Q_1$ or $Q_2$;

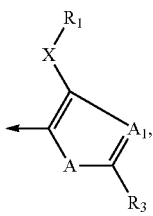
(Q₁)

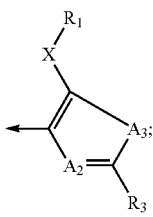
(Q₂)

wherein the substituents X, A, A₁, A₂, A₃, R₁, R₂, R₃, R₅ and R₆ are as defined under formula I in claim 1.

4. A compound of formula I-1 according to claim 3, wherein

R₁ is C₁-C₄alkyl, C₃-C₆cycloalkyl-C₁-C₄alkyl or C₃-C₆cycloalkyl; and

R₂ is halogen, C₁-C₄haloalkylsulfanyl, C₁-C₄haloalkylsulfinyl, C₁-C₄haloalkylsulfonyl, C₁-C₄haloalkoxy, C₁-C₄haloalkyl, cyano or is C₃-C₆cycloalkyl which can be mono- or polysubstituted by substituents selected from the group consisting of halogen, cyano and C₁-C₄alkyl.

5. A compound of formula I according to claim 1 represented by the compounds of formula I-1a

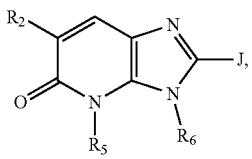
(I-1a)

wherein J is selected from the group consisting of J1, J2 and J3

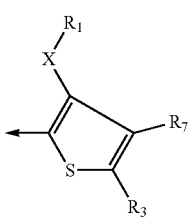
J1

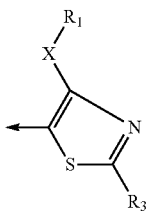
J2

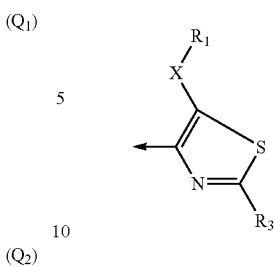
J3

R₁ is C₁-C₄alkyl, C₃-C₆cycloalkyl-C₁-C₄alkyl or C₃-C₆cycloalkyl;

R₂ is halogen, C₁-C₄haloalkylsulfanyl, C₁-C₄haloalkylsulfinyl, C₁-C₄haloalkylsulfonyl, C₁-C₄haloalkoxy, C₁-C₄haloalkyl, cyano or is C₃-C₆cycloalkyl which can be mono- or polysubstituted by substituents selected from the group consisting of halogen, cyano and C₁-C₄alkyl and X, R₃, R₅, R₆ and R₇ are as defined under formula I in claim 1.

6. A compound of formula I according to claim 1 represented by the compounds of formula I-2

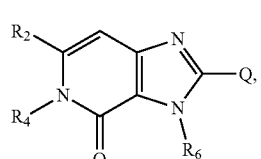
(I-2)

wherein
Q is Q₁ or Q₂;

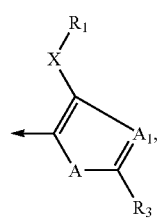
(Q₁)

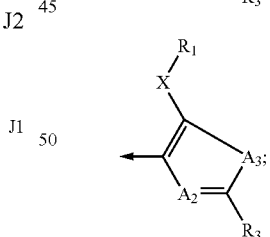
(Q₂)

wherein the substituents X, A, A₁, A₂, A₃, R₁, R₂, R₄, R₃ and R₆ are as defined under formula I in claim 1.

7. A compound of formula I-2 according to claim 6, wherein

R₁ is C₁-C₄alkyl, C₃-C₆cycloalkyl-C₁-C₄alkyl or C₃-C₆cycloalkyl; and

R₂ is halogen, C₁-C₄haloalkylsulfanyl, C₁-C₄haloalkylsulfinyl, C₁-C₄haloalkylsulfonyl, C₁-C₄haloalkoxy, C₁-C₄haloalkyl or cyano, or is C₃-C₆cycloalkyl which can be mono- or polysubstituted by substituents selected from the group consisting of halogen, cyano and C₁-C₄alkyl.

8. A compound of formula I according to claim 1 represented by the compounds of formula I-2a

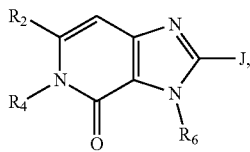
(I-2a)

wherein J is selected from the group consisting of

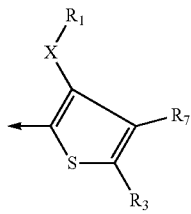
J1

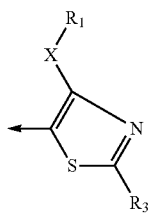
J2

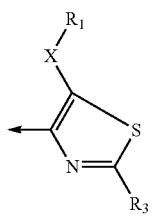
J3

$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;

and X, $R_3$, $R_4$ $R_6$ and $R_7$ are as defined under formula I in claim 1.

9. A compound of formula I according to claim 1 represented by the compounds of formula I-2a

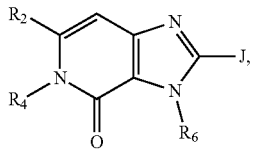
(I-2a)

wherein J is $J_1$ or $J_3$

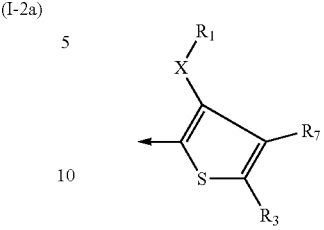
J1

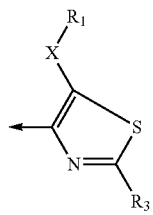
J3

$R_1$ is ethyl;

X is S, S(O) or $SO_2$;

$R_2$ is $CF_3$;

$R_4$ is methyl or ethyl;

$R_6$ is methyl;

$R_3$ is halogen; or $R_3$ is $C_2$-$C_4$alkenyl or $C_2$-$C_4$alkenyl substituted by phenyl; or $R_3$ is $C_2$-$C_4$alkynyl or $C_2$-$C_4$alkynyl mono- or polysubstituted by $C_1$-$C_4$alkoxy; or $R_3$ is a ring system selected from phenyl, pyrimidinyl, pyridyl, thienyl, imidazolyl, pyrazolyl and thiazolyl; said ring system can be mono- or polysubstituted by substituents selected from the group consisting of halogen, $C_1$-$C_2$haloalkyl, cyano, $C_1$-$C_2$haloalkoxy, $C_1$-$C_2$alkoxy, $C_1$-$C_2$alkylsulfinyl and $C_1$-$C_2$alkyl.

10. A insecticidal and acarinicidal composition, which comprises at least one compound of formula I according to claim 1 or, where appropriate, a tautomer thereof, in each case in free form or in agrochemically utilizable salt form, as active ingredient and at least one auxiliary.

11. A method for controlling insects and acarina, which comprises applying a composition according to claim 10 to the pests or their environment with the exception of a method for treatment of the human or animal body by surgery or therapy and diagnostic methods practised on the human or animal body.

12. A method for the protection of seeds from the attack by insects and acarina, which comprises treating the seeds or the site, where the seeds are planted, with a composition according to claim 10.

* * * * *